United States Patent
Rapp et al.

(10) Patent No.: US 7,541,512 B2
(45) Date of Patent: *Jun. 2, 2009

(54) AVIANS CONTAINING A LYSOZYME PROMOTER TRANSGENE

(75) Inventors: Jeffrey C. Rapp, Athens, GA (US); Alex J. Harvey, Athens, GA (US)

(73) Assignee: Synageva BioPharma Corp., Waltham, MA (US)

( * ) Notice: Subject to any disclaimer, the term of this patent is extended or adjusted under 35 U.S.C. 154(b) by 35 days.

This patent is subject to a terminal disclaimer.

(21) Appl. No.: 11/699,257

(22) Filed: Jan. 26, 2007

(65) Prior Publication Data

US 2007/0124829 A1    May 31, 2007

Related U.S. Application Data

(63) Continuation-in-part of application No. 10/114,739, filed on Apr. 1, 2002, now Pat. No. 7,199,729, and a continuation-in-part of application No. 09/922,549, filed on Aug. 3, 2001, now Pat. No. 7,176,300.

(60) Provisional application No. 60/351,550, filed on Jan. 25, 2002, provisional application No. 60/280,004, filed on Mar. 30, 2001.

(51) Int. Cl.
*A01K 67/027* (2006.01)
*C12N 15/00* (2006.01)

(52) U.S. Cl. .......................................... 800/19; 800/21

(58) Field of Classification Search .................. 800/19, 800/21
See application file for complete search history.

(56) References Cited

U.S. PATENT DOCUMENTS

| | | | |
|---|---|---|---|
| 4,237,224 A | 12/1980 | Cohen et al. | |
| 4,603,112 A | 7/1986 | Paoletti et al. | |
| 4,722,848 A | 2/1988 | Paoletti et al. | |
| 4,769,330 A | 9/1988 | Paoletti et al. | |
| 5,174,993 A | 12/1992 | Paoletti et al. | |
| 5,175,384 A | 12/1992 | Krimpenfort et al. | |
| 5,338,683 A | 8/1994 | Paoletti et al. | |
| 5,494,807 A | 2/1996 | Paoletti et al. | |
| 5,505,941 A | 4/1996 | Paoletti et al. | |
| 5,580,859 A | 12/1996 | Felgner et al. | |
| 5,589,466 A | 12/1996 | Felgner et al. | |
| 5,591,639 A | 1/1997 | Bebbington | |
| 5,731,178 A | 3/1998 | Sippel et al. | |
| 5,897,998 A | 4/1999 | Speksnijder et al. | |
| 6,825,396 B2* | 11/2004 | MacArthur | 800/19 |
| 7,312,374 B2* | 12/2007 | Rapp et al. | 800/21 |
| 2005/0034186 A1 | 2/2005 | Harvey | |
| 2005/0176047 A1 | 8/2005 | Harvey et al. | |
| 2006/0015960 A1 | 1/2006 | Ivarie et al. | |
| 2006/0174364 A1 | 8/2006 | Christmann et al. | |

FOREIGN PATENT DOCUMENTS

| | | |
|---|---|---|
| WO | WO 91/06309 | 5/1991 |
| WO | WO 92/06180 | 4/1992 |
| WO | WO 92/19749 | 11/1992 |
| WO | WO 92/20316 | 11/1992 |
| WO | WO 92/22635 | 12/1992 |
| WO | WO 93/04701 | 3/1993 |
| WO | WO 93/25234 | 12/1993 |
| WO | WO 94/06920 | 3/1994 |
| WO | WO 94/11524 | 5/1994 |
| WO | WO 97/47739 | 12/1997 |
| WO | WO 99/19472 | 4/1999 |
| WO | WO 00/11151 | 3/2000 |
| WO | WO 00/56932 | 9/2000 |
| WO | WO 01/14424 A2 | 3/2001 |
| WO | WO 02/20752 A2 | 3/2002 |

OTHER PUBLICATIONS

Exons encode functional and structural units of chicken lysozyme, Jung et al; PNAS USA,77:5759-5763, (Oct. 1980).
An Initiation Zone of Chromosomal DNA Replication at the Chicken Lysozyme Gene Locus*, Loc Phi-van et al; The Journal of Biological Chemistry 273:18300-18307 (1998).
The matrix attachment regions of the chicken lysozyme gene co-map with the boundaries of the chromatin domain, Phi-Van and Stratling; EMBO Journal 7:655-664 (1988).
Lysozme Level in Blood Serum of Newly Hatched White Leghorn Chickens, Rosolowska-Huszcz; Bulletin De L'academie Polonaise Des Sciences, 26:891-894 (1978).
Prerequisites for tissue specific and position independent expression of a gene locus in transgenic mice, Bonifer et al; J Mol Med 74:663-671(1996).
A nuclear DNA attachment element mediates elevated and position-independent gene activity, Stief et al; Nature 341:343-345(Sep. 1989).
Tissue specific and position independent expression of the complete gene domain for chicken lysozyme in transgenic mice, Bonifer et al; EMBO Journal 9:2843-2848 (1990).
Stopped at the border; boundaries and insulators, Bell and Felsenfeld; Current Opinion in Genetics & Development,9:191-198(1999).
Dissection of the Ability of the Chicken Lysozyme Gene 5' Matrix Attachment Region To Stimulate Transgene Expression and To Dampen Position Effects; Phi-Van and Stratling; Biochemistry 35:10735-10742(1996).
Activity of two different silencer elements of the chicken lysozyme gene can be compensated by enhancer elements, Baniahmad et al; EMBO Journal 6:2297-2303(1987).
The lysozyme enhancer: cell-specific activation of the chicken lysozyme gene by a far-upstream DNA element, Theisen et al; EMBO Journal 5:719-724(1986).
The Chicken Lysozyme Locus as a Paradigm for the Complex Developmental Regulation of Eukaryotic Gene Loci, Bonifer et al; Journal of Biological Chemistry 272:26075-26078(1997).

(Continued)

*Primary Examiner*—Michael C. Wilson
(74) *Attorney, Agent, or Firm*—Kyle D. Yesland

(57) ABSTRACT

The invention provides for transgenic avians containing nucleic acids which include an exogenous lysozyme gene expression controlling nucleotide sequence which typically is linked to a polynucleotide encoding a heterologous polypeptide.

11 Claims, 34 Drawing Sheets

OTHER PUBLICATIONS

A progesterone responsive element maps to the far upstream steroid dependent DNase hypersensitive site of chicken lysozyme chromatin, Hecht et al; EMBO Journal 7:2063-2073(1988).

Chromatin fine structure profiles for a developmentally regulated gene: reorganization of the lysozyme locus before trans-activator binding and gene expression, Kontaraki et al.; Genes & Development 14:210-2122(2000).

The Far Upstream Chicken Lysozyme Enhancer at-6.1 Kilobase, by Interacting with NF-M, Mediates Lipopolysaccharide-induced Expression of the Chicken Lysozyme Gene in Chicken Myelomonocytic Cells, Goethe and Phi Van; Journal of Biological Chemistry 269:31302-31309(1994).

Chromatin Domains Constitute Regulatory Units for the Control of Eukaryotic genes, Sippel et al;Cold Spring Harbor Symposia on Quantitative Biology, 58:37-44(1993).

Dynamic Changes in the Chromatin of the Chicken Lysozyme Gene Domain During Differentiation of Multipotent Progenitors to Macrophages, Huber et al; DNA and Cell Biology 14:397-402(1995).

Alternative sets of DNase I-hypersensitive sites characterize the various functional states of the chicken lysozyme gene, Fritton et al; Nature 311:163-165(Sep. 1984).

Reduced Position Effect in Mature Transgenic Plants conferred by the Chicken Lysozyme Matrix-Associated Region, Mlynarova et al;The Plant Cell 6:417-426(1994).

Development of position-independent expression vectors and their transfer into transgenic fish, Caldovic and Hackett; Mol. Marine Biol. and Biotech 4:51-61(1995).

Chicken repeat 1(CR1) elements, which define an ancient family of vertebrate non-LTR retrotransposons, contain two closely spaced open reading frames, Haas et al; Gene 197:305-309(1997).

Sequence conservation in avian CR1: An interspersed repetitive DNA family evolving under functional constraints, Chen et al; PNAS USA 88:5814-5818 (Jul. 1991).

Position-independent expression of transgenes in zebrafish, Caldovic et al; Transgenic Research 8:321-334(1999).

Lysozyme in Hen Blood Serum, Sato and Watanabe, Poultry Science 55:1749-1756(1976).

Untitled, Steiner et al; Nucleic Acids Research, 15:4163-4178 (1987).

The chicken lysozyme chromatin domain contains a second, widely expressed gene, Chong et al., Nucleic Acids Research vol. 30, No. 2 (2002) 463-467.

Altschul, et al. Basic Local Alignment Search Tool. *Journal of Molecular Biology* (1990) 215: 403-410.

Altschul, et al. Gapped BLAST and PSI-BLAST: a new generation of protein database search programs. *Nucleic Acids Research* (1997) 25(17): 3389-3402.

Ausubel, et al. Introduction of DNA into Mammalian Cells. *Current Protocols in Molecular Biology* (1996) 9.10-9.14.

Berkner, Kathleen. Development of Adenovirus Vectors for the Expression of Heterologous Genes. *BioTechniques* (1988) 6(7): 616-629.

Collas and Alestrom. Nuclear Localization Signal of SV40 T Antigen Directs Import of Plasmid DNA into Sea Urchin Male Pronuclei In Vitro. *Molecular Reproduction and Development* (1996) 45:431-438.

Cosset, et al. Improvement of Avian Leukosis Virus (ALV)-Based Retrovirus Vectors by Using Different *cis*-Acting Sequences from ALVs. *Journal of Virology* (1991) 65(6): 3388-3394.

Christiano, et al. Hepatic gene therapy: Adenovirus enhancement of receptor-mediated gene delivery and expression in primary hepatocytes. *Proceedings of the National Academy of the Sciences* (1993) 90:2122-2126.

Erlich, et al. Recent Advances in the Polymerase Chain Reaction. *Science* (1991) 252: 1643-1651.

Flotte, et al. Expression of the Cystic Fibrosis Transmembrane Conductance Regulator from a Novel Adeno-associated Virus Promoter. *Journal of Biological Chemistry* (1993) 268(5): 3781-3790.

Frolov, et al. Alphavirus-based expression vectors: Strategies and applications. *Proceedings of the National Academy of the Sciences* (1996) 93: 11371-11377.

Gordon, et al. Production of human tissue plasminogen activator in transgenic mouse milk. Biotechnology (1987) 5: 1183-1187.

Goud, et al. Antibody-Mediated Binding of a Murine Ecotropic Moloney Retroviral Vector to Human Cells Allows Internalization But Not the Establishment of the Proviral State. *Virology* (1988) 163: 251-254.

Graham, et al. Manipulation of Adenovirus Vectors. *Methods in Molecular Biology, Vol. 7: Gene Transfer and Expression Protocols.* (1991) 109-128. Humana Press Inc., Clifton, NJ.

Grunstein, et al. Colony hybridization: A method for the isolation of cloned DNAs that contain a specific gene. *Proceedings of the National Academy of the Sciences* (1975) 72(10):3961-3965.

Hermonat, et al. Use of adeno-associated virus as a mammalian DNA cloning vector: Transduction of neomycin resistance into mammalian tissue culture cells. *Proceedings of the National Academy of the Sciences* (1984) 81:6466-6470.

Jones, et al. Isolation of Adenovirus Type 5 Host Range Deletion Mutants Defective for Transformation of Rat Embryo Cells. *Cells* (1979) 17: 683-689.

Karlin, et al. Methods for assessing the statistical significance of molecular sequence features by using general scoring schemes. *Proceedings of the National Academy of the Sciences* (1990) 87: 2264-2268.

Karlin, et al. Applications and statistics for multiple high-scoring segments in molecular sequences. *Proceedings of the National Academy of the Sciences* (1993) 90: 5873-5877.

Meinkoth, et al. Hybridization of Nucleic Acids Immobilized on Solid Supports. *Analytical Biochemistry* (1984) 138: 267-284.

Mizuno, et al. Basic Research for interferon gene therapy against malignant glioma. *No Shinkei Geka* (1992) 20(5): 547-551.

Moss, Bernard. Genetically engineered poxviruses for recombinant gene expression, vaccination, and safety. *Proceedings of the National Academy of the Sciences* (1996) 93: 11341-11348.

Mulligan, Richard C. The Basic Science of Gene Therapy. *Science* (1993) 260: 926-932.

Neda, et al. Chemical Modification of an Ecotropic Murine Leukemia Virus Results in Redirection of Its Target Cell Specificity. *Journal of Biological Chemistry* (1991) 266(22): 14143-14146.

Paoletti, Enzo. Applications of pox virus vectors to vaccination: An update. *Proceedings of the National Academy of the Sciences* (1996) 93: 11349-11353.

Roizman, Bernard. The function of herpes simplex virus genes: A primer for genetic engineering of novel vectors. *Proceedings of the National Academy of the Sciences* (1996) 93: 11307-11312.

Rosenfeld, et al. Adenovirus-Mediated Transfer of a Recombinant α1-Antitrypsin Gene to the Lung Epithelium in Vivo. *Science* (1991) 252: 431-434.

Rosenfeld, et al. In Vivo Transfer of the Human Cystic Fibrosis Transmembrane Conductance Regulator Gene to the Airway Epithelium. *Cell* (1992) 68: 143-155.

Roux, et al. A versatile and potentially general approach to the targeting of specific cell types by retroviruses: Application to the infection of human cells by means of major histocompatibility complex class I and class II antigens by mouse ecotropic murine leukemia virus-derived viruses. *Proceedings of the National Academy of the Sciences* (1989) 86: 9079-9083.

Schutz, et al. Hormonal Control of Egg White Protein Messenger RNA Synthesis in the Chicken Oviduct. *Cold Spring Harbor Symposium on Quantitative Biology* (1978) 42: 617-624.

Sippel, et al. The Structural and Functional Domain Organization of the Chicken Lysozyme Gene Locus. *Nucleic Acids and Molecular Biology* (1989) 3: 133-147.

Southern, E.M. Detection of Specific Sequences Among DNA Fragments Separated by Gel Electrophoresis. *Journal of Molecular Biology* (1975) 98: 593-517.

Stein, et al. Tissue-specific expression of a chicken calmodulin pseudogene lacking intervening sequences. *Proceedings of the National Academy of the Sciences* (1983) 80: 6485-6489.

Thomas, Patricia S. Hybridization of denatured RNA and small DNA fragments transferred to nitrocellulose. *Proceedings of the National Academy of the Sciences* (1980) 77(9): 5201-5205.

Tratschin, et al. Genetic Analysis of Adeno-Associated Virus: Properties of Deletion Mutants Constructed In Vitro and Evidence for an Adeno-Associated Virus Replication Function. *Journal of Virology* (1984) 51(3): 611-619.

Tratschin, et al. Adeno-Associated Virus Vector for High-Frequency Integration, Expression, and Rescue of Genes in Mammalian Cells. *Molecular and Cellular Biology* (1985) 5(11): 3251-3260.

Wagner, et al. Influenza virus hemagglutinin HA-2 N-terminal fusogenic peptides augment gene transfer by transferring-polylysine-DNA complexes: Toward a synthetic virus-like gene-transfer vehicle. *Proceedings of the National Academy of the Sciences* (1992) 89: 7934-7938.

Watson, et al. Restriction Fragment Length Polymorphisms Serve as Markers for Linkage Analysis. *Recombinant DNA*. Scientific American Books, New York (1992) pp. 519-522, 545-547.

Wilmut, et al. Methods of Gene Transfer and Their Potential Use to Modify Milk Consumption. *Theriogenology* (1990) 33(1): 113-123.

Wondisford, et al. Cloning of the Human Thyrotropin b-Subunit Gene and Transient Expression of Biologically Active Human Thyrotropin after Gene Transfection. *Molecular Endocrinology* (1988) 2(1): 32-39.

Alberts et al., Molecular Biology of the Cell 3$^{rd}$ ed., Garland Publishing, New york pp. 6 and 227 (1994).

Grenwall T, Theisen M, Borgmeyer U, Grussenmeyer T, Rupp RA, Stief A, Qian F, Hecht A, Sippel AE, The -6.1-kilobase chicken lysozyme enhancer is a multifactorial complex containing several cell-type-specific elements. Mol Cell Biol. 12(5):2339-50 (1992).

Jung A, Sippel AE, Grez M, Schutz G., Exons encode functional and structural units of chicken lysozyme, Proc Natl Acad Sci USA, 77(10):5759-63 (1980).

Renkawitz R, Schutz G, von der Ahe D, Beato M, Sequences in the promoter region of the chicken lysozyme gene required for steroid regulation and receptor binding, Cell, 37(2):503-10 (1984).

Stumph WE, Hodgson CP, Tsai MJ, O'Malley BW, Genomic structure and possible retroviral origin of the chicken CR1 repetitive DNA sequence family, Proc Natl Acad Sci USA, 81(21):6667-71 (1984).

Von Kries JP, Phi-Van L, Diekmann S, Stratling WH, A non-curved chicken lysozyme 5' matrix attachment site is 3' followed by a strongly curved DNA sequence, Mucleic Acids Res, 11:18(13):3881-5 (1990).

Wagstrom EA, Yoon KJ, Zimmerman JJ, Immune components in porcine mammary secretions, Viral Immunol 13(3):383-97 (1980).

* cited by examiner

5pLMAR2
TGCCGCCTTCTTTGATATTC                                SEQ ID NO: 1

LE-6.1kbrev1
TTGGTGGTAAGGCCTTTTTG                                SEQ ID NO: 2

Lys-6.1
CTGGCAAGCTGTCAAAAACA                                SEQ ID NO: 3

LysE1rev
CAGCTCACATCGTCCAAAGA                                SEQ ID NO: 4

LYSBSU
CCCCCCCCTAAGGCAGCCAGGGGCAGGAAGCAAA                  SEQ ID NO: 5

SalItoNotI
TCGAGCGGCCGC                                        SEQ ID NO: 6

T7
TAATACGACTCACTATAGGG                                SEQ ID NO: 7 lys61enfor1
CGTGGTGATCAAATCTTTGTG                               SEQ ID NO: 8 lys61enrev1
AGGAGGGCACAGTAGGGATC                                SEQ ID NO: 9

5MARfor1
GTGGCCTGTGTCTGTGCTT                                 SEQ ID NO: 10

IFN-3rev
AACTCCTCTTGAGGAAAGCC                                SEQ ID NO: 11 lys001rev
TCCTGTTTGGGATGAATGGT                                SEQ ID NO: 12 lys002for
CTCTCAGAATGCCCAACTCC                                SEQ ID NO: 13 lys003for
TGTATTGGTCTCCCTCCTGC                                SEQ ID NO: 14 lys005for
TGTTGAAATTGCAGTGTGGC                                SEQ ID NO: 15 lys006rev
TGACAATGCAAATTTGGCTC                                SEQ ID NO: 16

*Fig. 1a* lys007for
GATATCCTTGCAGTGCCCAT                     SEQ ID NO: 17 lys008rev
GGACAAGCAAGTGCATCAGA                     SEQ ID NO: 18 lys009for
CTGATGTGCTTCAGCTCTGC                     SEQ ID NO: 19 lys010rev
TCCATGGTGGTCAAACAGAA                     SEQ ID NO: 20 lys011for
GTACTAGACCAGGCAGCCCA                     SEQ ID NO: 21 lys012rev
GTGGGAAGTACCACATTGGC                     SEQ ID NO: 22 lys013for
CGCTCAGGAGAAAGTGAACC                     SEQ ID NO: 23 lys014rev
CGGTTTTGCCTTTGTGTTTT                     SEQ ID NO: 24 lys015rev
AAATGCTCGATTTCATTGGG                     SEQ ID NO: 25 lys016rev
GCCAATCAGACTGCATTTCA                     SEQ ID NO: 26 lys017rev
AACCGCTGAATGGAACAGTC                     SEQ ID NO: 27 lys018for
ACACGCACATATTTTGCTGG                     SEQ ID NO: 28 lys019rev
CAGGAGCTGGATTCCTTCAG                     SEQ ID NO: 29 lys020for
AAAGGATGCAGTCCCAAATG                     SEQ ID NO: 30 lys021rev
GCCCCTAGACTCCATCTTCC                     SEQ ID NO: 31 lys022rev
ATTTGCTGTGGTGGATGTGA                     SEQ ID NO: 32

*Fig. 1b* lys024for
CCTTGCAGTCCTTGGTTTGT          SEQ ID NO: 33 lys025rev
ATGATCCTTCTGATGGGCTG          SEQ ID NO: 34 lys026rev
ACAGTGATAGCACAAGGGGG          SEQ ID NO: 35 lys027rev
GTAAACAGCTGCAACAGGCA          SEQ ID NO: 36 lys028rev
CAACACAAAAGTTGGACAGCA         SEQ ID NO: 37 lys029rev
TTTGCAGATGAGACGTTTGC          SEQ ID NO: 38 lys030rev
CCACAAGTTCTTGTTTGGGC          SEQ ID NO: 39 lys031rev
ATCAATCCATGCCAGTAGCC          SEQ ID NO: 40 lys032rev
GTTTAAGGCCCCTTCCAATC          SEQ ID NO: 41 lys033for
GAGAGGGGGTTGGGTGTATT          SEQ ID NO: 42 lys034for
ACAGTGGAAGCATTCAAGGG          SEQ ID NO: 43 lys037for
CCAATGCCTTTGGTTCTGAT          SEQ ID NO: 44 lys038for
AAAACACAAAGGCAAAACCG          SEQ ID NO: 45 lys039rev
CTAAGCCTCGCCAGTTTCAA          SEQ ID NO: 46 lys040rev
TGCCATGAAAACCCTACTGA          SEQ ID NO: 47 lys041for
GGAATGTACCCTCAGCTCCA          SEQ ID NO: 48

*Fig. 1c* lys042rev
CCTCTTTAGGAGGCCAGCTT                     SEQ ID NO: 49 lys043rev
AAGATGATCAGAGGGCTGGA                     SEQ ID NO: 50 lys044rev
GCAGCGCTGGTAATCTTCAT                     SEQ ID NO: 51 lys045for
CTTCAGATCCCAGGAAGTGC                     SEQ ID NO: 52 lys046for
TTCCTGCCTTACATTCTGGG                     SEQ ID NO: 53 lys047for
CCCACTGCAGGCTTAGAAAG                     SEQ ID NO: 54 lys048for
AGTTCTCCATAGCGGCTGAA                     SEQ ID NO: 55 lys051for
TGCATCCTTCAGCACTTGAG                     SEQ ID NO: 56 lys052rev
GCAGGAGGGAGACCAATACA                     SEQ ID NO: 57 lys053for
TGCACAAGGATGTCTGGGTA                     SEQ ID NO: 58 lys054for
TCCTAGCAACTGCGGATTTT                     SEQ ID NO: 59 lys056for
TCTTCCATGTTGGTGACAGC                     SEQ ID NO: 60 lys058for
CCCCCTTGTGCTATCACTGT                     SEQ ID NO: 61 lys059for
CTGACAGACATCCCAGCTCA                     SEQ ID NO: 62 lys060for
AAGTTGTGCTTCTGCGTGTG                     SEQ ID NO: 63 lys061for
TTGTTCCTGCTGTTCCTCCT                     SEQ ID NO: 64

*Fig. 1d*

SEQ ID NO: 65

```
TGCCGCCTTC TTTGATATTC ACTCTGTTGT ATTTCATCTC TTCTTGCCGA TGAAAGGATA 60
TAACAGTCTG TATAACAGTC TGTGAGGAAA TACTTGGTAT TTCTTCTGAT CAGTGTTTTT 120
ATAAGTAATG TTGAATATTG GATAAGGCTG TGTGTCCTTT GTCTTGGGAG ACAAAGCCCA 180
CAGCAGGTGG TGGTTGGGGT GGTGGCAGCT CAGTGACAGG AGAGGTTTTT TTGCCTGTTT 240
TTTTTTTTTT TTTTTTTTTT AAGTAAGGTG TTCTTTTTTC TTAGTAAATT TTCTACTGGA 300
CTGTATGTTT TGACAGGTCA GAAACATTTC TTCAAAAGAA GAACCTTTTG GAAACTGTAC 360
AGCCCTTTTC TTTCATTCCC TTTTTGCTTT CTGTGCCAAT GCCTTTGGTT CTGATTGCAT 420
TATGGAAAAC GTTGATCGGA ACTTGAGGTT TTTATTTATA GTGTGGCTTG AAAGCTTGGA 480
TAGCTGTTGT TACACGAGAT ACCTTATTAA GTTTAGGCCA GCTTGATGCT TTATTTTTC 540
CCTTTGAAGT AGTGAGCGTT CTCTGGTTTT TTTCCTTTGA AACTGGTGAG GCTTAGATTT 600
TTCTAATGGG ATTTTTTACC TGATGATCTA GTTGCATACC CAAATGCTTG TAAATGTTTT 660
CCTAGTTAAC ATGTTGATAA CTTCGGATTT ACATGTTGTA TATACTTGTC ATCTGTGTTT 720
CTAGTAAAAA TATATGGCAT TTATAGAAAT ACGTAATTCC TGATTTCCTT TTTTTTTATC 780
TCTATGCTCT GTGTGTACAG GTCAAACAGA CTTCACTCCT ATTTTTATTT ATAGAATTTT 840
ATATGCAGTC TGTCGTTGGT TCTTGTGTTG TAAGGATACA GCCTTAAATT TCCTAGAGCG 900
ATGCTCAGTA AGGCGGGTTG TCACATGGGT TCAAATGTAA AACGGGCACG TTTGGCTGCT 960
GCCTTCCCGA GATCCAGGAC ACTAAACTGC TTCTGCACTG AGGTATAAAT CGCTTCAGAT 1020
CCCAGGGAAG TGCAGATCCA CGTGCATATT CTTAAAGAAG AATGAATACT TTCTAAAATA 1080
TTTTGGCATA GGAAGCAAGC TGCATGGATT TGTTTGGGAC TTAAATTATT TTGGTAACGG 1140
AGTGCATAGG TTTTAAACAC AGTTGCAGCA TGCTAACGAG TCACAGCGTT TATGCAGAAG 1200
TGATGCCTGG ATGCCTGTTG CAGCTGTTTA CGGCACTGCC TTGCAGTGAG CATTGCAGAT 1260
AGGGGTGGGG TGCTTTGTGT CGTGTTCCCA CACGCTGCCA CACAGCCACC TCCCGGAACA 1320
CATCTCACCT GCTGGGTACT TTTCAAACCA TCTTAGCAGT AGTAGATGAG TTACTATGAA 1380
ACAGAGAAGT TCCTCAGTTG GATATTCTCA TGGGATGTCT TTTTTCCCAT GTTGGGCAAA 1440
GTATGATAAA GCATCTCTAT TTGTAAATTA TGCACTTGTT AGTTCCTGAA TCCTTTCTAT 1500
AGCACCACTT ATTGCAGCAG GTGTAGGCTC TGGTGTGGCC TGTGTCTGTG CTTCAATCTT 1560
TTAAAGCTTC TTTGGAAATA CACTGACTTG ATTGAAGTCT CTTGAAGATA GTAAACAGTA 1620
CTTACCTTTG ATCCCAATGA AATCGAGCAT TCAGTTGTA AAAGAATTCC GCCTATTCAT 1680
ACCATGTAAT GTAATTTTAC ACCCCAGTG CTGACACTTT GGAATATATT CAAGTAATAG 1740
ACTTTGGCCT CACCCTCTTG TGTACTGTAT TTTGTAATAG AAAATATTTT AAACTGTGCA 1800
TATGATTATT ACATTATGAA AGAGACATTC TGCTGATCTT CAAATGTAAG AAAATGAGGA 1860
GTGCGTGTGC TTTTATAAAT ACAAGTGATT GCAAATTAGT GCAGGTGTCC TTAAAAAAAA 1920
AAAAAAAAAG TAATATAAAA AGGACCAGGT GTTTTACAAG TGAAATACAT TCCTATTTGG 1980
TAAACAGTTA CATTTTTATG AAGATTACCA GCGCTGCTGA CTTTCTAAAC ATAAGGCTGT 2040
ATTGTCTTCC TGTACCATTG CATTTCCTCA TTCCCAATTT GCACAAGGAT GTCTGGGTAA 2100
ACTATTCAAG AAATGGCTTT GAAATACAGC ATGGGAGCTT GTCTGAGTTG GAATGCAGAG 2160
TTGCACTGCA AAATGTCAGG AAATGGATGT CTCTCAGAAT GCCCAACTCC AAAGGATTTT 2220
ATATGTGTAT ATAGTAAGCA GTTTCCTGAT TCCAGCAGGC CAAAGAGTCT GCTGAATGTT 2280
GTGTTGCCGG AGACCTGTAT TTCTCAACAA GGTAAGATGG TATCCTAGCA ACTGCGGATT 2340
TTAATACATT TTCAGCAGAA GTACTTAGTT AATCTCTACC TTTAGGGATC GTTTCATCAT 2400
TTTTAGATGT TATACTTGAA ATACTGCATA ACTTTTAGCT TTCATGGGTT CCTTTTTTTC 2460
AGCCTTTAGG AGACTGTTAA GCAATTTGCT GTCCAACTTT TGTGTTGGTC TTAAACTGCA 2520
ATAGTAGTTT ACCTTGTATT GAAGAAATAA AGACCATTTT TATATTAAAA AATACTTTTG 2580
TCTGTCTTCA TTTTGACTTG TCTGATATCC TTGCAGTGCC CATTATGTCA GTTCTGTCAG 2640
ATATTCAGAC ATCAAAACTT AACGTGAGCT CAGTGGAGTT ACAGCTGCGG TTTTGATGCT 2700
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
CCCGATTCCT TGAAAGGGCT CCAGCTTTAA TGCTTCCAAA TTGAAGGTGG CAGGCAACTT 3120
```

*FIG. 3a*

```
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTTCCC TCCACGTAAA 3540
GCAGTCTGGG AAAGTAGCAC CCCTTGAGCA GAGACAAGGA AATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAATGGG TTTTAAAAAA GAAAACACAA 3900
AGGCAAAACC GGCTGCCCCA TGAGAAGAAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GGCACTATTT TGGTTTGTAA 4140
AGCCTGTACT TCAAATATAT ATTTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TGAGAAGAT GGCAGTTGCT 4500
TCTTTCCCTT TTTCCTGCTA AGTAAGGATT TTCCTGGC TTTGACACCT CACGAAATAG 4560
TCTTCCTGCC TTACATTCTG GGCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTA AATACATAAA 5280
CTACTTCAAA TGAGGTCGGA GAAGGTCAGT GTTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAAATTC TTTCTTTTCC 5520
TGTCATGTGG GATCCCTACT GTGCCCTCCT GGTTTTACGT TACCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTT CGTTCTTCCA TATCAGTCTT CTCTATGACA ATTCACATCC 6180
ACCACAGCAA ATTAAGGTG AAGGAGGCTG GTGGGATGAA GAGGGTCTTC TAGCTTTACG 6240
TTCTTCCTTG CAAGGCCACA GGAAAATGCT GAGAGCTGTA GAATACAGCC TGGGGTAAGA 6300
AGTTCAGTCT CCTGCTGGGA CAGCTAACCG CATCTTATAA CCCCTTCTGA GACTCATCTT 6360
```

FIG. 3b

```
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT TCCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GGCTGCTTGC CACCCACTGG 6660
CTCAGGCTGC CCAGGGCCCC ATCCAGCCTG GCCTTGAGCA CCTCCAGGGA TGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CCAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGACAAT CGCTTACCCC TCCCTGCTGG CTGCCCCTGT TTTGATGCAG 7140
CCCAGGGTAC TGTTGGCCTT TCAGGCTCCC AGACCCCTTG CTGATTTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAG TTCGTCACTG ACAAGTTTAT 7860
GCATTTTATT ACTTCTATTA TGTACTTACT TTGACATAAC ACAGACACGC ACATATTTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA CAAGAAAAGA GATTCCTTTT TTATTACTTC 8040
TCTTCAGCCA ATAAACAAAA TGTGAGAAGC CCAAACAAGA ACTTGTGGGG CAGGCTGCCA 8100
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
GTATGAACTC AGGTCTCTCG GGCTACTGGC ATGGATTGAT TACATACAAC TGTAATTTTA 9600
```

*FIG. 3c*

```
GCAGTGATTT AGGGTTTATG AGTACTTTTG CAGTAAATCA TAGGGTTAGT AATGTTAATC  9660
TCAGGGAAAA AAAAAAAAAG CCAACCCTGA CAGACATCCC AGCTCAGGTG GAAATCAAGG  9720
ATCACAGCTC AGTGCGGTCC CAGAGAACAC AGGGACTCTT CTCTTAGGAC CTTTATGTAC  9780
AGGGCCTCAA GATAACTGAT GTTAGTCAGA AGACTTTCCA TTCTGGCCAC AGTTCAGCTG  9840
AGGCAATCCT GGAATTTTCT CTCCGCTGCA CAGTTCCAGT CATCCCAGTT TGTACAGTTC  9900
TGGCACTTTT TGGGTCAGGC CGTGATCCAA GGAGCAGAAG TTCCAGCTAT GGTCAGGGAG  9960
TGCCTGACCG TCCCAACTCA CTGCACTCAA ACAAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TTGAATGTCA TTAAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
CTCTCTGGGC AGCCTGTGCC AGCACCTCAC CACCCTCTCT GTGAAGAACT TTTCCCTGAC 10800
ATCCAATCTA AGCCTTCCCT CCTTGAGGTT AGATCCACTC CCCCTTGTGC TATCACTGTC 10860
TACTCTTGTA AAAGTTGAT TCTCCTCCTT TTTGGAAGGT TGCAATGAGG CTCCTTGCA 10920
GCCTTCTTCT CTTCTGCAGG ATGAACAAGC CCAGCTCCCT CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTTGA CAACTGTAGA ACAGAGGAAT CAAAAGGGGG 11820
TGGGAGGAAG TTAAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGGTGCGA TCTGCCTCAG ACCCACAGCC TGGGCAGCAG GAGGACCCTG ATGCTGCTGG 12000
CTCAGATGAG GAGAATCAGC CTGTTTAGCT GCCTGAAGGA TAGGCACGAT TTTGGCTTTC 12060
CTCAAGAGGA GTTTGGCAAC CAGTTTCAGA AGGCTGAGAC CATCCCTGTG CTGCACGAGA 12120
TGATCCAGCA GATCTTTAAC CTGTTTAGCA CCAAGGATAG CAGCGCTGCT TGGGATGAGA 12180
CCCTGCTGGA TAAGTTTTAC ACCGAGCTGT ACCAGCAGCT GAACGATCTG GAGGCTTGCG 12240
TGATCCAGGG CGTGGGCGTG ACCGAGACCC CTCTGATGAA GGAGGATAGC ATCCTGGCTG 12300
TGAGGAAGTA CTTTCAGAGG ATCACCCTGT ACCTGAAGGA GAAGAAGTAC AGCCCCTGCG 12360
CTTGGGAAGT CGTGAGGGCT GAGATCATGA GGAGCTTTAG CCTGAGCACC AACCTGCAAG 12420
AGAGCTTGAG GTCTAAGGAG TAAAAAGTCT AGAGTCGGGG CGGCCGGCCG CTTCGAGCAG 12480
ACATGATAAG ATACATTGAT GAGTTTGGAC AAACCACAAC TAGAATGCAG TGAAAAAAAT 12540
GCTTTATTTG TGAAATTTGT GATGCTATTG CTTTATTTGT AACCATTATA AGCTGCAATA 12600
AACAAGTTAA CAACAACAAT TGCATTCATT TTATGTTTCA GGTTCAGGGG GAGGTGTGGG 12660
AGGTTTTTTA AAGCAAGTAA AACCTCTACA AATGTGGTAA AATCGATAAG GATCCGTCGA 12720
GCGGCCGC                                                          12728
```

*FIG. 3d*

SEQ ID NO: 66

```
TGCGATCTGC CTCAGACCCA CAGCCTGGGC AGCAGGAGGA CCCTGATGCT GCTGGCTCAG   60
ATGAGGAGAA TCAGCCTGTT TAGCTGCCTG AAGGATAGGC ACGATTTTGG CTTTCCTCAA  120
GAGGAGTTTG GCAACCAGTT TCAGAAGGCT GAGACCATCC CTGTGCTGCA CGAGATGATC  180
CAGCAGATCT TTAACCTGTT TAGCACCAAG GATAGCAGCG CTGCTTGGGA TGAGACCCTG  240
CTGGATAAGT TTTACACCGA GCTGTACCAG CAGCTGAACG ATCTGGAGGC TTGCGTGATC  300
CAGGGCGTGG GCGTGACCGA GACCCCTCTG ATGAAGGAGG ATAGCATCCT GGCTGTGAGG  360
AAGTACTTTC AGAGGATCAC CCTGTACCTG AAGGAGAAGA AGTACAGCCC CTGCGCTTGG  420
GAAGTCGTGA GGGCTGAGAT CATGAGGAGC TTTAGCCTGA GCACCAACCT GCAAGAGAGC  480
TTGAGGTCTA AGGAGTAA 498
```

*Fig. 4*

SEQ ID NO: 67

```
TGCCGCCTTC TTTGATATTC ACTCTGTTGT ATTTCATCTC TTCTTGCCGA TGAAAGGATA 60
TAACAGTCTG TATAACAGTC TGTGAGGAAA TACTTGGTAT TTCTTCTGAT CAGTGTTTTT 120
ATAAGTAATG TTGAATATTG GATAAGGCTG TGTGTCCTTT GTCTTGGGAG ACAAAGCCCA 180
CAGCAGGTGG TGGTTGGGGT GGTGGCAGCT CAGTGACAGG AGAGGTTTTT TTGCCTGTTT 240
TTTTTTTTTT TTTTTTTTTT AAGTAAGGTG TTCTTTTTTC TTAGTAAATT TTCTACTGGA 300
CTGTATGTTT TGACAGGTCA GAAACATTTC TTCAAAAGAA GAACCTTTTG GAAACTGTAC 360
AGCCCTTTTC TTTCATTCCC TTTTTGCTTT CTGTGCCAAT GCCTTTGGTT CTGATTGCAT 420
TATGGAAAAC GTTGATCGGA ACTTGAGGTT TTTATTTATA GTGTGGCTTG AAAGCTTGGA 480
TAGCTGTTGT TACACGAGAT ACCTTATTAA GTTTAGGCCA GCTTGATGCT TTATTTTTTC 540
CCTTTGAAGT AGTGAGCGTT CTCTGGTTTT TTTCCTTTGA AACTGGTGAG GCTTAGATTT 600
TTCTAATGGG ATTTTTTACC TGATGATCTA GTTGCATACC CAAATGCTTG TAAATGTTTT 660
CCTAGTTAAC ATGTTGATAA CTTCGGATTT ACATGTTGTA TATACTTGTC ATCTGTGTTT 720
CTAGTAAAAA TATATGGCAT TTATAGAAAT ACGTAATTCC TGATTTCCTT TTTTTTTATC 780
TCTATGCTCT GTGTGTACAG GTCAAACAGA CTTCACTCCT ATTTTTATTT ATAGAATTTT 840
ATATGCAGTC TGTCGTTGGT TCTTGTGTTG TAAGGATACA GCCTTAAATT TCCTAGAGCG 900
ATGCTCAGTA AGGCGGGTTG TCACATGGGT TCAAATGTAA AACGGGCACG TTTGGCTGCT 960
GCCTTCCCGA GATCCAGGAC ACTAAACTGC TTCTGCACTG AGGTATAAAT CGCTTCAGAT 1020
CCCAGGGAAG TGCAGATCCA CGTGCATATT CTTAAAGAAG AATGAATACT TTCTAAAATA 1080
TTTTGGCATA GGAAGCAAGC TGCATGGATT TGTTTGGGAC TTAAATTATT TTGGTAACGG 1140
AGTGCATAGG TTTTAAACAC AGTTGCAGCA TGCTAACGAG TCACAGCGTT TATGCAGAAG 1200
TGATGCCTGG ATGCCTGTTG CAGCTGTTTA CGGCACTGCC TTGCAGTGAG CATTGCAGAT 1260
AGGGGTGGGG TGCTTTGTGT CGTGTTCCCA CACGCTGCCA CACAGCCACC TCCCGGAACA 1320
CATCTCACCT GCTGGGTACT TTTCAAACCA TCTTAGCAGT AGTAGATGAG TTACTATGAA 1380
ACAGAGAAGT TCCTCAGTTG GATATTCTCA TGGGATGTCT TTTTTCCCAT GTTGGGCAAA 1440
GTATGATAAA GCATCTCTAT TTGTAAATTA TGCACTTGTT AGTTCCTGAA TCCTTTCTAT 1500
AGCACCACTT ATTGCAGCAG GTGTAGGCTC TGGTGTGGCC TGTGTCTGTG CTTCAATCTT 1560
TTAAAGCTTC TTTGGAAATA CACTGACTTG ATTGAAGTCT CTTGAAGATA GTAAACAGTA 1620
CTTACCTTTG ATCCCAATGA AATCGAGCAT TTCAGTTGTA AAAGAATTCC GCCTATTCAT 1680
ACCATGTAAT GTAATTTTAC ACCCCCAGTG CTGACACTTT GGAATATATT CAAGTAATAG 1740
ACTTTGGCCT CACCCTCTTG TGTACTGTAT TTTGTAATAG AAAATATTTT AAACTGTGCA 1800
TATGATTATT ACATTATGAA AGAGACATTC TGCTGATCTT CAAATGTAAG AAAATGAGGA 1860
GTGCGTGTGC TTTTATAAAT ACAAGTGATT GCAAATTAGT GCAGGTGTCC TTAAAAAAAA 1920
AAAAAAAAAG TAATATAAAA AGGACCAGGT GTTTTACAAG TGAAATACAT TCCTATTTGG 1980
TAAACAGTTA CATTTTTATG AAGATTACCA GCGCTGCTGA CTTTCTAAAC ATAAGGCTGT 2040
ATTGTCTTCC TGTACCATTG CATTTCCTCA TTCCCAATTT GCACAAGGAT GTCTGGGTAA 2100
ACTATTCAAG AAATGGCTTT GAAATACAGC ATGGGAGCTT GTCTGAGTTG GAATGCAGAG 2160
TTGCACTGCA AAATGTCAGG AAATGATGT CTCTCAGAAT GCCCAACTCC AAAGGATTTT 2220
ATATGTGTAT ATAGTAAGCA GTTTCCTGAT TCCAGCAGGC CAAAGAGTCT GCTGAATGTT 2280
GTGTTGCCGG AGACCTGTAT TTCTCAACAA GGTAAGATGG TATCCTAGCA ACTGCGGATT 2340
TTAATACATT TTCAGCAGAA GTACTTAGTT AATCTCTACC TTTAGGGATC GTTTCATCAT 2400
TTTTAGATGT TATACTTGAA ATACTGCATA ACTTTTAGCT TTCATGGGTT CCTTTTTTTC 2460
AGCCTTTAGG AGACTGTTAA GCAATTTGCT GTCCAACTTT TGTGTTGGTC TTAAACTGCA 2520
ATAGTAGTTT ACCTTGTATT GAAGAAATAA AGACCATTTT TATATTAAAA AATACTTTTG 2580
TCTGTCTTCA TTTTGACTTG TCTGATATCC TTGCAGTGCC CATTATGTCA GTTCTGTCAG 2640
ATATTCAGAC ATCAAAACTT AACGTGAGCT CAGTGGAGTT ACAGCTGCGG TTTTGATGCT 2700
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
```

FIG. 5a

```
CCCGATTCCT TGAAAGGGCT CCAGCTTTAA TGCTTCCAAA TTGAAGGTGG CAGGCAACTT 3120
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTTCCC TCCACGTAAA 3540
GCAGTCTGGG AAAGTAGCAC CCCTTGAGCA GAGACAAGGA AATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAAATGGG TTTTAAAAAA GAAAACACAA 3900
AGGCAAAACC GGCTGCCCCA TGAGAAGAAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GGCACTATTT TGGTTTGTAA 4140
AGCCTGTACT TCAAATATAT ATTTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCAGC CGCCCAAGT TGAGAAGAT GGCAGTTGCT 4500
TCTTTCCCTT TTTCCTGCTA AGTAAGGATT TTCTCCTGGC TTTGACACCT CACGAAATAG 4560
TCTTCCTGCC TTACATTCTG GGCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTA AATACATAAA 5280
CTACTTCAAA TGAGGTCGGA GAAGGTCAGT GTTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
CATAGCGGCT GAAGCTCCCC CCTGGCTGCC TGCCATCTCA GCTGGAGTGC AGTGCATTT 5460
CCTTGGGGTT TCTCTCACAG CAGTAATGGG ACAATACTTC ACAAAATTC TTTCTTTTCC 5520
TGTCATGTGG GATCCCTACT GTGCCCTCCT GGTTTTACGT TACCCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAAGGTG AAGGAGGCTG GTGGGATGAA GAGGGTCTTC TAGCTTTACG 6240
TTCTTCCTTG CAAGGCCACA GGAAAATGCT GAGAGCTGTA GAATACAGCC TGGGGTAAGA 6300
```

FIG. 5b

```
AGTTCAGTCT CCTGCTGGGA CAGCTAACCG CATCTTATAA CCCCTTCTGA GACTCATCTT 6360
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT TCCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GGCTGCTTGC CACCCACTGG 6660
CTCAGGCTGC CCAGGGCCCC ATCCAGCCTG GCCTTGAGCA CCTCCAGGGA TGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGACAAT CGCTTACCCC TCCCTGCTGG CTGCCCCTGT TTTGATGCAG 7140
CCCAGGGTAC TGTTGGCCTT TCAGGCTCCC AGACCCTTG CTGATTTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTTATT ACTTCTATTA TGTACTTACT TTGACATAAC ACAGACACGC ACATATTTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA CAAGAAAAGA GATTCCTTTT TTATTACTTC 8040
TCTTCAGCCA ATAAACAAAA TGTGAGAAGC CCAAACAAGA ACTTGTGGGG CAGGCTGCCA 8100
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
```

*FIG. 5c*

```
GTATGAACTC AGGTCTCTCG GGCTACTGGC ATGGATTGAT TACATACAAC TGTAATTTTA 9600
GCAGTGATTT AGGGTTTATG AGTACTTTTG CAGTAAATCA TAGGGTTAGT AATGTTAATC 9660
TCAGGGAAAA AAAAAAAAAG CCAACCCTGA CAGACATCCC AGCTCAGGTG GAAATCAAGG 9720
ATCACAGCTC AGTGCGGTCC CAGAGAACAC AGGGACTCTT CTCTTAGGAC CTTTATGTAC 9780
AGGGCCTCAA GATAACTGAT GTTAGTCAGA AGACTTTCCA TTCTGGCCAC AGTTCAGCTG 9840
AGGCAATCCT GGAATTTTCT CTCCGCTGCA CAGTTCCAGT CATCCCAGTT TGTACAGTTC 9900
TGGCACTTTT TGGGTCAGGC CGTGATCCAA GGAGCAGAAG TTCCAGCTAT GGTCAGGGAG 9960
TGCCTGACCG TCCCAACTCA CTGCACTCAA ACAAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TGAATGTCA TTAAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
CTCTCTGGGC AGCCTGTGCC AGCACCTCAC CACCCTCTCT GTGAAGAACT TTTCCCTGAC 10800
ATCCAATCTA AGCTTCCCT CCTTGAGGTT AGATCCACTC CCCCTTGTGC TATCACTGTC 10860
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CCAGCTCCCT CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTTGA CAACTGTAGA ACAGAGGAAT CAAAAGGGGG 11820
TGGGAGGAAG TTAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGG                                                        11945
```

*FIG. 5d*

SEQ ID NO: 68

```
AAAGTCTAGAGTCGGGGCGGCCGGCCGCTTCGAGCAGACATGATAAGATACATTGATGAG    60
TTTGGACAAACCACAACTAGAATGCAGTGAAAAAAATGCTTTATTTGTGAAATTTGTGAT   120
GCTATTGCTTTATTTGTAACCATTATAAGCTGCAATAAACAAGTTAACAACAACAATTGC   180
ATTCATTTTATGTTTCAGGTTCAGGGGGAGGTGTGGGAGGTTTTTTAAAGCAAGTAAAAC   240
CTCTACAAATGTGGTAAAATCGATAAGGATCCGTCGAGCGGCCGC    285
```

FIG. 6

SEQ ID NO: 69

```
   1 CGCGTGGTAG GTGGCGGGGG GTTCCCAGGA GAGCCCCCAG CGCGGACGGC
  51 AGCGCCGTCA CTCACCGCTC CGTCTCCCTC CGCCCAGGGT CGCCTGGCGC
 101 AACCGCTGCA AGGGCACCGA CGTCCAGGCG TGGATCAGAG GCTGCCGGCT
 151 GTGAGGAGCT GCCGCGCCCG GCCCGCCCGC TGCACAGCCG GCCGCTTTGC
 201 GAGCGCGACG CTACCCGCTT GGCAGTTTTA AACGCATCCC TCATTAAAAC
 251 GACTATACGC AAACGCCTTC CCGTCGGTCC GCGTCTCTTT CCGCCGCCAG
 301 GGCGACACTC GCGGGGAGGG CGGGAAGGGG GCCGGGCGGG AGCCCGCGGC
 351 CAACCGTCGC CCCGTGACGG CACCGCCCCG CCCCGTGAC GCGGTGCGGG
 401 CGCCGGGGCC GTGGGGCTGA GCGCTGCGGC GGGGCCGGGC CGGGCCGGGG
 451 CGGGAGCTGA GCGCGGCGCG GCTGCGGGCG GCGCCCCTC CGGTGCAATA
 501 TGTTCAAGAG AATGGCTGAG TTCGGGCCTG ACTCCGGGG CAGGGTGAAG
 551 GTGCGGCGCG GGCGGAGGGA CGGGGCGGGC GCGGGCCGC CGGCGGGTG
 601 CCGGGGCCTC TGCCGGCCCG CCCGGCTCGG GCTGCTGCGG CGCTTACGGG
 651 CGCGCTTCTC GCCGCTGCCG CTTCTCTTCT CTCCCGCGCA AGGGCGTCAC
 701 CATCGTGAAG CCGGTAGTGT ACGGGAACGT GGCGCGGTAC TTCGGGAAGA
 751 AGAGGGAGGA GGACGGGCAC ACGCATCAGT GGACGGTTTA CGTGAAGCCC
 801 TACAGGAACG AGGTAGGGCC CGAGCGCGTC GGCCGCCGTT CTCGGAGCGC
 851 CGGAGCCGTC AGCGCCGCGC CTGGGTGCGC TGTGGACAC AGCGAGCTTC
 901 TCTCGTAGGA CATGTCCGCC TACGTGAAAA AAATCCAGTT CAAGCTGCAC
 951 GAGAGCTACG GAATCCTCT CCGAGGTGGG TGTTGCGTCG GGGGTTTGC
1001 TCCGCTCGGT CCCGCTGAGG CTCGTCGCCC TCATCTTTCT TTCGTGCCGC
1051 AGTCGTTACC AAACCGCCGT ACGAGATCAC CGAAACGGGC TGGGGCGAAT
1101 TTGAAATCAT CATCAAGATA TTTTTCATTG ATCCAAACGA GCGACCCGTA
1151 AGTACGCTCA GCTTCTCGTA GTGCTTCCCC CGTCCTGGCG GCCCGGGGCT
1201 GGGCTGCTCG CTGCTGCCGG TCACAGTCCC GCCAGCCGCG GAGCTGACTG
1251 AGCTCCCTTT CCCGGGACGT GTGCTCTGTG TTCGGTCAGC GAGGCTATCG
1301 GGAGGGCTTT GGCTGCATTT GGCTTCTCTG GCGCTTAGCG CAGGAGCACG
1351 TTGTGCTACG CCTGAACTAC AGCTGTGAGA AGGCCGTGGA AACCGCTCTC
1401 AAACTGATTT ATTGGCGAAA TGGCTCTAAA CTAAATCGTC TCCTCTCTTT
1451 GGAAATGCTT TAGAGAAGGT CTCTGTGGTA GTTCTTATGC ATCTATCCTA
1501 AAGCACTTGG CCAGACAATT TAAAGACATC AAGCAGCATT TATAGCAGGC
1551 ACGTTTAATA ACGAATACTG AATTTAAGTA ACTCTGCTCA CGTTGTATGA
1601 CGTTTATTTT CGTATTCCTG AAAGCCATTA AAATCCTGTG CAGTTGTTTA
1651 GTAAGAACAG CTGCCACTGT TTTGTATCTA GGAGATAACT GGTGTTTCCC
1701 TACAGTTCTC AAGCTGATAA AACTCTGTCT TTGTATCTAG GTAACCCTGT
1751 ATCACTTGCT GAAGCTTTTT CAGTCTGACA CCAATGCAAT CCTGGGAAAG
1801 AAAACTGTAG TTTCTGAATT CTATGATGAA ATGGTATGAA AATTTTAATG
1851 TCAACCGAGC CTGACTTTAT TTAAAAAAAA TTATTGATGG TGCTGTGTAT
1901 TTTGGTCCTT CCTTAGATAT TTCAAGATCC TACTGCCATG ATGCAGCAAC
1951 TGCTAACGAC GTCCCGTCAG CTGACACTTG GTGCTTACAA GCATGAAACA
2001 GAGTGTAAGT GCAAAATGAG GATACCTTCG CCGACCGTCA TTCACTACTA
2051 ATGTTTTCTG TGGGATGTGA TCGTACAGTG AGTTTGGCTG TGTGAAATTT
2101 GAATAGCTTG GTATTGGCAG TGATGACGTG ATCGATGCCT TGCTTATCAT
2151 GTTTGAAATG AAGTAGAATA AATGCAGCCT GCTTTATTTG AGATAGTTTG
2201 GTTCATTTTA TGGAATGCAA GCAAAGATTA TACTTCCTCA CTGAATTGCA
```

*Fig. 7a*

```
2251  CTGTCCAAAG GTGTGAAATG TGTGGGGATC TGGAGGACCG TGACCGAGGG
2301  ACATTGGATC GCTATCTCCC ATTTCTTTTG CTGTTACCAG TTCAGATTTT
2351  CTTTTCACCT AGTCTTTAAT TCCCAGGGTT TTGTTTTTTC CTTGGTCATA
2401  GTTTTTGTTT TTCACTCTGG CAAATGATGT TGTGAATTAC ACTGCTTCAG
2451  CCACAAAACT GATGGACTGA ATGAGGTCAT CAAACAAACT TTTCTTCTTC
2501  CGTATTTCCT TTTTTTTCCC CCACTTATCA TTTTTACTGC TGTTGTTGAG
2551  TCTGTAAGGC TAAAAGTAAC TGTTTTGTGC TTTTTCAGGA CGTGTGCTTT
2601  CCAAATTACT GCCACATATA TAAAGAAAGG TTGGAATTTT AAAGATAATT
2651  CATGTTTCTT CTTCTTTTTT GCCACCACAG TTGCAGATCT TGAAGTAAAA
2701  ACCAGGGAAA AGCTGGAAGC TGCCAAAAAG AAAACCAGTT TTGAAATTGC
2751  TGAGCTTAAA GAAAGGTTAA AAGCAAGTCG TGAAACCATC AACTGCTTAA
2801  AGAGTGAAAT CAGAAAACTC GAAGAGGATG ATCAGTCTAA AGATATGTGA
2851  TGAGTGTTGA CTTGGCAGGG AGCCTATAAT GAGAATGAAA GGACTTCAGT
2901  CGTGGAGTTG TATGCGTTCT CTCCAATTCT GTAACGGAGA CTGTATGAAT
2951  TTCATTTGCA AATCACTGCA GTGTGTGACA ACTGACTTTT TATAAATGGC
3001  AGAAAACAAG AATGAATGTA TCCTCATTTT ATAGTTAAAA TCTATGGGTA
3051  TGTACTGGTT TATTTCAAGG AGAATGGATC GTAGAGACTT GGAGGCCAGA
3101  TTGCTGCTTG TATTGACTGC ATTTGAGTGG TGTAGGAACA TTTTGTCTAT
3151  GGTCCCGTGT TAGTTTACAG AATGCCACTG TTCACTGTTT TGTTTTGTAT
3201  TTTACTTTTT CTACTGCAAC GTCAAGGTTT TAAAAGTTGA AAATAAAACA
3251  TGCAGGTTTT TTTTAAATAT TTTTTTGTCT CTATCCAGTT TGGGCTTCAA
3301  GTATTATTGT TAACAGCAAG TCCTGATTTA AGTCAGAGGC TGAAGTGTAA
3351  TGGTATTCAA GATGCTTAAG TCTGTTGTCA GCAAAACAAA AGAGAAAACT
3401  TCATAAAATC AGGAAGTTGG CATTTCTAAT AACTTCTTTA TCAACAGATA
3451  AGAGTTTCTA GCCCTGCATC TACTTTCACT TATGTAGTTG ATGCCTTTAT
3501  ATTTTGTGTG TTTGGATGCA GGAAGTGATT CCTACTCTGT TATGTAGATA
3551  TTCTATTTAA CACTTGTACT CTGCTGTGCT TAGCCTTTCC CCATGAAAAT
3601  TCAGCGGCTG TAAATCCCCC TCTTCTTTTG TAGCCTCATA CAGATGGCAG
3651  ACCCTCAGGC TTATAAAGGC TTGGGCATCT TCTTTACTGC TTTGAGATTC
3701  TGTGTTGCAG TAACCTCTGC CAGAGAGGAG AAAAGCCCCA CAAACCTCAT
3751  CCCCTTCTTC TATAGCAATC AGTATTACTA ATGCTTTGAG AACAGAGCAC
3801  TGGTTTGAAA CGTTTGATAA TTAGCATTTA ACATGGCTTG GTAAAGATGC
3851  AGAACTGAAA CAGCTGTGAC AGTATGAACT CAGTATGGAG ACTTCATTAA
3901  GACAAACAGC TGTTAAAATC AGGCATGTTT CATTGAGGAG GACGGGGCAA
3951  CTTGCACCAG TGGTGCCCAC ACAAATCCTT CCTGGCGCTG CAGACCAATT
4001  TTTCTGGCAT TCTGACTGCC GTTGCTGCTG GTCACAGAGA GCAACTATTT
4051  TTATCAGCCA CAGGCAATTT GCTTGTAGTA TTTTCCAAGT GTTGTAGGTA
4101  AGTATAAATG CATCGGCTCC AGAGCACTTT GAGTATACTT ATTAAAAACA
4151  TAAATGAAAG ACAAATTAGC TTTGCTTGGG TGCACAGAAC ATTTTTAGTT
4201  CCAGCCTGCT TTTTGGTAGA AGCCCTCTTC TGAGGCTAGA ACTGACTTTG
4251  ACAAGTAGAG AAACTGGCAA CGGAGCTATT GCTATCGAAG GATCCTTGTT
4301  AACAAAGTTA ATCGTCTTTT AAGGTTTGGT TTATTCATTA AATTTGCTTT
4351  TAAGCTGTAG CTGAAAAAGA ACGTGCTGTC TTCCATGCAC CAGGTGGCAG
4401  CTCTGTGCAA AGTGCTCTCT GGTCTCACCA GCCTTTTAAT TGCCGGGATT
4451  CTGGCACGTC TGAGAGGGCT CAGACTGGCT TCGTTTGTTT GAACAGCGTG
4501  TACTGCTTTC TGTAGACATG GCCGGTTTCT CTCCTGCAGC TTATGAAACT
4551  GTTCACACTG AACACACTGG AACAGGTTGC CAAGGAGGC CGTGGATGCC
4601  CCATCCCTGG AGGCATTCAA GGCCAGGCTG GATGTGGCTC TGGGCAGCCT
```

*Fig. 7b*

```
4651  GGTCTGGTGG TTGGCGATCC TGCACATAGC AGCGGGGTTG AAACTCGATG
4701  ATCACTGTGG TCCTTTTCAA CCCAGGCTAT TCTATGATTC TATGATTCAA
4751  CAGCAAATCA TATGTACTGA GAGAGGAAAC AAACACAAGT GCTACTGTTT
4801  GCAAGTTTTG TTCATTTGGT AAAAGAGTCA GGTTTTAAAA TTCAAAATCT
4851  GTCTGGTTTT GGTGTTTTTT TTTTTTTATT TATTATTTCT TTGGGGTTCT
4901  TTTTGATGCT TTATCTTTCT CTGCCAGGAC TGTGTGACAA TGGGAACGAA
4951  AAAGAACATG CCAGGCACTG TCCTGGATTG CACACGCTGG TTGCACTCAG
5001  TAGCAGGCTC AGAACTGCCA GTCTTTCCAC AGTATTACTT TCTAAACCTA
5051  ATTTTAATAG CGTTAGTAGA CTTCCATCAC TGGGCAGTGC TTAGTGAATG
5101  CTCTGTGTGA ACGTTTTACT TATAAGCATG TTGGAAGTTT TGATGTTCCT
5151  GGATGCAGTA GGGAAGGACA GATTAGCTAT GTGAAAAGTA GATTCTGAGT
5201  ATCGGGGTTA CAAAAAGTAT AGAAACGATG AGAAATTCTT GTTGTAACTA
5251  ATTGGAATTT CTTTAAGCGT TCACTTATGC TACATTCATA GTATTTCCAT
5301  TTAAAAGTAG GAAAAGGTAA AACGTGAAAT CGTGTGATTT TCGGATGGAA
5351  CACCGCCTTC CTATGCACCT GACCAACTTC CAGAGGAAAA GCCTATTGAA
5401  AGCCGAGATT AAGCCACCAA AAGAACTCAT TTGCATTGGA ATATGTAGTA
5451  TTTGCCCTCT TCCTCCCGGG TAATTACTAT ACTTTATAGG GTGCTTATAT
5501  GTTAAATGAG TGGCTGGCAC TTTTTATTCT CACAGCTGTG GGGAATTCTG
5551  TCCTCTAGGA CAGAAACAAT TTTAATCTGT TCCACTGGTG ACTGCTTTGT
5601  CAGCACTTCC ACCTGAAGAG ATCAATACAC TCTTCAATGT CTAGTTCTGC
5651  AACACTTGGC AAACCTCACA TCTTATTTCA TACTCTCTTC ATGCCTATGC
5701  TTATTAAAGC AATAATCTGG GTAATTTTTG TTTTAATCAC TGTCCTGACC
5751  CCAGTGATGA CCGTGTCCCA CCTAAAGCTC AATTCAGGTC CTGAATCTCT
5801  TCAACTCTCT ATAGCTAACA TGAAGAATCT TCAAAAGTTA GGTCTGAGGG
5851  ACTTAAGGCT AACTGTAGAT GTTGTTGCCT GGTTTCTGTG CTGAAGGCCG
5901  TGTAGTAGTT AGAGCATTCA ACCTCTAG
```

*Fig. 7c*

SEQ ID NO: 74

```
   1 TGCCGCCTTCTTTGATATTCACTCTGTTGTATTTCATCTCTTCTTGCCGA
  51 TGAAAGGATATAACAGTCTGTATAACAGTCTGTGAGGAAATACTTGGTAT
 101 TTCTTCTGATCAGTGTTTTTATAAGTAATGTTGAATATTGGATAAGGCTG
 151 TGTGTCCTTTGTCTTGGGAGACAAAGCCCACAGCAGGTGGTGGTTGGGGT
 201 GGTGGCAGCTCAGTGACAGGAGAGGTTTTTTGCCTGTTTTTTTTTTTT
 251 TTTTTTTTTAAGTAAGGTGTTCTTTTTTCTTAGTAAATTTTCTACTGGA
 301 CTGTATGTTTTGACAGGTCAGAAACATTTCTTCAAAAGAAGAACCTTTTG
 351 GAAACTGTACAGCCCTTTTCTTTCATTCCCTTTTTGCTTTCTGTGCCAAT
 401 GCCTTTGGTTCTGATTGCATTATGGAAAACGTTGATCGGAACTTGAGGTT
 451 TTTATTTATAGTGTGGCTTGAAAGCTTGGATAGCTGTTGTTACACGAGAT
 501 ACCTTATTAAGTTTAGGCCAGCTTGATGCTTTATTTTTTCCCTTTGAAGT
 551 AGTGAGCGTTCTCTGGTTTTTTTCCTTTGAAACTGGTGAGGCTTAGATTT
 601 TTCTAATGGATTTTTTACCTGATGATCTAGTTGCATACCCAAATGCTTG
 651 TAAATGTTTTCCTAGTTAACATGTTGATAACTTCGGATTTACATGTTGTA
 701 TATACTTGTCATCTGTGTTTCTAGTAAAATATATGGCATTTATAGAAAT
 751 ACGTAATTCCTGATTTCCTTTTTTTTATCTCTATGCTCTGTGTGTACAG
 801 GTCAAACAGACTTCACTCCTATTTTATTTATAGAATTTTATATGCAGTC
 851 TGTCGTTGGTTCTTGTGTTGTAAGGATACAGCCTTAAATTTCCTAGAGCG
 901 ATGCTCAGTAAGGCGGGTTGTCACATGGGTTCAAATGTAAAACGGGCACG
 951 TTTGGCTGCTGCCTTCCCGAGATCCAGGACACTAAACTGCTTCTGCACTG
1001 AGGTATAAATCGCTTCAGATCCCAGGGAAGTGCAGATCCACGTGCATATT
1051 CTTAAAGAAGAATGAATACTTTCTAAATATTTTGGCATAGGAAGCAAGC
1101 TGCATGGATTTGTTTGGGACTTAAATTATTTTGGTAACGGAGTGCATAGG
1151 TTTTAAACACAGTTGCAGCATGCTAACGAGTCACAGCGTTTATGCAGAAG
1201 TGATGCCTGGATGCCTGTTGCAGCTGTTTACGGCACTGCCTTGCAGTGAG
1251 CATTGCAGATAGGGGTGGGGTGCTTTGTGTCGTGTTCCCACACGCTGCCA
1301 CACAGCCACCTCCCGGAACACATCTCACCTGCTGGGTACTTTTCAAACCA
1351 TCTTAGCAGTAGTAGATGAGTTACTATGAAACAGAGAAGTTCCTCAGTTG
1401 GATATTCTCATGGGATGTCTTTTTTCCCATGTTGGGCAAAGTATGATAAA
1451 GCATCTCTATTTGTAAATTATGCACTTGTTAGTTCCTGAATCCTTTCTAT
1501 AGCACCACTTATTGCAGCAGGTGTAGGCTCTGGTGTGGCCTGTGTCTGTG
1551 CTTCAATCTTTTAAAGCTTCTTTGGAAATACACTGACTTGATTGAAGTCT
1601 CTTGAAGATAGTAAACAGTACTTACCTTTGATCCCAATGAAATCGAGCAT
1651 TTCAGTTGTAAAAGAATTCCGCCTATTCATACCATGTAATGTAATTTTAC
1701 ACCCCAGTGCTGACACTTTGGAATATATTCAAGTAATAGACTTTGGCCT
1751 CACCCTCTTGTGTACTGTATTTGTAATAGAAATATTTTAAACTGTGCA
1801 TATGATTATTACATTATGAAAGAGACATTCTGCTGATCTTCAAATGTAAG
1851 AAAATGAGGAGTGCGTGTGCTTTTATAAATACAAGTGATTGCAAATTAGT
1901 GCAGGTGTCCTTAAAAAAAAAAAAAAAAGTAATATAAAAAGGACCAGGT
1951 GTTTTACAAGTGAAATACATTCCTATTTGGTAAACAGTTACATTTTTATG
2001 AAGATTACCAGCGCTGCTGACTTTCTAAACATAAGGCTGTATTGTCTTCC
2051 TGTACCATTGCATTTCCTCATTCCCAATTTGCACAAGGATGTCTGGGTAA
```

*Fig. 8a*

```
2101  ACTATTCAAGAAATGGCTTTGAAATACAGCATGGGAGCTTGTCTGAGTTG
2151  GAATGCAGAGTTGCACTGCAAATGTCAGGAAATGGATGTCTCTCAGAAT
2201  GCCCAACTCCAAAGGATTTTATATGTGTATATAGTAAGCAGTTTCCTGAT
2251  TCCAGCAGGCCAAAGAGTCTGCTGAATGTTGTGTTGCCGGAGACCTGTAT
2301  TTCTCAACAAGGTAAGATGGTATCCTAGCAACTGCGGATTTTAATACATT
2351  TTCAGCAGAAGTACTTAGTTAATCTCTACCTTTAGGGATCGTTTCATCAT
2401  TTTTAGATGTTATACTTGAAATACTGCATAACTTTTAGCTTTCATGGGTT
2451  CCTTTTTTTCAGCCTTTAGGAGACTGTTAAGCAATTTGCTGTCCAACTTT
2501  TGTGTTGGTCTTAAACTGCAATAGTAGTTTACCTTGTATTGAAGAAATAA
2551  AGACCATTTTTATATTAAAAAATACTTTTGTCTGTCTTCATTTTGACTTG
2601  TCTGATATCCTTGCAGTGCCCATTATGTCAGTTCTGTCAGATATTCAGAC
2651  ATCAAAACTTAACGTGAGCTCAGTGGAGTTACAGCTGCGGTTTTGATGCT
2701  GTTATTATTTCTGAAACTAGAAATGATGTTGTCTTCATCTGCTCATCAAA
2751  CACTTCATGCAGAGTGTAAGGCTAGTGAGAAATGCATACATTTATTGATA
2801  CTTTTTAAAGTCAACTTTTATCAGATTTTTTTTCATTTGGAAATATA
2851  TTGTTTCTAGACTGCATAGCTTCTGAATCTGAAATGCAGTCTGATTGGC
2901  ATGAAGAAGCACAGCACTCTTCATCTTACTTAAACTTCATTTTGGAATGA
2951  AGGAAGTTAAGCAAGGGCACAGGTCCATGAAATAGAGACAGTGCGCTCAG
3001  GAGAAAGTGAACCTGGATTTCTTTGGCTAGTGTTCTAAATCTGTAGTGAG
3051  GAAAGTAACACCCGATTCCTTGAAAGGGCTCCAGCTTTAATGCTTCCAAA
3101  TTGAAGGTGGCAGGCAACTTGGCCACTGGTTATTTACTGCATTATGTCTC
3151  AGTTTCGCAGCTAACCTGGCTTCTCCACTATTGAGCATGGACTATAGCCT
3201  GGCTTCAGAGGCCAGGTGAAGGTTGGGATGGGTGGAAGGAGTGCTGGGCT
3251  GTGGCTGGGGGACTGTGGGACTCCAAGCTGAGCTTGGGGTGGGCAGCA
3301  CAGGGAAAAGTGTGGGTAACTATTTTAAGTACTGTGTTGCAAACGTCTC
3351  ATCTGCAAATACGTAGGGTGTGTACTCTCGAAGATTAACAGTGTGGGTTC
3401  AGTAATATATGGATGAATTCACAGTGGAAGCATTCAAGGGTAGATCATCT
3451  AACGACACCAGATCATCAAGCTATGATTGGAAGCGGTATCAGAAGAGCGA
3501  GGAAGGTAAGCAGTCTTCATATGTTTTCCCTCCACGTAAAGCAGTCTGGG
3551  AAAGTAGCACCCCTTGAGCAGAGACAAGGAAATAATTCAGGAGCATGTGC
3601  TAGGAGAACTTTCTTGCTGAATTCTACTTGCAAGAGCTTTGATGCCTGGC
3651  TTCTGGTGCCTTCTGCAGCACCTGCAAGGCCCAGAGCCTGTGGTGAGCTG
3701  GAGGGAAAGATTCTGCTCAAGTCCAAGCTTCAGCAGGTCATTGTCTTTGC
3751  TTCTTCCCCAGCACTGTGCAGCAGAGTGGAACTGATGTCGAAGCCTCCT
3801  GTCCACTACCTGTTGCTGCAGGCAGACTGCTCTCAGAAAAAGAGAGCTAA
3851  CTCTATGCCATAGTCTGAAGGTAAAATGGTTTTAAAAAGAAAACACAA
3901  AGGCAAAACCGGCTGCCCCATGAGAAGAAAGCAGTGGTAAACATGGTAGA
3951  AAAGGTGCAGAAGCCCCCAGGCAGTGTGACAGGCCCCTCCTGCCACCTAG
4001  AGGCGGGAACAAGCTTCCCTGCCTAGGGCTCTGCCCGCGAAGTGCGTGTT
4051  TCTTTGGTGGGTTTTGTTTGGCGTTTGGTTTTGAGATTTAGACACAAGGG
4101  AAGCCTGAAAGGAGGTGTTGGGCACTATTTTGGTTTGTAAAGCCTGTACT
4151  TCAAATATATATTTTGTGAGGGAGTGTAGCGAATTGGCCAATTTAAAATA
4201  AAGTTGCAAGAGATTGAAGGCTGAGTAGTTGAGAGGGTAACACGTTTAAT
4251  GAGATCTTCTGAAACTACTGCTTCTAAACACTTGTTTGAGTGGTGAGACC
```

*Fig. 8b*

```
4301  TTGGATAGGTGAGTGCTCTTGTTACATGTCTGATGCACTTGCTTGTCCTT
4351  TTCCATCCACATCCATGCATTCCACATCCACGCATTTGTCACTTATCCCA
4401  TATCTGTCATATCTGACATACCTGTCTCTTCGTCACTTGGTCAGAAGAAA
4451  CAGATGTGATAATCCCCAGCCGCCCCAAGTTTGAGAAGATGGCAGTTGCT
4501  TCTTTCCCTTTTTCCTGCTAAGTAAGGATTTTCTCCTGGCTTTGACACCT
4551  CACGAAATAGTCTTCCTGCCTTACATTCTGGGCATTATTTCAAATATCTT
4601  TGGAGTGCGCTGCTCTCAAGTTTGTGTCTTCCTACTCTTAGAGTGAATGC
4651  TCTTAGAGTGAAAGAGAAGGAAGAGAAGATGTTGGCCGCAGTTCTCTGAT
4701  GAACACACCTCTGAATAATGGCCAAAGGTGGGTGGGTTTCTCTGAGGAAC
4751  GGGCAGCGTTTGCCTCTGAAAGCAAGGAGCTCTGCGGAGTTGCAGTTATT
4801  TTGCAACTGATGGTGGAACTGGTGCTTAAAGCAGATTCCCTAGGTTCCT
4851  GCTACTTCTTTTCCTTCTTGGCAGTCAGTTTATTTCTGACAGACAAACAG
4901  CCACCCCACTGCAGGCTTAGAAAGTATGTGGCTCTGCCTGGGTGTGTTA
4951  CAGCTCTGCCCTGGTGAAAGGGGATTAAAACGGGCACCATTCATCCCAAA
5001  CAGGATCCTCATTCATGGATCAAGCTGTAAGGAACTTGGGCTCCAACCTC
5051  AAAACATTAATTGGAGTACGAATGTAATTAAAACTGCATTCTCGCATTCC
5101  TAAGTCATTTAGTCTGGACTCTGCAGCATGTAGGTCGGCAGCTCCCACTT
5151  TCTCAAAGACCACTGATGGAGGAGTAGTAAAAATGGAGACCGATTCAGAA
5201  CAACCAACGGAGTGTTGCCGAAGAAACTGATGGAAATAATGCATGAATTG
5251  TGTGGTGGACATTTTTTTAAATACATAAACTACTTCAAATGAGGTCGGA
5301  GAAGGTCAGTGTTTATTAGCAGCCATAAAACCAGGTGAGCGAGTACCAT
5351  TTTTCTACAAGAAAACGATTCTGAGCTCTGCGTAAGTATAAGTTCTC
5401  CATAGCGGCTGAAGCTCCCCCCTGGCTGCCTGCCATCTCAGCTGGAGTGC
5451  AGTGCCATTTCCTTGGGGTTTCTCTCACAGCAGTAATGGGACAATACTTC
5501  ACAAAAATTCTTTCTTTTCCTGTCATGTGGGATCCCTACTGTGCCCTCCT
5551  GGTTTTACGTTACCCCCTGACTGTTCCATTCAGCGGTTTGGAAAGAGAAA
5601  AAGAATTTGGAAATAAAACATGTCTACGTTATCACCTCCTCCAGCATTTT
5651  GGTTTTTAATTATGTCAATAACTGGCTTAGATTTGGAAATGAGAGGGGGT
5701  TGGGTGTATTACCGAGGAACAAAGGAAGGCTTATATAAACTCAAGTCTTT
5751  TATTTAGAGAACTGGCAAGCTGTCAAAAACAAAAAGGCCTTACCACCAAA
5801  TTAAGTGAATAGCCGCTATAGCCAGCAGGGCCAGCACGAGGGATGGTGCA
5851  CTGCTGGCACTATGCCACGGCCTGCTTGTGACTCTGAGAGCAACTGCTTT
5901  GGAAATGACAGCACTTGGTGCAATTTCCTTTGTTTCAGAATGCGTAGAGC
5951  GTGTGCTTGGCGACAGTTTTTCTAGTTAGGCCACTTCTTTTTTCCTTCTC
6001  TCCTCATTCTCCTAAGCATGTCTCCATGCTGGTAATCCCAGTCAAGTGAA
6051  CGTTCAAACAATGAATCCATCACTGTAGGATTCTCGTGGTGATCAAATCT
6101  TTGTGTGAGGTCTATAAATATGGAAGCTTATTTATTTTTCGTTCTTCCA
6151  TATCAGTCTTCTCTATGACAATTCACATCCACCACAGCAAATTAAAGGTG
6201  AAGGAGGCTGGTGGGATGAAGAGGGTCTTCTAGCTTTACGTTCTTCCTTG
6251  CAAGGCCACAGGAAATGCTGAGAGCTGTAGAATACAGCCTGGGGTAAGA
6301  AGTTCAGTCTCCTGCTGGGACAGCTAACCGCATCTTATAACCCCTTCTGA
6351  GACTCATCTTAGGACCAAATAGGGTCTATCTGGGGTTTTGTTCCTGCTG
6401  TTCCTCCTGGAAGGCTATCTCACTATTTCACTGCTCCACGGTTACAAAC
6451  CAAAGATACAGCCTGAATTTTTCTAGGCCACATTACATAAATTTGACCT
```

*Fig. 8c*

```
6501 GGTACCAATATTGTTCTCTATATAGTTATTTCCTTCCCCACTGTGTTTAA
6551 CCCCTTAAGGCATTCAGAACAACTAGAATCATAGAATGGTTTGGATTGGA
6601 AGGGGCCTTAAACATCATCCATTTCCAACCCTCTGCCATGGGCTGCTTGC
6651 CACCCACTGGCTCAGGCTGCCCAGGGCCCCATCCAGCCTGGCCTTGAGCA
6701 CCTCCAGGGATGGGGCACCCACAGCTTCTCTGGGCAGCCTGTGCCAACAC
6751 CTCACCACTCTCTGGGTAAAGAATTCTCTTTTAACATCTAATCTAAATCT
6801 CTTCTCTTTTAGTTTAAAGCCATTCCTCTTTTTCCCGTTGCTATCTGTCC
6851 AAGAAATGTGTATTGGTCTCCCTCCTGCTTATAAGCAGGAAGTACTGGAA
6901 GGCTGCAGTGAGGTCTCCCCACAGCCTTCTCTTCTCCAGGCTGAACAAGC
6951 CCAGCTCCTTCAGCCTGTCTTCGTAGGAGATCATCTTAGTGGCCCTCCTC
7001 TGGACCCATTCCAACAGTTCCACGGCTTTCTTGTGGAGCCCCAGGTCTGG
7051 ATGCAGTACTTCAGATGGGGCCTTACAAAGGCAGAGCAGATGGGGACAAT
7101 CGCTTACCCCTCCCTGCTGGCTGCCCCTGTTTTGATGCAGCCCAGGGTAC
7151 TGTTGGCCTTTCAGGCTCCCAGACCCCTTGCTGATTTGTGTCAAGCTTTT
7201 CATCCACCAGAACCCACGCTTCCTGGTTAATACTTCTGCCCTCACTTCTG
7251 TAAGCTTGTTTCAGGAGACTTCCATTCTTTAGGACAGACTGTGTTACACC
7301 TACCTGCCCTATTCTTGCATATATACATTTCAGTTCATGTTTCCTGTAAC
7351 AGGACAGAATATGTATTCCTCTAACAAAAATACATGCAGAATTCCTAGTG
7401 CCATCTCAGTAGGGTTTTCATGGCAGTATTAGCACATAGTCAATTTGCTG
7451 CAAGTACCTTCCAAGCTGCGGCCTCCCATAAATCCTGTATTTGGGATCAG
7501 TTACCTTTTGGGGTAAGCTTTTGTATCTGCAGAGACCCTGGGGGTTCTGA
7551 TGTGCTTCAGCTCTGCTCTGTTCTGACTGCACCATTTCTAGATCACCCA
7601 GTTGTTCCTGTACAACTTCCTTGTCCTCCATCCTTTCCCAGCTTGTATCT
7651 TTGACAAATACAGGCCTATTTTTGTGTTTGCTTCAGCAGCCATTTAATTC
7701 TTCAGTGTCATCTTGTTCTGTTGATGCCACTGGAACAGGATTTTCAGCAG
7751 TCTTGCAAAGAACATCTAGCTGAAAACTTTCTGCCATTCAATATTCTTAC
7801 CAGTTCTTCTTGTTTGAGGTGAGCCATAAATTACTAGAACTTCGTCACTG
7851 ACAAGTTTATGCATTTTATTACTTCTATTATGTACTTACTTTGACATAAC
7901 ACAGACACGCACATATTTTGCTGGGATTTCCACAGTGTCTCTGTGTCCTT
7951 CACATGGTTTTACTGTCATACTTCCGTTATAACCTTGGCAATCTGCCCAG
8001 CTGCCCATCACAAGAAAAGAGATTCCTTTTTTATTACTTCTCTTCAGCCA
8051 ATAAACAAAATGTGAGAAGCCCAAACAAGAACTTGTGGGGCAGGCTGCCA
8101 TCAAGGGAGAGACAGCTGAAGGGTTGTGTAGCTCAATAGAATTAAGAAAT
8151 AATAAAGCTGTGTCAGACAGTTTTGCCTGATTTATACAGGCACGCCCAA
8201 GCCAGAGAGGCTGTCTGCCAAGGCCACCTTGCAGTCCTTGGTTTGTAAGA
8251 TAAGTCATAGGTAACTTTTCTGGTGAATTGCGTGGAGAATCATGATGGCA
8301 GTTCTTGCTGTTTACTATGGTAAGATGCTAAAATAGGAGACAGCAAAGTA
8351 ACACTTGCTGCTGTAGGTGCTCTGCTATCCAGACAGCGATGGCACTCGCA
8401 CACCAAGATGAGGGATGCTCCCAGCTGACGGATGCTGGGGCAGTAACAGT
8451 GGGTCCCATGCTGCCTGCTCATTAGCATCACCTCAGCCCTCACCAGCCCA
8501 TCAGAAGGATCATCCCAAGCTGAGGAAAGTTGCTCATCTTCTTCACATCA
8551 TCAAACCTTTGGCCTGACTGATGCCTCCCGGATGCTTAAATGTGGTCACT
8601 GACATCTTTATTTTCTATGATTTCAAGTCAGAACCTCCGGATCAGGAGG
8651 GAACACATAGTGGGAATGTACCCTCAGCTCCAAGGCCAGATCTTCCTTCA
```

*Fig. 8d*

```
 8701  ATGATCATGCATGCTACTTAGGAAGGTGTGTGTGTGAATGTAGAATTG
 8751  CCTTTGTTATTTTTTCTTCCTGCTGTCAGGAACATTTTGAATACCAGAGA
 8801  AAAAGAAAAGTGCTCTTCTTGGCATGGGAGGAGTTGTCACACTTGCAAAA
 8851  TAAAGGATGCAGTCCCAAATGTTCATAATCTCAGGGTCTGAAGGAGGATC
 8901  AGAAACTGTGTATACAATTTCAGGCTTCTCTGAATGCAGCTTTTGAAAGC
 8951  TGTTCCTGGCCGAGGCAGTACTAGTCAGAACCCTCGGAAACAGGAACAAA
 9001  TGTCTTCAAGGTGCAGCAGGAGGAAACACCTTGCCCATCATGAAAGTGAA
 9051  TAACCACTGCCGCTGAAGGAATCCAGCTCCTGTTTGAGCAGGTGCTGCAC
 9101  ACTCCCACACTGAAACAACAGTTCATTTTATAGGACTTCCAGGAAGGAT
 9151  CTTCTTCTTAAGCTTCTTAATTATGGTACATCTCCAGTTGGCAGATGACT
 9201  ATGACTACTGACAGGAGAATGAGGAACTAGCTGGGAATATTTCTGTTTGA
 9251  CCACCATGGAGTCACCCATTTCTTTACTGGTATTTGGAAATAATAATTCT
 9301  GAATTGCAAAGCAGGAGTTAGCGAAGATCTTCATTTCTTCCATGTTGGTG
 9351  ACAGCACAGTTCTGGCTATGAAAGTCTGCTTACAAGGAAGAGGATAAAAA
 9401  TCATAGGGATAATAAATCTAAGTTTGAAGACAATGAGGTTTTAGCTGCAT
 9451  TTGACATGAAGAAATTGAGACCTCTACTGGATAGCTATGGTATTTACGTG
 9501  TCTTTTTGCTTAGTTACTTATTGACCCCAGCTGAGGTCAAGTATGAACTC
 9551  AGGTCTCTCGGGCTACTGGCATGGATTGATTACATACAACTGTAATTTTA
 9601  GCAGTGATTTAGGGTTTATGAGTACTTTTGCAGTAAATCATAGGGTTAGT
 9651  AATGTTAATCTCAGGGAAAAAAAAAAAAGCCAACCCTGACAGACATCCC
 9701  AGCTCAGGTGGAAATCAAGGATCACAGCTCAGTGCGGTCCCAGAGAACAC
 9751  AGGGACTCTTCTCTTAGGACCTTTATGTACAGGGCCTCAAGATAACTGAT
 9801  GTTAGTCAGAAGACTTTCCATTCTGGCCACAGTTCAGCTGAGGCAATCCT
 9851  GGAATTTTCTCTCCGCTGCACAGTTCCAGTCATCCAGTTTGTACAGTTC
 9901  TGGCACTTTTGGGTCAGGCCGTGATCCAAGGAGCAGAAGTTCCAGCTAT
 9951  GGTCAGGGAGTGCCTGACCGTCCCAACTCACTGCACTCAAACAAAGGCGA
10001  AACCACAAGAGTGGCTTTTGTTGAAATTGCAGTGTGGCCCAGAGGGGCTG
10051  CACCAGTACTGGATTGACCACGAGGCAACATTAATCCTCAGCAAGTGCAA
10101  TTTGCAGCCATTAAATTGAACTAACTGATACTACAATGCAATCAGTATCA
10151  ACAAGTGGTTTGGCTTGGAAGATGGAGTCTAGGGGCTCTACAGGAGTAGC
10201  TACTCTCTAATGGAGTTGCATTTTGAAGCAGGACACTGTGAAAAGCTGGC
10251  CTCCTAAAGAGGCTGCTAAACATTAGGGTCAATTTTCCAGTGCACTTTCT
10301  GAAGTGTCTGCAGTTCCCCATGCAAAGCTGCCCAAACATAGCACTTCCAA
10351  TTGAATACAATTATATGCAGGCGTACTGCTTCTTGCCAGCACTGTCCTTC
10401  TCAAATGAACTCAACAAACAATTTCAAAGTCTAGTAGAAAGTAACAAGCT
10451  TGAATGTCATTAAAAAGTATATCTGCTTTCAGTAGTTCAGCTTATTTAT
10501  GCCCACTAGAAACATCTTGTACAAGCTGAACACTGGGGCTCCAGATTAGT
10551  GGTAAAACCTACTTTATACAATCATAGAATCATAGAATGGCCTGGGTTGG
10601  AAGGGACCCCAAGGATCATGAAGATCCAACACCCCCGCCACAGGCAGGGC
10651  CACCAACCTCCAGATCTGGTACTAGACCAGGCAGCCCAGGGCTCCATCCA
10701  ACCTGGCCATGAACACCTCCAGGGATGGAGCATCCACAACCTCTCTGGGC
10751  AGCCTGTGCCAGCACCTCACCACCCTCTCTGTGAAGAACTTTTCCCTGAC
10801  ATCCAATCTAAGCCTTCCCTCCTTGAGGTTAGATCCACTCCCCCTTGTGC
10851  TATCACTGTCTACTCTTGTAAAAGTTGATTCTCCTCCTTTTTGGAAGGT
```

*Fig. 8e*

```
10901  TGCAATGAGGTCTCCTTGCAGCCTTCTTCTCTTCTGCAGGATGAACAAGC
10951  CCAGCTCCCTCAGCCTGTCTTTATAGGAGAGGTGCTCCAGCCCTCTGATC
11001  ATCTTTGTGGCCCTCCTCTGGACCCGCTCCAAGAGCTCCACATCTTTCCT
11051  GTACTGGGGCCCCAGGCCTGAATGCAGTACTCCAGATGGGGCCTCAAAA
11101  GAGCAGAGTAAAGAGGGACAATCACCTTCCTCACCCTGCTGGCCAGCCCT
11151  CTTCTGATGGAGCCCTGGATACAACTGGCTTTCTGAGCTGCAACTTCTCC
11201  TTATCAGTTCCACTATTAAAACAGGAACAATACAACAGGTGCTGATGGCC
11251  AGTGCAGAGTTTTTCACACTTCTTCATTTCGGTAGATCTTAGATGAGGAA
11301  CGTTGAAGTTGTGCTTCTGCGTGTGCTTCTTCCTCCTCAAATACTCCTGC
11351  CTGATACCTCACCCCACCTGCCACTGAATGGCTCCATGGCCCCCTGCAGC
11401  CAGGGCCCTGATGAACCCGGCACTGCTTCAGATGCTGTTTAATAGCACAG
11451  TATGACCAAGTTGCACCTATGAATACACAAACAATGTGTTGCATCCTTCA
11501  GCACTTGAGAAGAAGAGCCAAATTTGCATTGTCAGGAAATGGTTTAGTAA
11551  TTCTGCCAATTAAAACTTGTTTATCTACCATGGCTGTTTTTATGGCTGTT
11601  AGTAGTGGTACACTGATGATGAACAATGGCTATGCAGTAAAATCAAGACT
11651  GTAGATATTGCAACAGACTATAAAATTCCTCTGTGGCTTAGCCAATGTGG
11701  TACTTCCCACATTGTATAAGAAATTTGGCAAGTTTAGAGCAATGTTTGAA
11751  GTGTTGGGAAATTTCTGTATACTCAAGAGGGCGTTTTTGACAACTGTAGA
11801  ACAGAGGAATCAAAAGGGGGTGGGAGGAAGTTAAAAGAAGAGGCAGGTGC
11851  AAGAGAGCTTGCAGTCCCGCTGTGTGTACGACACTGGCAACATGAGGTCT
11901  TTGCTAATCTTGGTGCTTTGCTTCCTGCCCCTGGCTGCCTTAGGGTGCGA
11951  TCTGCCTCAGACCCACAGCCTGGGCAGCAGGAGGACCCTGATGCTGCTGG
12001  CTCAGATGAGGAGAATCAGCCTGTTTAGCTGCCTGAAGGATAGGCACGAT
12051  TTTGGCTTTCCTCAAGAGGAGTTTGGCAACCAGTTTCAGAAGGCTGAGAC
12101  CATCCCTGTGCTGCACGAGATGATCCAGCAGATCTTTAACCTGTTTAGCA
12151  CCAAGGATAGCAGCGCTGCTTGGGATGAGACCCTGCTGGATAAGTTTTAC
12201  ACCGAGCTGTACCAGCAGCTGAACGATCTGGAGGCTTGCGTGATCCAGGG
12251  CGTGGGCGTGACCGAGACCCCTCTGATGAAGGAGGATAGCATCCTGGCTG
12301  TGAGGAAGTACTTTCAGAGGATCACCCTGTACCTGAAGGAGAAGAAGTAC
12351  AGCCCCTGCGCTTGGGAAGTCGTGAGGGCTGAGATCATGAGGAGCTTTAG
12401  CCTGAGCACCAACCTGCAAgagagcttgaggtctaaggagtaaaaagtct
12451  agagtcggggcggCGCGTGGTAGGTGGCGGGGGGTTCCCAGGAGAGCCCC
12501  CAGCGCGGACGGCAGCGCCGTCACTCACCGCTCCGTCTCCCTCCGCCCAG
12551  GGTCGCCTGGCGCAACCGCTGCAAGGGCACCGACGTCCAGGCGTGGATCA
12601  GAGGCTGCCGGCTGTGAGGAGCTGCCGCGCCCGGCCCGCCCGCTGCACAG
12651  CCGGCCGCTTTGCGAGCGCGACGCTACCCGCTTGGCAGTTTTAAACGCAT
12701  CCCTCATTAAAACGACTATACGCAAACGCCTTCCCGTCGGTCCGCGTCTC
12751  TTTCCGCCGCCAGGGCGACACTCGCGGGGAGGCGGGAAGGGGGCCGGGC
12801  GGGAGCCCGCGGCCAACCGTCGCCCCGTGACGGCACCGCCCCGCCCCGT
12851  GACGCGGTGCGGGCGCCGGGGCCGTGGGCTGAGCGCTGCGGCGGGGCCG
12901  GGCCGGGCCGGGGCGGGAGCTGAGCGCGGCGCGGCTGCGGGCGGCGCCCC
12951  CTCCGGTGCAATATGTTCAAGAGAATGGCTGAGTTCGGGCCTGACTCCGG
13001  GGCAGGGTGAAGGTGCGGCGCGGGCGGAGGGACGGGGCGGGCGCGGGGC
13051  CGCCCGGCGGGTGCCGGGGCCTCTGCCGGCCCGCCCGGCTCGGGCTGCTG
```

*Fig. 8f*

```
13101  CGGCGCTTACGGGCGCGCTTCTCGCCGCTGCCGCTTCTCTTCTCTCCCGC
13151  GCAAGGGCGTCACCATCGTGAAGCCGGTAGTGTACGGGAACGTGGCGCGG
13201  TACTTCGGGAAGAAGAGGGAGGAGGACGGGCACACGCATCAGTGGACGGT
13251  TTACGTGAAGCCCTACAGGAACGAGGTAGGGCCCGAGCGCGTCGGCCGCC
13301  GTTCTCGGAGCGCCGGAGCCGTCAGCGCCGCGCCTGGGTGCGCTGTGGA
13351  CACAGCGAGCTTCTCTCGTAGGACATGTCCGCCTACGTGAAAAAAATCCA
13401  GTTCAAGCTGCACGAGAGCTACGGGATCCTCTCCGAGGTGGGTGTTGCG
13451  TCGGGGGGTTTGCTCCGCTCGGTCCCGCTGAGGCTCGTCGCCCTCATCTT
13501  TCTTTCGTGCCGCAGTCGTTACCAAACCGCCGTACGAGATCACCGAAACG
13551  GGCTGGGGCGAATTTGAAATCATCATCAAGATATTTTTCATTGATCCAAA
13601  CGAGCGACCCGTAAGTACGCTCAGCTTCTCGTAGTGCTTCCCCGTCCTG
13651  GCGGCCCGGGGCTGGGCTGCTCGCTGCTGCCGGTCACAGTCCCGCCAGCC
13701  GCGGAGCTGACTGAGCTCCCTTTCCCGGGACGTGTGCTCTGTGTTCGGTC
13751  AGCGAGGCTATCGGGAGGGCTTTGGCTGCATTTGGCTTCTCTGGCGCTTA
13801  GCGCAGGAGCACGTTGTGCTACGCCTGAACTACAGCTGTGAGAAGGCCGT
13851  GGAAACCGCTCTCAAACTGATTTATTGGCGAAATGGCTCTAAACTAAATC
13901  GTCCTCTCTCTTTGGAAATGCTTTAGAGAAGGTCTCTGTGGTAGTTCTTA
13951  TGCATCTATCCTAAAGCACTTGGCCAGACAATTTAAAGACATCAAGCAGC
14001  ATTTATAGCAGGCACGTTTAATAACGAATACTGAATTTAAGTAACTCTGC
14051  TCACGTTGTATGACGTTTATTTTCGTATTCCTGAAAGCCATTAAAATCCT
14101  GTGCAGTTGTTTAGTAAGAACAGCTGCCACTGTTTTGTATCTAGGAGATA
14151  ACTGGTGTTTCCCTACAGTTCTCAAGCTGATAAAACTCTGTCTTTGTATC
14201  TAGGTAACCCTGTATCACTTGCTGAAGCTTTTTCAGTCTGACACCAATGC
14251  AATCCTGGGAAAGAAAACTGTAGTTTCTGAATTCTATGATGAAATGGTAT
14301  GAAAATTTTAATGTCAACCGAGCCTGACTTTATTTAAAAAAAATTATTGA
14351  TGGTGCTGTGTATTTTGGTCCTTCCTTAGATATTTCAAGATCCTACTGCC
14401  ATGATGCAGCAACTGCTAACGACGTCCCGTCAGCTGACACTTGGTGCTTA
14451  CAAGCATGAAACAGAGTGTAAGTGCAAAATGAGGATACCTTCGCCGACCG
14501  TCATTCACTACTAATGTTTTCTGTGGGATGTGATCGTACAGTGAGTTTGG
14551  CTGTGTGAAATTTGAATAGCTTGGTATTGGCAGTGATGACGTGATCGATG
14601  CCTTGCTTATCATGTTTGAAATGAAGTAGAATAAATGCAGCCTGCTTTAT
14651  TTGAGATAGTTTGGTTCATTTTATGGAATGCAAGCAAAGATTATACTTCC
14701  TCACTGAATTGCACTGTCCAAAGGTGTGAAATGTGTGGGGATCTGGAGGA
14751  CCGTGACCGAGGGACATTGGATCGCTATCTCCCATTTCTTTTGCTGTTAC
14801  CAGTTCAGATTTTCTTTTCACCTAGTCTTTAATTCCCAGGGTTTTGTTTT
14851  TTCCTTGGTCATAGTTTTTGTTTTTCACTCTGGCAAATGATGTTGTGAAT
14901  TACACTGCTTCAGCCACAAAACTGATGGACTGAATGAGGTCATCAAACAA
14951  ACTTTTCTTCTTCCGTATTTCCTTTTTTTTCCCCCACTTATCATTTTTAC
15001  TGCTGTTGTTGAGTCTGTAAGGCTAAAGTAACTGTTTTGTGCTTTTTCA
15051  GGACGTGTGCTTTCCAAATTACTGCCACATATATAAAGAAAGGTTGGAAT
15101  TTTAAAGATAATTCATGTTTCTTCTTCTTTTTTGCCACCACAGTTGCAGA
15151  TCTTGAAGTAAAAACCAGGGAAAAGCTGGAAGCTGCCAAAAAGAAAACCA
15201  GTTTTGAAATTGCTGAGCTTAAAGAAAGGTTAAAAGCAAGTCGTGAAACC
15251  ATCAACTGCTTAAAGAGTGAAATCAGAAAACTCGAAGAGGATGATCAGTC
```

*Fig. 8g*

```
15301  TAAAGATATGTGATGAGTGTTGACTTGGCAGGGAGCCTATAATGAGAATG
15351  AAAGGACTTCAGTCGTGGAGTTGTATGCGTTCTCTCCAATTCTGTAACGG
15401  AGACTGTATGAATTTCATTTGCAAATCACTGCAGTGTGTGACAACTGACT
15451  TTTTATAAATGGCAGAAAACAAGAATGAATGTATCCTCATTTTATAGTTA
15501  AAATCTATGGGTATGTACTGGTTTATTTCAAGGAGAATGGATCGTAGAGA
15551  CTTGGAGGCCAGATTGCTGCTTGTATTGACTGCATTTGAGTGGTGTAGGA
15601  ACATTTTGTCTATGGTCCCGTGTTAGTTTACAGAATGCCACTGTTCACTG
15651  TTTTGTTTTGTATTTTACTTTTTCTACTGCAACGTCAAGGTTTTAAAAGT
15701  TGAAAATAAAACATGCAGGTTTTTTTAAATATTTTTTGTCTCTATCCA
15751  GTTTGGGCTTCAAGTATTATTGTTAACAGCAAGTCCTGATTTAAGTCAGA
15801  GGCTGAAGTGTAATGGTATTCAAGATGCTTAAGTCTGTTGTCAGCAAAAC
15851  AAAAGAGAAAACTTCATAAAATCAGGAAGTTGGCATTTCTAATAACTTCT
15901  TTATCAACAGATAAGAGTTTCTAGCCCTGCATCTACTTTCACTTATGTAG
15951  TTGATGCCTTTATATTTTGTGTGTTTGGATGCAGGAAGTGATTCCTACTC
16001  TGTTATGTAGATATTCTATTTAACACTTGTACTCTGCTGTGCTTAGCCTT
16051  TCCCCATGAAAATTCAGCGGCTGTAAATCCCCCTCTTCTTTTGTAGCCTC
16101  ATACAGATGGCAGACCCTCAGGCTTATAAAGGCTTGGGCATCTTCTTTAC
16151  TGCTTTGAGATTCTGTGTTGCAGTAACCTCTGCCAGAGAGGAGAAAAGCC
16201  CCACAAACCTCATCCCCTTCTTCTATAGCAATCAGTATTACTAATGCTTT
16251  GAGAACAGAGCACTGGTTTGAAACGTTTGATAATTAGCATTTAACATGGC
16301  TTGGTAAAGATGCAGAACTGAAACAGCTGTGACAGTATGAACTCAGTATG
16351  GAGACTTCATTAAGACAAACAGCTGTTAAAATCAGGCATGTTTCATTGAG
16401  GAGGACGGGGCAACTTGCACCAGTGGTGCCCACACAAATCCTTCCTGGCG
16451  CTGCAGACCAATTTTTCTGGCATTCTGACTGCCGTTGCTGCTGGTCACAG
16501  AGAGCAACTATTTTTATCAGCCACAGGCAATTTGCTTGTAGTATTTTCCA
16551  AGTGTTGTAGGTAAGTATAAATGCATCGGCTCCAGAGCACTTTGAGTATA
16601  CTTATTAAAAACATAAATGAAAGACAAATTAGCTTTGCTTGGGTGCACAG
16651  AACATTTTTAGTTCCAGCCTGCTTTTTGGTAGAAGCCCTCTTCTGAGGCT
16701  AGAACTGACTTTGACAAGTAGAGAAACTGGCAACGGAGCTATTGCTATCG
16751  AAGGATCCTTGTTAACAAAGTTAATCGTCTTTTAAGGTTTGGTTTATTCA
16801  TTAAATTTGCTTTTAAGCTGTAGCTGAAAAAGAACGTGCTGTCTTCCATG
16851  CACCAGGTGGCAGCTCTGTGCAAAGTGCTCTCTGGTCTCACCAGCCTTTT
16901  AATTGCCGGGATTCTGGCACGTCTGAGAGGGCTCAGACTGGCTTCGTTTG
16951  TTTGAACAGCGTGTACTGCTTTCTGTAGACATGGCCGGTTTCTCTCCTGC
17001  AGCTTATGAAACTGTTCACACTGAACACACTGGAACAGGTTGCCCAAGGA
17051  GGCCGTGGATGCCCCATCCCTGGAGGCATTCAAGGCCAGGCTGGATGTGG
17101  CTCTGGGCAGCCTGGTCTGGTGGTTGGCGATCCTGCACATAGCAGCGGGG
17151  TTGAAACTCGATGATCACTGTGGTCCTTTTCAACCCAGGCTATTCTATGA
17201  TTCTATGATTCAACAGCAAATCATATGTACTGAGAGAGGAAACAAACACA
17251  AGTGCTACTGTTTGCAAGTTTTGTTCATTTGGTAAAAGAGTCAGGTTTTA
17301  AAATTCAAAATCTGTCTGGTTTTGGTGTTTTTTTTTTTATTTATTATT
17351  TCTTTGGGGTTCTTTTTGATGCTTTATCTTTCTGCCAGGACTGTGTGA
17401  CAATGGGAACGAAAAGAACATGCCAGGCACTGTCCTGGATTGCACACGC
17451  TGGTTGCACTCAGTAGCAGGCTCAGAACTGCCAGTCTTTCCACAGTATTA
```

*Fig. 8h*

| | |
|---|---|
| 17501 | CTTTCTAAACCTAATTTTAATAGCGTTAGTAGACTTCCATCACTGGGCAG |
| 17551 | TGCTTAGTGAATGCTCTGTGTGAACGTTTTACTTATAAGCATGTTGGAAG |
| 17601 | TTTTGATGTTCCTGGATGCAGTAGGGAAGGACAGATTAGCTATGTGAAAA |
| 17651 | GTAGATTCTGAGTATCGGGGTTACAAAAAGTATAGAAACGATGAGAAATT |
| 17701 | CTTGTTGTAACTAATTGGAATTTCTTTAAGCGTTCACTTATGCTACATTC |
| 17751 | ATAGTATTTCCATTTAAAAGTAGGAAAAGGTAAAACGTGAAATCGTGTGA |
| 17801 | TTTTCGGATGGAACACCGCCTTCCTATGCACCTGACCAACTTCCAGAGGA |
| 17851 | AAAGCCTATTGAAAGCCGAGATTAAGCCACCAAAAGAACTCATTTGCATT |
| 17901 | GGAATATGTAGTATTTGCCCTCTTCCTCCCGGGTAATTACTATACTTTAT |
| 17951 | AGGGTGCTTATATGTTAAATGAGTGGCTGGCACTTTTTATTCTCACAGCT |
| 18001 | GTGGGGAATTCTGTCCTCTAGGACAGAAACAATTTTAATCTGTTCCACTG |
| 18051 | GTGACTGCTTTGTCAGCACTTCCACCTGAAGAGATCAATACACTCTTCAA |
| 18101 | TGTCTAGTTCTGCAACACTTGGCAAACCTCACATCTTATTTCATACTCTC |
| 18151 | TTCATGCCTATGCTTATTAAAGCAATAATCTGGGTAATTTTTGTTTTAAT |
| 18201 | CACTGTCCTGACCCCAGTGATGACCGTGTCCCACCTAAAGCTCAATTCAG |
| 18251 | GTCCTGAATCTCTTCAACTCTCTATAGCTAACATGAAGAATCTTCAAAAG |
| 18301 | TTAGGTCTGAGGGACTTAAGGCTAACTGTAGATGTTGTTGCCTGGTTTCT |
| 18351 | GTGCTGAAGGCCGTGTAGTAGTTAGAGCATTCAACCTCTAGaagaagctt |
| 18401 | ggccagctggtcgacctgcagatccggccctcgagggggggcccggtacc |
| 18451 | cagcttttgttcccttTagtgagggttaatttcgagcttggcgtaatcat |
| 18501 | ggtcatagctgtttcctgtgtgaaattgttatccgctcacaattccacac |
| 18551 | aacatacgagccggaagcataaagtgtaaagcctggggtgcctaatgagt |
| 18601 | gagctaactcacattaattgcgttgcgctcactgcccgctttccagtcgg |
| 18651 | gaaacctgtcgtgccagctgcattaatgaatcggccaacgcgcggggaga |
| 18701 | ggcggtttgcgtattgggcgctcttccgcttcctcgctcactgactcgct |
| 18751 | gcgctcggtcgttcggctgcggcgagcggtatcagctcactcaaaggcgg |
| 18801 | taatacggttatccacagaatcaggggataacgcaggaaagaacatgtga |
| 18851 | gcaaaaggccagcaaaaggccaggaaccgtaaaaaggccgcgttgctggc |
| 18901 | gtttttccataggctccgcccccctgacgagcatcacaaaaatcgacgct |
| 18951 | caagtcagaggtggcgaaacccgacaggactataaagataccaggcgttt |
| 19001 | ccccctggaagctcctcgtgcgctctcctgttccgaccctgccgcttac |
| 19051 | cggatacctgtccgcctttctcccttcgggaagcgtggcgctttctcata |
| 19101 | gctcacgctgtaggtatctcagttcggtgtaggtcgttcgctccaagctg |
| 19151 | ggctgtgtgcacgaaccccccgttcagcccgaccgctgcgccttatccgg |
| 19201 | taactatcgtcttgagtccaacccggtaagacacgacttatcgccactgg |
| 19251 | cagcagccactggtaacaggattagcagagcgaggtatgtaggcggtgct |
| 19301 | acagagttcttgaagtggtggcctaactacggctacactagaaggacagt |
| 19351 | atttggtatctgcgctctgctgaagccagttaccttcggaaaaagagttg |
| 19401 | gtagctcttgatccggcaaacaaaccaccgctggtagcggtggtttttt |
| 19451 | gtttgcaagcagcagattacgcgcagaaaaaaaggatctcaagaagatcc |
| 19501 | tttgatcttttctacggggtctgacgctcagtggaacgaaaactcacgtt |
| 19551 | aagggattttggtcatgagattatcaaaaaggatcttcacctagatcctt |
| 19601 | ttaaattaaaaatgaagttttaaatcaatctaaagtatatatgagtaaac |
| 19651 | ttggtctgacagttaccaatgcttaatcagtgaggcacctatctcagcga |

*Fig. 8i*

```
19701  tctgtctatttcgttcatccatagttgcctgactccccgtcgtgtagata
19751  actacgatacgggagggcttaccatctggccccagtgctgcaatgatacc
19801  gcgagacccacgctcaccggctccagatttatcagcaataaaccagccag
19851  ccggaagggccgagcgcagaagtggtcctgcaactttatccgcctccatc
19901  cagtctattaattgttgccgggaagctagagtaagtagttcgccagttaa
19951  tagtttgcgcaacgttgttgccattgctacaggcatcgtggtgtcacgct
20001  cgtcgtttggtatggcttcattcagctccggttcccaacgatcaaggcga
20051  gttacatgatccccatgttgtgcaaaaagcggttagctccttcggtcc
20101  tccgatcgttgtcagaagtaagttggccgcagtgttatcactcatggtta
20151  tggcagcactgcataattctcttactgtcatgccatccgtaagatgcttt
20201  tctgtgactggtgagtactcaaccaagtcattctgagaatagtgtatgcg
20251  gcgaccgagttgctcttgcccggcgtcaatacgggataataccgcgccac
20301  atagcagaactttaaaagtgctcatcattggaaaacgttcttcggggcga
20351  aaactctcaaggatcttaccgctgttgagatccagttcgatgtaaccac
20401  tcgtgcacccaactgatcttcagcatcttttactttcaccagcgtttctg
20451  ggtgagcaaaaacaggaaggcaaaatgccgcaaaaagggaataagggcg
20501  acacggaaatgttgaatactcatactcttccttttcaatattattgaag
20551  catttatcagggttattgtctcatgagcggatacatatttgaatgtattt
20601  agaaaaataaacaatagggttccgcgcacatttccccgaaaagtgcca
20651  cctaaattgtaagcgttaatattttgttaaaattcgcgttaaattttgt
20701  taaatcagctcatttttaaccaataggccgaaatcggcaaaatccctta
20751  taaatcaaaagaatagaccgagataggttgagtgttgttccagtttgga
20801  acaagagtccactattaaagaacgtggactccaacgtcaaagggcgaaaa
20851  accgtctatcagggcgatggcccactacgtgaaccatcaccctaatcaag
20901  ttttttggggtcgaggtgccgtaaagcactaaatcggaaccctaaggga
20951  gcccccgatttagagcttgacggggaaagccggcgaacgtggcgagaaag
21001  gaagggaagaaagcgaaaggagcgggcgctagggcgctggcaagtgtagc
21051  ggtcacgctgcgcgtaaccaccacccgccgcgcttaatgcgccgctac
21101  agggcgcgtcccattcgccattcaggctgcgcaactgttgggaagggcga
21151  tcggtgcgggcctcttcgctattacgccagctggcgaaaggggggatgtgc
21201  tgcaaggcgattaagttgggtaacgccagggttttcccagtcacgacgtt
21251  gtaaaacgacggccagtgaattgtaatacgactcactatagggcgaattg
21301  gagctccaccgcggtggcggccgctctag
```

*Fig. 8j*

SEQUENCE LISTING

```
<160> NUMBER OF SEQ ID NOS: 85

<210> SEQ ID NO 1
<211> LENGTH: 20
<212> TYPE: DNA
<213> ORGANISM: Artificial Sequence
<220> FEATURE:
<223> OTHER INFORMATION: Primer 5pLMAR2

<400> SEQUENCE: 1
tgccgccttc tttgatattc                                              20

<210> SEQ ID NO 2
<211> LENGTH: 20
<212> TYPE: DNA
<213> ORGANISM: Artificial Sequence
<220> FEATURE:
<223> OTHER INFORMATION: Primer LE-6.1kbrev1

<400> SEQUENCE: 2
ttggtggtaa ggccttttg                                               20

<210> SEQ ID NO 3
<211> LENGTH: 20
<212> TYPE: DNA
<213> ORGANISM: Artificial Sequence
<220> FEATURE:
<223> OTHER INFORMATION: Primer lys-6.1

<400> SEQUENCE: 3
ctggcaagct gtcaaaaaca                                              20

<210> SEQ ID NO 4
<211> LENGTH: 20
<212> TYPE: DNA
<213> ORGANISM: Artificial Sequence
<220> FEATURE:
<223> OTHER INFORMATION: Primer LysE1rev

<400> SEQUENCE: 4
cagctcacat cgtccaaaga                                              20

<210> SEQ ID NO 5
<211> LENGTH: 34
```

```
<212> TYPE: DNA
<213> ORGANISM: Artificial Sequence
<220> FEATURE:
<223> OTHER INFORMATION: Primer LYSBSU

<400> SEQUENCE: 5 cccccccta aggcagccag gggcaggaag caaa                                34

<210> SEQ ID NO 6
<211> LENGTH: 12
<212> TYPE: DNA
<213> ORGANISM: Artificial Sequence
<220> FEATURE:
<223> OTHER INFORMATION: Primer SaltoNotI

<400> SEQUENCE: 6
tcgagcggcc gc                                                       12

<210> SEQ ID NO 7
<211> LENGTH: 20
<212> TYPE: DNA
<213> ORGANISM: Artificial Sequence
<220> FEATURE:
<223> OTHER INFORMATION: Primer T7

<400> SEQUENCE: 7
taatacgact cactataggg                                               20

<210> SEQ ID NO 8
<211> LENGTH: 21
<212> TYPE: DNA
<213> ORGANISM: Artificial Sequence
<220> FEATURE:
<223> OTHER INFORMATION: Primerlys61enfor1

<400> SEQUENCE: 8
cgtggtgatc aaatctttgt g                                             21

<210> SEQ ID NO 9
<211> LENGTH: 20
<212> TYPE: DNA
<213> ORGANISM: Artificial Sequence
<220> FEATURE:
<223> OTHER INFORMATION: Primer lys61enrev1

<400> SEQUENCE: 9
aggagggcac agtagggatc                                               20

<210> SEQ ID NO 10
<211> LENGTH: 19
<212> TYPE: DNA
<213> ORGANISM: Artificial Sequence
<220> FEATURE:
<223> OTHER INFORMATION: Primer 5MARfor1

<400> SEQUENCE: 10
gtggcctgtg tctgtgctt                                                19

<210> SEQ ID NO 11
<211> LENGTH: 20
<212> TYPE: DNA
<213> ORGANISM: Artificial Sequence
<220> FEATURE:
<223> OTHER INFORMATION: Primer IFN-3rev

<400> SEQUENCE: 11
```
aactcctctt gaggaaagcc                                              20

<210> SEQ ID NO 12
<211> LENGTH: 20
<212> TYPE: DNA
<213> ORGANISM: Artificial Sequence
<220> FEATURE:
<223> OTHER INFORMATION: Primer lys001rev

<400> SEQUENCE: 12
tcctgtttgg gatgaatggt                                              20

<210> SEQ ID NO 13
<211> LENGTH: 20
<212> TYPE: DNA
<213> ORGANISM: Artificial Sequence
<220> FEATURE:
<223> OTHER INFORMATION: Primer lys002for

<400> SEQUENCE: 13
ctctcagaat gcccaactcc                                              20

<210> SEQ ID NO 14
<211> LENGTH: 20
<212> TYPE: DNA
<213> ORGANISM: Artificial Sequence
<220> FEATURE:
<223> OTHER INFORMATION: Primer lys003for

<400> SEQUENCE: 14
tgtattggtc tccctcctgc                                              20

<210> SEQ ID NO 15
<211> LENGTH: 20
<212> TYPE: DNA
<213> ORGANISM: Artificial Sequence
<220> FEATURE:
<223> OTHER INFORMATION: Primer lys005for

<400> SEQUENCE: 15
tgttgaaatt gcagtgtggc                                              20

<210> SEQ ID NO 16
<211> LENGTH: 20
<212> TYPE: DNA
<213> ORGANISM: Artificial Sequence
<220> FEATURE:
<223> OTHER INFORMATION: Primer lys006rev

<400> SEQUENCE: 16
tgacaatgca aatttggctc                                              20

<210> SEQ ID NO 17
<211> LENGTH: 20
<212> TYPE: DNA
<213> ORGANISM: Artificial Sequence
<220> FEATURE:
<223> OTHER INFORMATION: Primer lys007for

<400> SEQUENCE: 17
gatatccttg cagtgcccat                                              20

<210> SEQ ID NO 18
<211> LENGTH: 20
<212> TYPE: DNA
<213> ORGANISM: Artificial Sequence

```
<220> FEATURE:
<223> OTHER INFORMATION: Primer lys008rev

<400> SEQUENCE: 18
ggacaagcaa gtgcatcaga                                                    20

<210> SEQ ID NO 19
<211> LENGTH: 20
<212> TYPE: DNA
<213> ORGANISM: Artificial Sequence
<220> FEATURE:
<223> OTHER INFORMATION: Primer lys009for

<400> SEQUENCE: 19
ctgatgtgct tcagctctgc                                                    20

<210> SEQ ID NO 20
<211> LENGTH: 20
<212> TYPE: DNA
<213> ORGANISM: Artificial Sequence
<220> FEATURE:
<223> OTHER INFORMATION: Primer lys010rev

<400> SEQUENCE: 20
tccatggtgg tcaaacagaa                                                    20

<210> SEQ ID NO 21
<211> LENGTH: 20
<212> TYPE: DNA
<213> ORGANISM: Artificial Sequence
<220> FEATURE:
<223> OTHER INFORMATION: Primer lys011for

<400> SEQUENCE: 21
gtactagacc aggcagccca                                                    20

<210> SEQ ID NO 22
<211> LENGTH: 20
<212> TYPE: DNA
<213> ORGANISM: Artificial Sequence
<220> FEATURE:
<223> OTHER INFORMATION: Primer lys012rev

<400> SEQUENCE: 22
gtgggaagta ccacattggc                                                    20

<210> SEQ ID NO 23
<211> LENGTH: 20
<212> TYPE: DNA
<213> ORGANISM: Artificial Sequence
<220> FEATURE:
<223> OTHER INFORMATION: Primer lys013for

<400> SEQUENCE: 23
cgctcaggag aaagtgaacc                                                    20

<210> SEQ ID NO 24
<211> LENGTH: 20
<212> TYPE: DNA
<213> ORGANISM: Artificial Sequence
<220> FEATURE:
<223> OTHER INFORMATION: Primer lys014rev

<400> SEQUENCE: 24
cggttttgcc tttgtgtttt                                                    20
```

<210> SEQ ID NO 25
<211> LENGTH: 20
<212> TYPE: DNA
<213> ORGANISM: Artificial Sequence
<220> FEATURE:
<223> OTHER INFORMATION: Primer lys015rev

<400> SEQUENCE: 25
aaatgctcga tttcattggg                                              20

<210> SEQ ID NO 26
<211> LENGTH: 20
<212> TYPE: DNA
<213> ORGANISM: Artificial Sequence
<220> FEATURE:
<223> OTHER INFORMATION: Primer lys016rev

<400> SEQUENCE: 26
gccaatcaga ctgcatttca                                              20

<210> SEQ ID NO 27
<211> LENGTH: 20
<212> TYPE: DNA
<213> ORGANISM: Artificial Sequence
<220> FEATURE:
<223> OTHER INFORMATION: Prmer lys017rev

<400> SEQUENCE: 27
aaccgctgaa tggaacagtc                                              20

<210> SEQ ID NO 28
<211> LENGTH: 20
<212> TYPE: DNA
<213> ORGANISM: Artificial Sequence
<220> FEATURE:
<223> OTHER INFORMATION: Primer lys018for

<400> SEQUENCE: 28
acacgcacat attttgctgg                                              20

<210> SEQ ID NO 29
<211> LENGTH: 20
<212> TYPE: DNA
<213> ORGANISM: Artificial Sequence
<220> FEATURE:
<223> OTHER INFORMATION: Primer lys019rev

<400> SEQUENCE: 29
caggagctgg attccttcag                                              20

<210> SEQ ID NO 30
<211> LENGTH: 20
<212> TYPE: DNA
<213> ORGANISM: Artificial Sequence
<220> FEATURE:
<223> OTHER INFORMATION: Primer lys020for

<400> SEQUENCE: 30
aaaggatgca gtcccaaatg                                              20

<210> SEQ ID NO 31
<211> LENGTH: 20
<212> TYPE: DNA
<213> ORGANISM: Artificial Sequence
<220> FEATURE:
<223> OTHER INFORMATION: Primer lys021rev

<400> SEQUENCE: 31 gccctagac tccatcttcc                                        20

<210> SEQ ID NO 32
<211> LENGTH: 20
<212> TYPE: DNA
<213> ORGANISM: Artificial Sequence
<220> FEATURE:
<223> OTHER INFORMATION: Primer lys022rev

<400> SEQUENCE: 32
atttgctgtg gtggatgtga                                       20

<210> SEQ ID NO 33
<211> LENGTH: 20
<212> TYPE: DNA
<213> ORGANISM: Artificial Sequence
<220> FEATURE:
<223> OTHER INFORMATION: Primer lys024for

<400> SEQUENCE: 33
ccttgcagtc cttggtttgt                                       20

<210> SEQ ID NO 34
<211> LENGTH: 20
<212> TYPE: DNA
<213> ORGANISM: Artificial Sequence
<220> FEATURE:
<223> OTHER INFORMATION: Primer lys025rev

<400> SEQUENCE: 34
atgatccttc tgatgggctg                                       20

<210> SEQ ID NO 35
<211> LENGTH: 20
<212> TYPE: DNA
<213> ORGANISM: Artificial Sequence
<220> FEATURE:
<223> OTHER INFORMATION: Primer lys026rev

<400> SEQUENCE: 35
acagtgatag cacaaggggg                                       20

<210> SEQ ID NO 36
<211> LENGTH: 20
<212> TYPE: DNA
<213> ORGANISM: Artificial Sequence
<220> FEATURE:
<223> OTHER INFORMATION: Primer lys027rev

<400> SEQUENCE: 36
gtaaacagct gcaacaggca                                       20

<210> SEQ ID NO 37
<211> LENGTH: 21
<212> TYPE: DNA
<213> ORGANISM: Artificial Sequence
<220> FEATURE:
<223> OTHER INFORMATION: Primer lys028rev

<400> SEQUENCE: 37
caacacaaaa gttggacagc a                                     21

<210> SEQ ID NO 38

<210> SEQ ID NO 38
<211> LENGTH: 20
<212> TYPE: DNA
<213> ORGANISM: Artificial Sequence
<220> FEATURE:
<223> OTHER INFORMATION: Primer lys030rev

<400> SEQUENCE: 38
tttgcagatg agacgtttgc                                           20

<210> SEQ ID NO 39
<211> LENGTH: 20
<212> TYPE: DNA
<213> ORGANISM: Artificial Sequence
<220> FEATURE:
<223> OTHER INFORMATION: Primer lys030rev

<400> SEQUENCE: 39
ccacaagttc ttgtttgggc                                           20

<210> SEQ ID NO 40
<211> LENGTH: 20
<212> TYPE: DNA
<213> ORGANISM: Artificial Sequence
<220> FEATURE:
<223> OTHER INFORMATION: Primer lys031rev

<400> SEQUENCE: 40
atcaatccat gccagtagcc                                           20

<210> SEQ ID NO 41
<211> LENGTH: 20
<212> TYPE: DNA
<213> ORGANISM: Artificial Sequence
<220> FEATURE:
<223> OTHER INFORMATION: Primer lys032rev

<400> SEQUENCE: 41
gtttaaggcc ccttccaatc                                           20

<210> SEQ ID NO 42
<211> LENGTH: 20
<212> TYPE: DNA
<213> ORGANISM: Artificial Sequence
<220> FEATURE:
<223> OTHER INFORMATION: Primer lys033for

<400> SEQUENCE: 42 gagaggggt tgggtgtatt                                            20

<210> SEQ ID NO 43
<211> LENGTH: 20
<212> TYPE: DNA
<213> ORGANISM: Artificial Sequence
<220> FEATURE:
<223> OTHER INFORMATION: Primer lys034for

<400> SEQUENCE: 43
acagtggaag cattcaaggg                                           20

<210> SEQ ID NO 44
<211> LENGTH: 20
<212> TYPE: DNA
<213> ORGANISM: Artificial Sequence
<220> FEATURE:
<223> OTHER INFORMATION: Primer lys037for

<400> SEQUENCE: 44
ccaatgcctt tggttctgat                                                20

<210> SEQ ID NO 45
<211> LENGTH: 20
<212> TYPE: DNA
<213> ORGANISM: Artificial Sequence
<220> FEATURE:
<223> OTHER INFORMATION: Primer lys038for

<400> SEQUENCE: 45
aaaacacaaa ggcaaaaccg                                                20

<210> SEQ ID NO 46
<211> LENGTH: 20
<212> TYPE: DNA
<213> ORGANISM: Artificial Sequence
<220> FEATURE:
<223> OTHER INFORMATION: Primer lys039rev

<400> SEQUENCE: 46
ctaagcctcg ccagtttcaa                                                20

<210> SEQ ID NO 47
<211> LENGTH: 20
<212> TYPE: DNA
<213> ORGANISM: Artificial Sequence
<220> FEATURE:
<223> OTHER INFORMATION: Primer lys040rev

<400> SEQUENCE: 47
tgccatgaaa accctactga                                                20

<210> SEQ ID NO 48
<211> LENGTH: 20
<212> TYPE: DNA
<213> ORGANISM: Artificial Sequence
<220> FEATURE:
<223> OTHER INFORMATION: Primer lys041for

<400> SEQUENCE: 48
ggaatgtacc ctcagctcca                                                20

<210> SEQ ID NO 49
<211> LENGTH: 20
<212> TYPE: DNA
<213> ORGANISM: Artificial Sequence
<220> FEATURE:
<223> OTHER INFORMATION: Primer lys042rev

<400> SEQUENCE: 49
cctctttagg aggccagctt                                                20

<210> SEQ ID NO 50
<211> LENGTH: 20
<212> TYPE: DNA
<213> ORGANISM: Artificial Sequence
<220> FEATURE:
<223> OTHER INFORMATION: Primer lys043rev

<400> SEQUENCE: 50
aagatgatca gagggctgga                                                20

<210> SEQ ID NO 51
<211> LENGTH: 20
<212> TYPE: DNA

```
<213> ORGANISM: Artificial Sequence
<220> FEATURE:
<223> OTHER INFORMATION: Primer lys044rev

<400> SEQUENCE: 51
gcagcgctgg taatcttcat                                           20

<210> SEQ ID NO 52
<211> LENGTH: 20
<212> TYPE: DNA
<213> ORGANISM: Artificial Sequence
<220> FEATURE:
<223> OTHER INFORMATION: Primer lys045for

<400> SEQUENCE: 52
cttcagatcc caggaagtgc                                           20

<210> SEQ ID NO 53
<211> LENGTH: 20
<212> TYPE: DNA
<213> ORGANISM: Artificial Sequence
<220> FEATURE:
<223> OTHER INFORMATION: Primer lys46for

<400> SEQUENCE: 53
ttcctgcctt acattctggg                                           20

<210> SEQ ID NO 54
<211> LENGTH: 20
<212> TYPE: DNA
<213> ORGANISM: Artificial Sequence
<220> FEATURE:
<223> OTHER INFORMATION: Primer lys047for

<400> SEQUENCE: 54
cccactgcag gcttagaaag                                           20

<210> SEQ ID NO 55
<211> LENGTH: 20
<212> TYPE: DNA
<213> ORGANISM: Artificial Sequence
<220> FEATURE:
<223> OTHER INFORMATION: Primer lys048for

<400> SEQUENCE: 55
agttctccat agcggctgaa                                           20

<210> SEQ ID NO 56
<211> LENGTH: 20
<212> TYPE: DNA
<213> ORGANISM: Artificial Sequence
<220> FEATURE:
<223> OTHER INFORMATION: Primer lys051for

<400> SEQUENCE: 56
tgcatccttc agcacttgag                                           20

<210> SEQ ID NO 57
<211> LENGTH: 20
<212> TYPE: DNA
<213> ORGANISM: Artificial Sequence
<220> FEATURE:
<223> OTHER INFORMATION: Primer lys052rev

<400> SEQUENCE: 57
gcaggaggga gaccaataca                                           20
```

<210> SEQ ID NO 58
<211> LENGTH: 20
<212> TYPE: DNA
<213> ORGANISM: Artificial Sequence
<220> FEATURE:
<223> OTHER INFORMATION: Primer lys053for

<400> SEQUENCE: 58
tgcacaagga tgtctgggta                                         20

<210> SEQ ID NO 59
<211> LENGTH: 20
<212> TYPE: DNA
<213> ORGANISM: Artificial Sequence
<220> FEATURE:
<223> OTHER INFORMATION: Primer lys054for

<400> SEQUENCE: 59
tcctagcaac tgcggatttt                                         20

<210> SEQ ID NO 60
<211> LENGTH: 20
<212> TYPE: DNA
<213> ORGANISM: Artificial Sequence
<220> FEATURE:
<223> OTHER INFORMATION: Primer lys056for

<400> SEQUENCE: 60
tcttccatgt tggtgacagc                                         20

<210> SEQ ID NO 61
<211> LENGTH: 20
<212> TYPE: DNA
<213> ORGANISM: Artificial Sequence
<220> FEATURE:
<223> OTHER INFORMATION: Primer lys058for

<400> SEQUENCE: 61
cccccttgtg ctatcactgt                                         20

<210> SEQ ID NO 62
<211> LENGTH: 20
<212> TYPE: DNA
<213> ORGANISM: Artificial Sequence
<220> FEATURE:
<223> OTHER INFORMATION: Primer lys059for

<400> SEQUENCE: 62
ctgacagaca tcccagctca                                         20

<210> SEQ ID NO 63
<211> LENGTH: 20
<212> TYPE: DNA
<213> ORGANISM: Artificial Sequence
<220> FEATURE:
<223> OTHER INFORMATION: Primer lys060for

<400> SEQUENCE: 63
aagttgtgct tctgcgtgtg                                         20

<210> SEQ ID NO 64
<211> LENGTH: 20
<212> TYPE: DNA
<213> ORGANISM: Artificial Sequence
<220> FEATURE:

-continued

```
<223> OTHER INFORMATION: Primer lys061for

<400> SEQUENCE: 64
ttgttcctgc tgttcctcct                                                    20

<210> SEQ ID NO 65
<211> LENGTH: 12728
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
      (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
      Peptide
<220> FEATURE:
<221> NAME/KEY: misc_feature
<222> LOCATION: (11946)..(12443)
<223> OTHER INFORMATION: Human Interferon alpha 2d encoding region
      codon optimized for exp ression in chicken cells (IFNMAGMAX
<220> FEATURE:
<221> NAME/KEY: polyA_signal
<222> LOCATION: (12444)..(12728)

<400> SEQUENCE: 65
```

```
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttcttttttc ttagtaaatt ttctactgga     300
ctgtatgttt tgacaggtca gaaacatttc ttcaaaagaa gaacctttg gaaactgtac      360 agcccttttc tttcattccc ttttttgcttt ctgtgccaat gcctttggtt ctgattgcat    420
tatggaaaac gttgatcgga acttgaggtt tttatttata gtgtggcttg aaagcttgga     480
tagctgttgt tacacgagat accttattaa gtttaggcca gcttgatgct ttatttttttc    540 cctttgaagt agtgagcgtt ctctggtttt tttcctttga aactggtgag cttagatttt     600
ttctaatggg attttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttttatc    780 tctatgctct gtgtgtacag gtcaaacaga cttcactcct atttttattt atagaatttt     840
atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaaagaag aatgaatact ttctaaaata    1080
ttttggcata ggaagcaagc tgcatggatt tgtttgggac ttaaattatt ttggtaacgg    1140
agtgcatagg ttttaaacac agttgcagca tgctaacgag tcacagcgtt tatgcagaag    1200
tgatgcctgg atgcctgttg cagctgttta cggcactgcc ttgcagtgag cattgcagat    1260
aggggtgggg tgctttgtgt cgtgttccca cacgctgcca cacagccacc tcccggaaca    1320
catctcacct gctgggtact tttcaaacca tcttagcagt agtagatgag ttactatgaa    1380
acagagaagt tcctcagttg gatattctca tgggatgtct ttttttcccat gttgggcaaa    1440 gtatgataaa gcatctctat ttgtaaatta tgcacttgtt agttcctgaa tcctttctat    1500
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat ttcagttgta aaagaattcc gcctattcat    1680
accatgtaat gtaattttac accccagtg ctgacacttt ggaatatatt caagtaatag     1740
actttggcct caccctcttg tgtactgtat tttgtaatag aaaatatttt aaactgtgca    1800
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920
aaaaaaaaag taatataaaa aggaccaggt gttttacaag tgaaatacat tcctatttgg    1980
taaacagtta catttttatg aagattacca gcgctgctga ctttctaaac ataaggctgt    2040
attgtcttcc tgtaccattg catttcctca ttcccaattt gcacaaggat gtctgggtaa    2100
actattcaag aaatggcttt gaaatacagc atgggagctt gtctgagttg aatgcagag     2160 ttgcactgca aaatgtcagg aaatggatgt ctctcagaat gcccaactcc aaaggatttt    2220
atatgtgtat atagtaagca gtttcctgat tccagcaggc caaagagtct gctgaatgtt    2280
gtgttgccgg agacctgtat ttctcaacaa ggtaagatgg tatcctagca actgcggatt    2340
ttaatacatt ttcagcagaa gtacttagtt aatctctacc tttagggatc gtttcatcat    2400
```

```
ttttagatgt tatacttgaa atactgcata acttttagct ttcatgggtt cctttttttc    2460
agcctttagg agactgttaa gcaatttgct gtccaacttt tgtgttggtc ttaaactgca    2520
atagtagttt accttgtatt gaagaaataa agaccatttt tatattaaaa aatacttttg    2580
tctgtcttca ttttgacttg tctgatatcc ttgcagtgcc cattatgtca gttctgtcag    2640
atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata cttttttaaa gtcaactttt    2820
tatcagattt ttttttcatt tggaaatata ttgttttcta gactgcatag cttctgaatc    2880
tgaaatgcag tctgattggc atgaagaagc acagcactct tcatcttact taaacttcat    2940
tttggaatga aggaagttaa gcaagggcac aggtccatga aatagagaca gtgcgctcag    3000
gagaaagtga acctggattt ctttggctag tgttctaaat ctgtagtgag aaagtaaca    3060 cccgattcct tgaaagggct ccagctttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tatttttaag tactgtgttg caaacgtctc atctgcaaat    3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
aagcggtatc agaagagcga ggaaggtaag cagtcttcat atgttttccc tccacgtaaa    3540
gcagtctggg aaagtagcac cccttgagca gagacaagga aataattcag gagcatgtgc    3600
taggagaact tcttgctga attctacttg caagagcttt gatgcctggc ttctggtgcc    3660
ttctgcagca cctgcaaggc ccagagcctg tggtgagctg gagggaaaga ttctgctcaa    3720
gtccaagctt cagcaggtca ttgtctttgc ttcttccccc agcactgtgc agcagagtgg    3780
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggcccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggtttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgcacata cctgtctctt cgtcacttgg    4440
tcagaagaaa cagatgtgat aatccccagc cgccccaagt ttgagaagat ggcagttgct    4500 tcttttccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg gccaaaggtg ggtgggtttc    4740
```

```
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccacccccac tgcaggctta    4920
gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttta aatacataaa    5280
ctacttcaaa tgaggtcgga gaaggtcagt gtttattag cagccataaa accaggtgag    5340
cgagtaccat ttttctctac aagaaaaacg attctgagct ctgcgtaagt ataagttctc    5400
catagcggct gaagctcccc cctggctgcc tgccatctca gctggagtgc agtgccattt    5460
ccttggggtt tctctcacag cagtaatggg acaatacttc acaaaaattc tttcttttcc    5520
tgtcatgtgg gatccctact gtgccctcct ggttttacgt tacccctga ctgttccatt     5580
cagcggtttg gaaagagaaa aagaatttgg aaataaaaca tgtctacgtt atcacctcct    5640
ccagcatttt ggttttaat tatgtcaata actggcttag atttggaaat gagaggggt      5700
tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttatttt cgttcttcca tatcagtctt ctctatgaca attcacatcc     6180
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa ccccttctga gactcatctt    6360
aggaccaaat agggtctatc tgggttttt gttcctgctg ttcctcctgg aaggctatct     6420
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa cccttaagg cattcagaac aactagaatc atagaatggt ttggattgga     6600
aggggcctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
```

```
cccagggtac tgttggcctt tcaggctccc agacccctttg ctgatttgtg tcaagctttt   7200
catccaccag aacccacgct tcctggttaa tacttctgcc ctcacttctg taagcttgtt   7260
tcaggagact tccattcttt aggacagact gtgttacacc tacctgccct attcttgcat   7320
atatacattt cagttcatgt ttcctgtaac aggacagaat atgtattcct ctaacaaaaa   7380
tacatgcaga attcctagtg ccatctcagt agggttttca tggcagtatt agcacatagt   7440
caatttgctg caagtacctt ccaagctgcg gcctcccata atcctgtat ttgggatcag    7500
ttaccttttg gggtaagctt ttgtatctgc agagaccctg ggggttctga tgtgcttcag   7560
ctctgctctg ttctgactgc accatttttct agatcaccca gttgttcctg tacaacttcc  7620
ttgtcctcca tcctttccca gcttgtatct ttgacaaata caggcctatt tttgtgtttg   7680
cttcagcagc catttaattc ttcagtgtca tcttgttctg ttgatgccac tggaacagga   7740
ttttcagcag tcttgcaaag aacatctagc tgaaaacttt ctgccattca atattcttac   7800
cagttcttct tgtttgaggt gagccataaa ttactagaac ttcgtcactg acaagtttat   7860
gcattttatt acttctatta tgtacttact ttgacataac acagacacgc acatattttg   7920
ctgggatttc cacagtgtct ctgtgtcctt cacatggttt tactgtcata cttccgttat   7980
aaccttggca atctgcccag ctgcccatca caagaaaaga gattcctttt ttattacttc   8040
tcttcagcca ataaacaaaa tgtgagaagc ccaaacaaga acttgtgggg caggctgcca   8100
tcaagggaga dacagctgaa gggttgtgta gctcaataga attaagaaat aataaagctg   8160
tgtcagacag ttttgcctga tttatacagg cacgccccaa gccagagagg ctgtctgcca   8220
aggccacctt gcagtccttg gtttgtaaga taagtcatag gtaacttttc tggtgaattg   8280
cgtggagaat catgatggca gttcttgctg tttactatgg taagatgcta aaataggaga   8340
cagcaaagta acacttgctg ctgtaggtgc tctgctatcc agacagcgat ggcactcgca   8400
caccaagatg agggatgctc ccagctgacg gatgctgggg cagtaacagt gggtcccatg   8460
ctgcctgctc attagcatca cctcagccct caccagccca tcagaaggat catcccaagc   8520
tgaggaaagt tgctcatctt cttcacatca tcaaaccttt ggcctgactg atgcctcccg   8580
gatgcttaaa tgtggtcact gacatcttta ttttttctatg atttcaagtc agaacctccg   8640
gatcaggagg gaacacatag tgggaatgta ccctcagctc caaggccaga tcttccttca   8700
atgatcatgc atgctactta ggaaggtgtg tgtgtgtgaa tgtagaattg cctttgttat   8760
ttttttcttcc tgctgtcagg aacatttttga ataccagaga aaaagaaaag tgctcttctt   8820
ggcatgggag gagttgtcac acttgcaaaa taaaggatgc agtcccaaat gttcataatc   8880
tcagggtctg aaggaggatc agaaactgtg tatacaattt caggcttctc tgaatgcagc   8940
ttttgaaagc tgttcctggc cgaggcagta ctagtcagaa ccctcggaaa caggaacaaa   9000
tgtcttcaag gtgcagcagg aggaaacacc ttgcccatca tgaaagtgaa taaccactgc   9060
cgctgaagga atccagctcc tgtttgagca ggtgctgcac actcccacac tgaaacaaca   9120
gttcattttt ataggacttc caggaaggat cttcttctta agcttcttaa ttatggtaca   9180
tctccagttg gcagatgact atgactactg acaggagaat gaggaactag ctgggaatat   9240
ttctgtttga ccaccatgga gtcacccatt tctttactgg tatttggaaa taataattct   9300
gaattgcaaa gcaggagtta gcgaagatct tcatttcttc catgttggtg acagcacagt   9360
tctggctatg aaagtctgct tacaaggaag aggataaaaa tcatagggat aataaatcta   9420
agtttgaaga caatgaggtt ttagctgcat ttgacatgaa gaaattgaga cctctactgg   9480
```

-continued

```
atagctatgg tatttacgtg tcttttgct tagttactta ttgacccag ctgaggtcaa    9540 gtatgaactc aggtctctcg ggctactggc atggattgat tacatacaac tgtaattta     9600 gcagtgattt agggtttatg agtacttttg cagtaaatca tagggttagt aatgttaatc    9660
tcagggaaaa aaaaaaaaag ccaaccctga cagacatccc agctcaggtg gaaatcaagg    9720
atcacagctc agtgcggtcc cagagaacac agggactctt ctcttaggac ctttatgtac    9780
agggcctcaa gataactgat gttagtcaga agactttcca ttctggccac agttcagctg    9840
aggcaatcct ggaatttct ctccgctgca cagttccagt catcccagtt tgtacagttc     9900
tggcactttt tgggtcaggc cgtgatccaa ggagcagaag ttccagctat ggtcagggag    9960
tgcctgaccg tcccaactca ctgcactcaa acaaggcga aaccacaaga gtggcttttg     10020
ttgaaattgc agtgtggccc agaggggctg caccagtact ggattgacca cgaggcaaca    10080
ttaatcctca gcaagtgcaa tttgcagcca ttaaattgaa ctaactgata ctacaatgca    10140
atcagtatca acaagtggtt tggcttggaa gatggagtct aggggctcta caggagtagc    10200
tactctctaa tggagttgca ttttgaagca ggacactgtg aaaagctggc ctcctaaaga    10260
ggctgctaaa cattgggtc aattttccag tgcactttct gaagtgtctg cagttcccca    10320
tgcaaagctg cccaaacata gcacttccaa ttgaatacaa ttatatgcag gcgtactgct    10380
tcttgccagc actgtccttc tcaaatgaac tcaacaaaca atttcaaagt ctagtagaaa    10440
gtaacaagct ttgaatgtca ttaaaaagta tatctgcttt cagtagttca gcttatttat    10500
gcccactaga aacatcttgt acaagctgaa cactggggct ccagattagt ggtaaaacct    10560
actttataca atcatagaat catagaatgg cctgggttgg aagggacccc aaggatcatg    10620
aagatccaac accccgcca caggcagggc caccaacctc cagatctggt actagaccag     10680
gcagcccagg gctccatcca acctggccat gaacacctcc agggatggag catccacaac    10740
ctctctgggc agcctgtgcc agcacctcac caccctctct gtgaagaact tttccctgac    10800
atccaatcta agccttccct ccttgaggtt agatccactc cccttgtgc tatcactgtc     10860 tactcttgta aaaagttgat tctcctcctt tttggaaggt tgcaatgagg tctccttgca    10920
gccttcttct cttctgcagg atgaacaagc ccagctccct cagcctgtct ttataggaga    10980
ggtgctccag ccctctgatc atctttgtgg ccctcctctg acccgctcc aagagctcca     11040 catctttcct gtactggggg ccccaggcct gaatgcagta ctccagatgg ggcctcaaaa    11100
gagcagagta aagagggaca atcaccttcc tcaccctgct ggccagccct cttctgatgg    11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgataccct accccacctg ccactgaatg gctccatggc cccctgcagc    11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttga caactgtaga acagaggaat caaaaggggg    11820
tgggaggaag ttaaaagaag aggcaggtgc aagagagctt gcagtcccgc tgtgtgtacg    11880
```

-continued

```
acactggcaa catgaggtct ttgctaatct tggtgctttg cttcctgccc ctggctgcct    11940
tagggtgcga tctgcctcag acccacagcc tgggcagcag gaggaccctg atgctgctgg    12000
ctcagatgag gagaatcagc ctgtttagct gcctgaagga taggcacgat tttggctttc    12060
ctcaagagga gtttggcaac cagtttcaga aggctgagac catccctgtg ctgcacgaga    12120
tgatccagca gatctttaac ctgtttagca ccaaggatag cagcgctgct gggatgaga    12180 ccctgctgga taagttttac accgagctgt accagcagct gaacgatctg gaggcttgcg    12240
tgatccaggg cgtgggcgtg accgagaccc tctgatgaa ggaggatagc atcctggctg    12300
tgaggaagta ctttcagagg atcaccctgt acctgaagga gaagaagtac agcccctgcg    12360
cttgggaagt cgtgagggct gagatcatga ggagctttag cctgagcacc aacctgcaag    12420
agagcttgag gtctaaggag taaaaagtct agagtcgggg cggccggccg cttcgagcag    12480
acatgataag atacattgat gagtttggac aaaccacaac tagaatgcag tgaaaaaaat    12540
gctttatttg tgaaatttgt gatgctattg ctttatttgt aaccattata agctgcaata    12600
aacaagttaa caacaacaat tgcattcatt ttatgtttca ggttcagggg gaggtgtggg    12660
aggtttttta aagcaagtaa aacctctaca aatgtggtaa aatcgataag gatccgtcga    12720
gcggccgc                                                             12728
```

<210> SEQ ID NO 66
<211> LENGTH: 498
<212> TYPE: DNA
<213> ORGANISM: Artificial Sequence
<220> FEATURE:
<223> OTHER INFORMATION: IFNMAGMAX
<220> FEATURE:
<221> NAME/KEY: misc_feature
<222> LOCATION: (1)..(498)

<400> SEQUENCE: 66

```
tgcgatctgc ctcagaccca cagcctgggc agcaggagga ccctgatgct gctggctcag      60
atgaggagaa tcagcctgtt tagctgcctg aaggataggc acgatttttgg ctttcctcaa    120 gaggagtttg gcaaccagtt tcagaaggct gagaccatcc ctgtgctgca cgagatgatc    180
cagcagatct ttaacctgtt tagcaccaag gatagcagcg ctgcttggga tgagaccctg    240
ctggataagt tttacaccga gctgtaccag cagctgaacg atctggaggc ttgcgtgatc    300
cagggcgtgg gcgtgaccga gacccctctg atgaaggagg atagcatcct ggctgtgagg    360
aagtactttc agaggatcac cctgtacctg aaggagaaga agtacagccc ctgcgcttgg    420
gaagtcgtga gggctgagat catgaggagc tttagcctga gcaccaacct gcaagagagc    480
ttgaggtcta aggagtaa                                                  498
```

<210> SEQ ID NO 67
<211> LENGTH: 11945
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix attachment region (MAR)
<220> FEATURE:
<221> NAME/KEY: misc_feature
<222> LOCATION: (261)..(1564)
<223> OTHER INFORMATION: 5prime matrix attachment region (MAR)
<220> FEATURE:
<221> NAME/KEY: misc_feature
<222> LOCATION: (1565)..(1912)
<223> OTHER INFORMATION: 5prime matrix attachment region (MAR)

```
<220> FEATURE:
<221> NAME/KEY: misc_feature
<222> LOCATION: (1930)..(2012)
<223> OTHER INFORMATION: 5prime matrix attachment region (MAR)
<220> FEATURE:
<221> NAME/KEY: misc_feature
<222> LOCATION: (2013)..(2671)
<223> OTHER INFORMATION: Intrinsically Curved DNA
<220> FEATURE:
<221> NAME/KEY: misc_feature
<222> LOCATION: (5848)..(5934)
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat
<220> FEATURE:
<221> NAME/KEY: misc_feature
<222> LOCATION: (10926)..(11193)
<223> OTHER INFORMATION: Chicken CR1 Repeat
<220> FEATURE:
<221> NAME/KEY: misc_feature
<222> LOCATION: (11424)..(11938)
<223> OTHER INFORMATION: Proximal promoter and lysozyme signal peptide

<400> SEQUENCE: 67
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240 ttttttttt tttttttttt aagtaaggtg ttcttttttc ttagtaaatt ttctactgga     300
ctgtatgttt tgacaggtca gaaacatttc ttcaaaagaa gaacctttg gaaactgtac     360 agccctttc tttcattccc ttttgctttt ctgtgccaat gccttggtt ctgattgcat       420 tatggaaaac gttgatcgga acttgaggtt tttatttata gtgtggcttg aaagcttgga     480
tagctgttgt tacacgagat acctattaa gtttaggcca gcttgatgct ttattttttc       540
cctttgaagt agtgagcgtt ctctggtttt tttcctttga aactggtgag gcttagattt     600
ttctaatggg attttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttttatc    780 tctatgctct gtgtgtacag gtcaaacaga cttcactcct attttattt atagaatttt      840 atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaaagaag aatgaatact ttctaaaata    1080
```

```
ttttggcata ggaagcaagc tgcatggatt tgtttgggac ttaaattatt ttggtaacgg    1140
agtgcatagg ttttaaacac agttgcagca tgctaacgag tcacagcgtt tatgcagaag    1200
tgatgcctgg atgcctgttg cagctgttta cggcactgcc ttgcagtgag cattgcagat    1260
aggggtgggg tgctttgtgt cgtgttccca cacgctgcca cacagccacc tcccggaaca    1320
catctcacct gctgggtact tttcaaacca tcttagcagt agtagatgag ttactatgaa    1380
acagagaagt tcctcagttg gatattctca tgggatgtct ttttcccat gttgggcaaa     1440 gtatgataaa gcatctctat ttgtaaatta tgcacttgtt agttcctgaa tcctttctat    1500
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat ttcagttgta aaagaattcc gcctattcat    1680
accatgtaat gtaattttac accccagtg ctgacacttt ggaatatatt caagtaatag     1740
actttggcct caccctcttg tgtactgtat tttgtaatag aaaatatttt aaactgtgca    1800
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920 aaaaaaaag taatataaaa aggaccaggt gttttacaag tgaaatacat tcctatttgg     1980
taaacagtta cattttatg aagattacca gcgctgctga cttctaaac ataaggctgt      2040 attgtcttcc tgtaccattg catttcctca ttcccaattt gcacaaggat gtctgggtaa    2100
actattcaag aaatggcttt gaaatacagc atgggagctt gtctgagttg gaatgcagag    2160
ttgcactgca aaatgtcagg aaatggatgt ctctcagaat gcccaactcc aaaggatttt    2220
atatgtgtat atagtaagca gtttcctgat tccagcaggc caaagagtct gctgaatgtt    2280
gtgttgccgg agacctgtat ttctcaacaa ggtaagatgg tatcctagca actgcggatt    2340
ttaatacatt ttcagcagaa gtacttagtt aatctctacc tttagggatc gtttcatcat    2400
ttttagatgt tatacttgaa atactgcata acttttagct ttcatgggtt ccttttttc     2460 agcctttagg agactgttaa gcaatttgct gtccaacttt tgtgttggtc ttaaactgca    2520
atagtagttt accttgtatt gaagaaataa agaccatttt tatattaaaa aatacttttg    2580
tctgtcttca ttttgacttg tctgatatcc ttgcagtgcc cattatgtca gttctgtcag    2640
atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata ctttttaaa gtcaacttt     2820 tatcagattt ttttttcatt tggaaatata ttgttttcta gactgcatag cttctgaatc    2880
tgaaatgcag tctgattggc atgaagaagc acagcactct tcatcttact taaacttcat    2940
tttggaatga aggaagttaa gcaagggcac aggtccatga aatagagaca gtgcgctcag    3000
gagaaagtga acctggattt ctttggctag tgttctaaat ctgtagtgag aaagtaaca    3060 cccgattcct tgaaagggct ccagctttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tattttaag tactgtgttg caaacgtctc atctgcaaat     3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
```

```
aagcggtatc agaagagcga ggaaggtaag cagtcttcat atgttttccc tccacgtaaa    3540
gcagtctggg aaagtagcac cccttgagca gagacaagga ataattcag gagcatgtgc     3600 taggagaact tcttgctga attctacttg caagagcttt gatgcctggc ttctggtgcc     3660
ttctgcagca cctgcaaggc ccagagcctg tggtgagctg gagggaaaga ttctgctcaa    3720
gtccaagctt cagcaggtca ttgtctttgc ttcttcccc agcactgtgc agcagagtgg     3780
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggcccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggttttgtaa   4140 agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt ttgagaagat ggcagttgct    4500
tctttcccct tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg gccaaaggtg ggtgggtttc    4740
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccaccccac tgcaggctta     4920 gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttta aatacataaa     5280 ctacttcaaa tgaggtcgga gaaggtcagt gttttattag cagccataaa accaggtgag    5340
cgagtaccat ttttctctac aagaaaaacg attctgagct ctgcgtaagt ataagttctc    5400
catagcggct gaagctcccc cctggctgcc tgccatctca gctggagtgc agtgccattt    5460 ccttgggggtt tctctcacag cagtaatggg acaatacttc acaaaaattc tttcttttcc    5520
tgtcatgtgg gatccctact gtgccctcct ggttttacgt tacccctga ctgttccatt     5580 cagcggtttg gaaagagaaa aagaatttgg aaataaaaca tgtctacgtt atcacctcct    5640
ccagcatttt ggttttaat tatgtcaata actggcttag atttggaaat gagagggggt     5700
tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
```

```
gccagcaggg ccagcacgag ggatggtgca ctgctggcac tatgccacgg cctgcttgtg   5880
actctgagag caactgcttt ggaaatgaca gcacttggtg caatttcctt tgtttcagaa   5940
tgcgtagagc gtgtgcttgg cgacagtttt tctagttagg ccacttcttt tttccttctc   6000
tcctcattct cctaagcatg tctccatgct ggtaatccca gtcaagtgaa cgttcaaaca   6060
atgaatccat cactgtagga ttctcgtggt gatcaaatct ttgtgtgagg tctataaaat   6120
atggaagctt atttattttt cgttcttcca tatcagtctt ctctatgaca attcacatcc   6180
accacagcaa attaaaggtg aaggaggctg gtgggatgaa gagggtcttc tagctttacg   6240
ttcttccttg caaggccaca ggaaaatgct gagagctgta gaatacagcc tggggtaaga   6300
agttcagtct cctgctggga cagctaaccg catcttataa ccccttctga gactcatctt   6360
aggaccaaat agggtctatc tggggttttt gttcctgctg ttcctcctgg aaggctatct   6420
cactatttca ctgctcccac ggttacaaac caaagataca gcctgaattt tttctaggcc   6480
acattacata aatttgacct ggtaccaata ttgttctcta tatagttatt tccttcccca   6540
ctgtgtttaa cccccttaagg cattcagaac aactagaatc atagaatggt ttggattgga   6600
aggggcctta aacatcatcc atttccaacc ctctgccatg ggctgcttgc cacccactgg   6660
ctcaggctgc ccagggcccc atccagcctg gccttgagca cctccaggga tggggcaccc   6720
acagcttctc tgggcagcct gtgccaacac ctcaccactc tctgggtaaa gaattctctt   6780
ttaacatcta atctaaatct cttctctttt agtttaaagc cattcctctt tttcccgttg   6840
ctatctgtcc aagaaatgtg tattggtctc cctcctgctt ataagcagga agtactggaa   6900
ggctgcagtg aggtctcccc acagccttct cttctccagg ctgaacaagc ccagctcctt   6960
cagcctgtct tcgtaggaga tcatcttagt ggccctcctc tggacccatt ccaacagttc   7020
cacggctttc ttgtggagcc ccaggtctgg atgcagtact tcagatgggg ccttacaaag   7080
gcagagcaga tggggacaat cgcttacccc tccctgctgg ctgcccctgt tttgatgcag   7140
cccagggtac tgttggcctt tcaggctccc agacccttg ctgatttgtg tcaagctttt   7200
catccaccag aacccacgct tcctggttaa tacttctgcc ctcacttctg taagcttgtt   7260
tcaggagact tccattcttt aggacagact gtgttacacc tacctgccct attcttgcat   7320
atatacattt cagttcatgt ttcctgtaac aggacagaat atgtattcct ctaacaaaaa   7380
tacatgcaga attcctagtg ccatctcagt agggttttca tggcagtatt agcacatagt   7440
caatttgctg caagtacctt ccaagctgcg gcctcccata aatcctgtat ttgggatcag   7500
ttaccttttg gggtaagctt ttgtatctgc agagaccctg ggggtctga tgtgcttcag   7560 ctctgctctg ttctgactgc accatttct agatcaccca gttgttcctg tacaacttcc   7620
ttgtcctcca tcctttccca gcttgtatct ttgacaaata caggcctatt tttgtgtttg   7680
cttcagcagc catttaattc ttcagtgtca tcttgttctg ttgatgccac tggaacagga   7740
ttttcagcag tcttgcaaag aacatctagc tgaaaacttt ctgccattca atattcttac   7800
cagttcttct tgtttgaggt gagccataaa ttactagaac ttcgtcactg acaagtttat   7860
gcattttatt acttctatta tgtacttact ttgcataac acagacacgc acatattttg   7920
ctgggatttc acagtgtct ctgtgtcctt cacatggttt tactgtcata cttccgttat   7980
aaccttggca atctgcccag ctgcccatca caagaaaaga gattccttt ttattacttc   8040 tcttcagcca ataaacaaaa tgtgagaagc ccaaacaaga acttgtgggg caggctgcca   8100
tcaagggaga gacagctgaa gggttgtgta gctcaataga attaagaaat aataaagctg   8160
tgtcagacag ttttgcctga tttatacagg cacgccccaa gccagagagg ctgtctgcca   8220
```

```
aggccacctt gcagtccttg gtttgtaaga taagtcatag gtaacttttc tggtgaattg      8280
cgtggagaat catgatggca gttcttgctg tttactatgg taagatgcta aaataggaga      8340
cagcaaagta acacttgctg ctgtaggtgc tctgctatcc agacagcgat ggcactcgca      8400
caccaagatg agggatgctc ccagctgacg gatgctgggg cagtaacagt gggtcccatg      8460
ctgcctgctc attagcatca cctcagccct caccagccca tcagaaggat catcccaagc      8520
tgaggaaagt tgctcatctt cttcacatca tcaaaccttt ggcctgactg atgcctcccg      8580
gatgcttaaa tgtggtcact gacatcttta ttttctatg atttcaagtc agaacctccg      8640
gatcaggagg gaacacatag tgggaatgta ccctcagctc caaggccaga tcttccttca      8700
atgatcatgc atgctactta ggaaggtgtg tgtgtgtgaa tgtagaattg cctttgttat      8760
tttttcttcc tgctgtcagg aacattttga ataccagaga aaaagaaaag tgctcttctt      8820
ggcatgggag gagttgtcac acttgcaaaa taaggatgc agtcccaaat gttcataatc      8880
tcagggtctg aaggaggatc agaaactgtg tatacaattt caggcttctc tgaatgcagc      8940
ttttgaaagc tgttcctggc cgaggcagta ctagtcagaa ccctcggaaa caggaacaaa      9000
tgtcttcaag gtgcagcagg aggaaacacc ttgcccatca tgaaagtgaa taaccactgc      9060
cgctgaagga atccagctcc tgtttgagca ggtgctgcac actcccacac tgaaacaaca      9120 gttcatttt ataggacttc caggaaggat cttcttctta agcttcttaa ttatggtaca      9180
tctccagttg gcagatgact atgactacta acaggagaat gaggaactag ctgggaatat      9240
ttctgtttga ccaccatgga gtcacccatt tctttactgg tatttggaaa taataattct      9300
gaattgcaaa gcaggagtta gcgaagatct tcatttcttc catgttggtg acagcacagt      9360
tctggctatg aaagtctgct tacaaggaag aggataaaaa tcatagggat aataaatcta      9420
agtttgaaga caatgaggtt ttagctgcat ttgacatgaa gaaattgaga cctctactgg      9480
atagctatgg tatttacgtg tctttttgct tagttactta ttgaccccag ctgaggtcaa      9540
gtatgaactc aggtctctcg ggctactggc atggattgat tacatacaac tgtaattta      9600 gcagtgattt agggtttatg agtacttttg cagtaaatca tagggttagt aatgttaatc      9660
tcagggaaaa aaaaaaaag ccaaccctga cagacatccc agctcaggtg gaaatcaagg      9720
atcacagctc agtgcggtcc cagagaacac agggactctt ctcttaggac ctttatgtac      9780
agggcctcaa gataactgat gttagtcaga agactttcca ttctggccac agttcagctg      9840
aggcaatcct ggaattttct ctccgctgca cagttccagt catcccagtt tgtacagttc      9900
tggcactttt tgggtcaggc cgtgatccaa ggagcagaag ttccagctat ggtcagggag      9960
tgcctgaccg tcccaactca ctgcactcaa acaaaggcga aaccacaaga gtggcttttg      10020
ttgaaattgc agtgtggccc agaggggctg caccagtact ggattgacca cgaggcaaca      10080
ttaatcctca gcaagtgcaa tttgcagcca ttaaattgaa ctaactgata ctacaatgca      10140
atcagtatca acaagtggtt tggcttggaa gatggagtct aggggctcta caggagtagc      10200
tactctctaa tggagttgca ttttgaagca ggacactgtg aaaagctggc ctcctaaaga      10260
ggctgctaaa cattagggtc aattttccag tgcactttct gaagtgtctg cagttcccca      10320
tgcaaagctg cccaaacata gcacttccaa ttgaatacaa ttatatgcag gcgtactgct      10380
tcttgccagc actgtccttc tcaaatgaac tcaacaaaca atttcaaagt ctagtagaaa      10440
gtaacaagct ttgaatgtca ttaaaaagta tatctgcttt cagtagttca gcttatttat      10500
gcccactaga aacatcttgt acaagctgaa cactgggggct ccagattagt ggtaaaacct      10560
```

-continued

```
actttataca atcatagaat catagaatgg cctgggttgg aagggacccc aaggatcatg    10620
aagatccaac accccccgcca caggcagggc caccaacctc cagatctggt actagaccag    10680
gcagcccagg gctccatcca acctggccat gaacacctcc agggatggag catccacaac    10740
ctctctgggc agcctgtgcc agcacctcac caccctctct gtgaagaact tttccctgac    10800
atccaatcta agccttccct ccttgaggtt agatccactc ccccttgtgc tatcactgtc    10860
tactcttgta aaaagttgat tctcctcctt tttggaaggt tgcaatgagg tctccttgca    10920
gccttcttct cttctgcagg atgaacaagc ccagctccct cagcctgtct ttataggaga    10980
ggtgctccag ccctctgatc atctttgtgg ccctcctctg gacccgctcc aagagctcca    11040
catctttcct gtactggggg ccccaggcct gaatgcagta ctccagatgg ggcctcaaaa    11100
gagcagagta aagagggaca atcaccttcc tcaccctgct ggccagccct cttctgatgg    11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgatacctc accccacctg ccactgaatg gctccatggc ccctgcagc    11400 cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttga caactgtaga acagaggaat caaaaggggg    11820
tgggaggaag ttaaaagaag aggcaggtgc aagagagctt gcagtcccgc tgtgtgtacg    11880
acactggcaa catgaggtct tgctaatct tggtgctttg cttcctgccc ctggctgcct    11940
taggg                                                              11945
```

<210> SEQ ID NO 68
<211> LENGTH: 285
<212> TYPE: DNA
<213> ORGANISM: SV40
<220> FEATURE:
<221> NAME/KEY: misc_feature
<222> LOCATION: (1)..(285)
<223> OTHER INFORMATION: SV40 Polyadenylation Sequence

<400> SEQUENCE: 68

```
aaagtctaga gtcggggcgg ccggccgctt cgagcagaca tgataagata cattgatgag     60
tttggacaaa ccacaactag aatgcagtga aaaaaatgct ttatttgtga aatttgtgat    120
gctattgctt tatttgtaac cattataagc tgcaataaac aagttaacaa caacaattgc    180
attcatttta tgtttcaggt tcaggggag gtgtgggagg ttttttaaag caagtaaaac    240
ctctacaaat gtggtaaaat cgataaggat ccgtcgagcg gccgc                   285
```

<210> SEQ ID NO 69
<211> LENGTH: 5972
<212> TYPE: DNA
<213> ORGANISM: Gallus gallus

<400> SEQUENCE: 69

```
cgcgtggtag gtggcggggg gttcccagga gagcccccag cgcggacggc agcgccgtca     60
```

-continued

```
ctcaccgctc cgtctccctc cgcccagggt cgcctggcgc aaccgctgca agggcaccga    120
cgtccaggcg tggatcagag gctgccggct gtgaggagct gccgcgcccg gcccgcccgc    180
tgcacagccg gccgctttgc gagcgcgacg ctacccgctt ggcagtttta aacgcatccc    240
tcattaaaac gactatacgc aaacgccttc ccgtcggtcc gcgtctcttt ccgccgccag    300
ggcgacactc gcggggaggg cgggaagggg gccgggcggg agcccgcggc caaccgtcgc    360
cccgtgacgg caccgccccg ccccgtgacg cggtgcggg cgccggggcc gtgggctga     420 gcgctgcggc ggggccgggc cgggccgggg cgggagctga gcgcggcgcg gctgcgggcg    480 gcgcccctc cggtgcaata tgttcaagag aatggctgag ttcgggcctg actccggggg    540
cagggtgaag gtgcggcgcg ggcggaggga cgggcgggc gcggggccgc ccggcgggtg     600
ccggggcctc tgccggcccg cccggctcgg gctgctgcgg cgcttacggg cgcgcttctc    660
gccgctgccg cttctcttct ctcccgcgca agggcgtcac catcgtgaag ccggtagtgt    720
acgggaacgt ggcgcggtac ttcgggaaga agagggagga ggacgggcac acgcatcagt    780
ggacggttta cgtgaagccc tacaggaacg aggtagggcc cgagcgcgtc ggccgccgtt    840
ctcggagcgc cggagccgtc agcgccgcgc ctgggtgcgc tgtgggacac agcgagcttc    900
tctcgtagga catgtccgcc tacgtgaaaa aaatccagtt caagctgcac gagagctacg    960
ggaatcctct ccgaggtggg tgttgcgtcg ggggtttgc tccgctcggt cccgctgagg    1020
ctcgtcgccc tcatctttct ttcgtgccgc agtcgttacc aaaccgccgt acgagatcac    1080
cgaaacgggc tgggcgaat ttgaaatcat catcaagata ttttcattg atccaaacga     1140 gcgacccgta agtacgctca gcttctcgta gtgcttcccc cgtcctggcg gcccgggct    1200 gggctgctcg ctgctgccgg tcacagtccc gccagccgcg gagctgactg agctcccttt    1260
cccgggacgt gtgctctgtg ttcggtcagc gaggctatcg ggagggcttt ggctgcattt    1320
ggcttctctg gcgcttagcg caggagcacg ttgtgctacg cctgaactac agctgtgaga    1380
aggccgtgga aaccgctctc aaactgattt attggcgaaa tggctctaaa ctaaatcgtc    1440
tcctctcttt ggaaatgctt tagagaaggt ctctgtggta gttcttatgc atctatccta    1500
aagcacttgg ccagacaatt taaagacatc aagcagcatt tatagcaggc acgtttaata    1560
acgaatactg aatttaagta actctgctca cgttgtatga cgtttatttt cgtattcctg    1620
aaagccatta aaatcctgtg cagttgttta gtaagaacag ctgccactgt tttgtatcta    1680
ggagataact ggtgtttccc tacagttctc aagctgataa aactctgtct ttgtatctag    1740
gtaaccctgt atcacttgct gaagcttttt cagtctgaca ccaatgcaat cctgggaaag    1800
aaaactgtag tttctgaatt ctatgatgaa atggtatgaa aattttaatg tcaaccgagc    1860
ctgactttat ttaaaaaaa ttattgatgg tgctgtgtat tttggtcctt ccttagatat     1920
ttcaagatcc tactgccatg atgcagcaac tgctaacgac gtcccgtcag ctgacacttg    1980
gtgcttacaa gcatgaaaca gagtgtaagt gcaaaatgag gataccttcg ccgaccgtca    2040
ttcactacta atgttttctg tgggatgtga tcgtacagtg agtttggctg tgtgaaattt    2100
gaatagcttg gtattggcag tgatgacgtg atcgatgcct tgcttatcat gtttgaaatg    2160
aagtagaata aatgcagcct gctttatttg agatagtttg gttcatttta tggaatgcaa    2220
gcaaagatta tacttcctca ctgaattgca ctgtccaaag gtgtgaaatg tgtggggatc    2280
tggaggaccg tgaccgaggg acattggatc gctatctccc atttcttttg ctgttaccag    2340
ttcagatttt cttttcacct agtctttaat tcccaggggtt ttgttttttc cttggtcata   2400
```

```
gtttttgttt ttcactctgg caaatgatgt tgtgaattac actgcttcag ccacaaaact    2460
gatggactga atgaggtcat caaacaaact tttcttcttc cgtatttcct ttttttttcc    2520
ccacttatca ttttttactgc tgttgttgag tctgtaaggc taaaagtaac tgttttgtgc   2580
tttttcagga cgtgtgcttt ccaaattact gccacatata taaagaaagg ttggaatttt    2640
aaagataatt catgtttctt cttcttttt gccaccacag ttgcagatct tgaagtaaaa     2700
accagggaaa agctggaagc tgccaaaaag aaaaccagtt tgaaattgc tgagcttaaa     2760
gaaaggttaa aagcaagtcg tgaaaccatc aactgcttaa agagtgaaat cagaaaactc    2820
gaagaggatg atcagtctaa agatatgtga tgagtgttga cttggcaggg agcctataat    2880
gagaatgaaa ggacttcagt cgtggagttg tatgcgttct ctccaattct gtaacggaga    2940
ctgtatgaat tcatttgca aatcactgca gtgtgtgaca actgacttt tataaatggc      3000
agaaaacaag aatgaatgta tcctcatttt atagttaaaa tctatgggta tgtactggtt   3060
tatttcaagg agaatggatc gtagagactt ggaggccaga ttgctgcttg tattgactgc   3120
atttgagtgg tgtaggaaca ttttgtctat ggtcccgtgt tagtttacag aatgccactg   3180
ttcactgttt tgttttgtat tttacttttt ctactgcaac gtcaaggttt taaaagttga   3240
aaataaaaca tgcaggtttt ttttaaatat ttttttgtct ctatccagtt tgggcttcaa   3300
gtattattgt taacagcaag tcctgattta agtcagaggc tgaagtgtaa tggtattcaa   3360
gatgcttaag tctgttgtca gcaaaacaaa agagaaaact tcataaaatc aggaagttgg   3420
catttctaat aacttcttta tcaacagata agagtttcta gccctgcatc tacttttcact  3480
tatgtagttg atgcctttat attttgtgtg tttggatgca ggaagtgatt cctactctgt   3540
tatgtagata ttctatttaa cacttgtact ctgctgtgct tagcctttcc ccatgaaaat   3600
tcagcggctg taaatccccc tcttctttttg tagcctcata cagatggcag accctcaggc  3660
ttataaaggc ttgggcatct tctttactgc tttgagattc tgtgttgcag taacctctgc   3720
cagagaggag aaaagcccca caaacctcat cccttcttc tatagcaatc agtattacta    3780
atgctttgag aacagagcac tggtttgaaa cgtttgataa ttagcattta acatggcttg   3840
gtaaagatgc agaactgaaa cagctgtgac agtatgaact cagtatggag acttcattaa   3900
gacaaacagc tgttaaaatc aggcatgttt cattgaggag gacggggcaa cttgcaccag   3960
tggtgcccac acaaatcctt cctggcgctg cagaccaatt tttctggcat tctgactgcc   4020
gttgctgctg tcacagaga gcaactattt ttatcagcca caggcaattt gcttgtagta    4080
ttttccaagt gttgtaggta agtataaatg catcggctcc agagcacttt gagtatactt   4140
attaaaaaca taaatgaaag acaaattagc tttgcttggg tgcacagaac atttttagtt   4200
ccagcctgct ttttggtaga agccctcttc tgaggctaga actgactttg acaagtagag   4260
aaactggcaa cggagctatt gctatcgaag gatccttgtt aacaaagtta atcgtctttt   4320
aaggtttggt ttattcatta aatttgcttt taagctgtag ctgaaaaaga acgtgctgtc   4380
ttccatgcac caggtggcag ctctgtgcaa agtgctctct ggtctcacca gccttttaat   4440
tgccgggatt ctggcacgtc tgagagggct cagactggct tcgtttgttt gaacagcgtg   4500
tactgctttc tgtagacatg gccggtttct ctcctgcagc ttatgaaact gttcacactg   4560
aacacactgg aacaggttgc ccaaggaggc cgtggatgcc ccatccctgg aggcattcaa   4620
ggccaggctg gatgtggctc tgggcagcct ggtctggtgg ttggcgatcc tgcacatagc   4680
agcggggttg aaactcgatg atcactgtgg tccttttcaa cccaggctat tctatgattc   4740
tatgattcaa cagcaaatca tatgtactga gagaggaaac aaacacaagt gctactgttt   4800
```

```
gcaagttttg ttcatttggt aaaagagtca ggttttaaaa ttcaaaatct gtctggtttt      4860
ggtgtttttt ttttttttatt tattatttct ttggggttct ttttgatgct ttatctttct      4920
ctgccaggac tgtgtgacaa tgggaacgaa aaagaacatg ccaggcactg tcctggattg      4980
cacacgctgg ttgcactcag tagcaggctc agaactgcca gtctttccac agtattactt      5040
tctaaaccta attttaatag cgttagtaga cttccatcac tggcagtgc ttagtgaatg       5100 ctctgtgtga acgttttact tataagcatg ttggaagttt tgatgttcct ggatgcagta      5160
gggaaggaca gattagctat gtgaaaagta gattctgagt atcggggtta caaaaagtat      5220
agaaacgatg agaaattctt gttgtaacta attggaattt ctttaagcgt tcacttatgc      5280
tacattcata gtatttccat ttaaaagtag gaaaaggtaa aacgtgaaat cgtgtgatt       5340 tcggatggaa caccgccttc ctatgcacct gaccaacttc cagaggaaaa gcctattgaa      5400
agccgagatt aagccaccaa agaactcat ttgcattgga atatgtagta tttgccctct       5460
tcctcccggg taattactat actttatagg gtgcttatat gttaaatgag tggctggcac      5520
tttttattct cacagctgtg gggaattctg tcctctagga cagaaacaat tttaatctgt      5580
tccactggtg actgctttgt cagcacttcc acctgaagag atcaatacac tcttcaatgt      5640
ctagttctgc aacacttggc aaacctcaca tcttatttca tactctcttc atgcctatgc      5700
ttattaaagc aataatctgg gtaattttg ttttaatcac tgtcctgacc ccagtgatga       5760
ccgtgtccca cctaaagctc aattcaggtc ctgaatctct tcaactctct atagctaaca      5820
tgaagaatct tcaaaagtta ggtctgaggg acttaaggct aactgtagat gttgttgcct      5880
ggtttctgtg ctgaaggccg tgtagtagtt agagcattca acctctagaa gaagcttggc      5940
cagctggtcg acctgcagat ccggccctcg ag                                    5972

<210> SEQ ID NO 70
<211> LENGTH: 18391
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
      (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription enhancer
<220> FEATURE:
<221> NAME/KEY: misc_feature
<222> LOCATION: (9160)..(9325)
<223> OTHER INFORMATION: Transcription enhancer
<220> FEATURE:
```

```
<221> NAME/KEY: misc_feature
<222> LOCATION: (9326)..(9626)
<223> OTHER INFORMATION: Negative regulatory element
<220> FEATURE:
<221> NAME/KEY: misc_feature
<222> LOCATION: (9621)..(9660)
<223> OTHER INFORMATION: Hormone response element
<220> FEATURE:
<221> NAME/KEY: misc_feature
<222> LOCATION: (9680)..(10060)
<223> OTHER INFORMATION: Hormone response element
<220> FEATURE:
<221> NAME/KEY: misc_feature
<222> LOCATION: (10576)..(10821)
<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
      Peptide
<220> FEATURE:
<221> NAME/KEY: misc_feature
<222> LOCATION: (11846)..(12443)
<223> OTHER INFORMATION: Human Interferon alpha 2b encoding region
      codon optimized for exp ression in chicken cells (IFNMAGMAX)
<220> FEATURE:
<221> NAME/KEY: misc_feature
<222> LOCATION: (12464)..(18391)
<223> OTHER INFORMATION: Chicken Lysozyme 3prime domain

<400> SEQUENCE: 70
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240 ttttttttt  tttttttttt aagtaaggtg ttcttttttc ttagtaaatt ttctactgga     300
ctgtatgttt tgacaggtca gaaacatttc tcaaaagaa  gaaccttttg gaaactgtac     360
agcccttttc tttcattccc ttttgctttt ctgtgccaat gcctttggtt ctgattgcat     420
tatggaaaac gttgatcgga acttgaggtt tttatttata gtgtggcttg aaagcttgga     480
tagctgttgt tacacgagat accttattaa gtttaggcca gcttgatgct ttatttttc      540 cctttgaagt agtgagcgtt ctctggtttt tttcctttga aactggtgag gcttagattt     600
ttctaatggg atttttacc  tgatgatcta gttgcatacc caaatgcttg taaatgtttt     660
cctagttaac atgttgataa cttcggattt acatgttgta tacttgtc   atctgtgttt     720 ctagtaaaaa tatatggcat ttatagaaat acgtaattcc tgatttcctt tttttttatc     780
tctatgctct gtgtgtacag gtcaaacaga cttcactcct attttttattt atagaatttt    840 atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaagaag  aatgaatact ttctaaaata    1080
ttttggcata ggaagcaagc tgcatggatt tgtttgggac ttaaattatt ttggtaacgg    1140
agtgcatagg ttttaaacac agttgcagca tgctaacgag tcacagcgtt tatgcagaag    1200
tgatgcctgg atgcctgttg cagctgttta cggcactgcc ttgcagtgag cattgcagat    1260
aggggtgggg tgctttgtgt cgtgttccca cacgctgcca cacagccacc tcccggaaca    1320
```

```
catctcacct gctgggtact tttcaaacca tcttagcagt agtagatgag ttactatgaa   1380
acagagaagt tcctcagttg gatattctca tgggatgtct ttttcccat gttgggcaaa    1440
gtatgataaa gcatctctat ttgtaaatta tgcacttgtt agttcctgaa tcctttctat   1500
agcaccactt attgcagcag gtgtaggctc tggtgtggcc tgtgtctgtg cttcaatctt   1560
ttaaagcttc tttggaaata cactgacttg attgaagtct cttgaagata gtaaacagta   1620
cttacctttg atcccaatga aatcgagcat tcagttgta aaagaattcc gcctattcat    1680
accatgtaat gtaattttac accccagtg ctgacacttt ggaatatatt caagtaatag    1740
actttggcct caccctcttg tgtactgtat tttgtaatag aaaatatttt aaactgtgca   1800
tatgattatt acattatgaa agagacattc tgctgatctt caaatgtaag aaaatgagga   1860
gtgcgtgtgc ttttataaat acaagtgatt gcaaattagt gcaggtgtcc ttaaaaaaaa   1920
aaaaaaaag taatataaaa aggaccaggt gttttacaag tgaaatacat tcctatttgg    1980
taaacagtta cattttatg aagattacca gcgctgctga cttctaaac ataaggctgt     2040
attgtcttcc tgtaccattg catttcctca ttcccaattt gcacaaggat gtctgggtaa   2100
actattcaag aaatggcttt gaaatacagc atgggagctt gtctgagttg gaatgcagag   2160
ttgcactgca aaatgtcagg aaatggatgt ctctcagaat gcccaactcc aaaggatttt   2220
atatgtgtat atagtaagca gtttcctgat tccagcaggc caaagagtct gctgaatgtt   2280
gtgttgccgg agacctgtat ttctcaacaa ggtaagatgg tatcctagca actgcggatt   2340
ttaatacatt ttcagcagaa gtacttagtt aatctctacc tttagggatc gtttcatcat   2400
ttttagatgt tatacttgaa atactgcata acttttagct ttcatgggtt ccttttttc    2460
agcctttagg agactgttaa gcaatttgct gtccaacttt tgtgttggtc ttaaactgca   2520
atagtagttt accttgtatt gaagaaataa agaccatttt tatattaaaa aatactttg   2580
tctgtcttca ttttgacttg tctgatatcc ttgcagtgcc cattatgtca gttctgtcag   2640
atattcagac atcaaaactt aacgtgagct cagtggagtt acagctgcgg ttttgatgct   2700
gttattattt ctgaaactag aaatgatgtt gtcttcatct gctcatcaaa cacttcatgc   2760
agagtgtaag gctagtgaga aatgcataca tttattgata cttttttaaa gtcaacttt    2820
tatcagattt ttttttcatt tggaaatata ttgttttcta gactgcatag cttctgaatc   2880
tgaaatgcag tctgattggc atgaagaagc acagcactct tcatcttact taaacttcat   2940
tttggaatga aggaagttaa gcaagggcac aggtccatga aatagagaca gtgcgctcag   3000
gagaaagtga acctggattt ctttggctag tgttctaaat ctgtagtgag aaagtaaca    3060
cccgattcct tgaaagggct ccagctttaa tgcttccaaa ttgaaggtgg caggcaactt   3120
ggccactggt tatttactgc attatgtctc agtttcgcag ctaacctggc ttctccacta   3180
ttgagcatgg actatagcct ggcttcagag gccaggtgaa ggttgggatg ggtggaagga   3240
gtgctgggct gtggctgggg ggactgtggg gactccaagc tgagcttggg gtgggcagca   3300
cagggaaaag tgtgggtaac tattttaag tactgtgttg caaacgtctc atctgcaaat    3360
acgtagggtg tgtactctcg aagattaaca gtgtgggttc agtaatatat ggatgaattc   3420
acagtggaag cattcaaggg tagatcatct aacgacacca gatcatcaag ctatgattgg   3480
aagcggtatc agaagagcga ggaaggtaag cagtcttcat atgttttccc tccacgtaaa   3540
gcagtctggg aaagtagcac cccttgagca gagacaagga aataattcag gagcatgtgc   3600
taggagaact ttcttgctga attctacttg caagagcttt gatgcctggc ttctggtgcc   3660
```

```
ttctgcagca cctgcaaggc ccagagcctg tggtgagctg gagggaaaga ttctgctcaa   3720
gtccaagctt cagcaggtca ttgtctttgc ttcttcccc agcactgtgc agcagagtgg    3780
aactgatgtc gaagcctcct gtccactacc tgttgctgca ggcagactgc tctcagaaaa   3840
agagagctaa ctctatgcca tagtctgaag gtaaaatggg ttttaaaaaa gaaaacacaa   3900
aggcaaaacc ggctgcccca tgagaagaaa gcagtggtaa acatggtaga aaaggtgcag   3960
aagcccccag gcagtgtgac aggcccctcc tgccacctag aggcgggaac aagcttccct   4020
gcctagggct ctgcccgcga agtgcgtgtt tctttggtgg gttttgtttg gcgtttggtt   4080
ttgagattta gacacaaggg aagcctgaaa ggaggtgttg ggcactattt tggtttgtaa   4140
agcctgtact tcaaatatat attttgtgag ggagtgtagc gaattggcca atttaaaata   4200
aagttgcaag agattgaagg ctgagtagtt gagagggtaa cacgtttaat gagatcttct   4260
gaaactactg cttctaaaca cttgtttgag tggtgagacc ttggataggt gagtgctctt   4320
gttacatgtc tgatgcactt gcttgtcctt ttccatccac atccatgcat tccacatcca   4380
cgcatttgtc acttatccca tatctgtcat atctgacata cctgtctctt cgtcacttgg   4440
tcagaagaaa cagatgtgat aatccccagc cgccccaagt tgagaagat ggcagttgct    4500
tctttccctt tttcctgcta agtaaggatt ttctcctggc tttgacacct cacgaaatag   4560
tcttcctgcc ttacattctg ggcattattt caaatatctt tggagtgcgc tgctctcaag   4620
tttgtgtctt cctactctta gagtgaatgc tcttagagtg aaagagaagg aagagaagat   4680
gttggccgca gttctctgat gaacacacct ctgaataatg ccaaaggtg ggtgggtttc    4740
tctgaggaac gggcagcgtt tgcctctgaa agcaaggagc tctgcggagt gcagttatt    4800
ttgcaactga tggtggaact ggtgcttaaa gcagattccc taggttccct gctacttctt   4860
ttccttcttg gcagtcagtt tatttctgac agacaaacag ccaccccac tgcaggctta    4920
gaaagtatgt ggctctgcct gggtgtgtta cagctctgcc ctggtgaaag gggattaaaa   4980
cgggcaccat tcatcccaaa caggatcctc attcatggat caagctgtaa ggaacttggg   5040
ctccaacctc aaaacattaa ttggagtacg aatgtaatta aaactgcatt ctcgcattcc   5100
taagtcattt agtctggact ctgcagcatg taggtcggca gctcccactt tctcaaagac   5160
cactgatgga ggagtagtaa aaatggagac cgattcagaa caaccaacgg agtgttgccg   5220
aagaaactga tggaaataat gcatgaattg tgtggtggac attttttta aatacataaa    5280
ctacttcaaa tgaggtcgga gaaggtcagt gttttattag cagccataaa accaggtgag   5340
cgagtaccat ttttctctac aagaaaaacg attctgagct ctgcgtaagt ataagttctc   5400
catagcggct gaagctcccc cctggctgcc tgccatctca gctggagtgc agtgccattt   5460
ccttggggtt tctctcacag cagtaatggg acaatacttc acaaaaattc tttcttttcc   5520
tgtcatgtgg gatccctact gtgccctcct ggttttacgt tacccctga ctgttccatt    5580
cagcggtttg gaaagagaaa aagaatttgg aaataaaaca tgtctacgtt atcacctcct   5640
ccagcatttt ggttttaat tatgtcaata actggcttag atttggaaat gagaggggt     5700
tgggtgtatt accgaggaac aaaggaaggc ttatataaac tcaagtcttt tatttagaga   5760
actggcaagc tgtcaaaaac aaaaaggcct taccaccaaa ttaagtgaat agccgctata   5820
gccagcaggg ccagcacgag ggatggtgca ctgctggcac tatgccacgg cctgcttgtg   5880
actctgagag caactgcttt ggaaatgaca gcacttggtg caatttcctt tgtttcagaa   5940
tgcgtagagc gtgtgcttgg cgacagtttt tctagttagg ccacttcttt ttccttctc    6000
tcctcattct cctaagcatg tctccatgct ggtaatccca gtcaagtgaa cgttcaaaca   6060
```

```
atgaatccat cactgtagga ttctcgtggt gatcaaatct ttgtgtgagg tctataaaat    6120
atggaagctt atttattttt cgttcttcca tatcagtctt ctctatgaca attcacatcc    6180
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa ccccttctga gactcatctt    6360
aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa ccccttaagg cattcagaac aactagaatc atagaatggt ttggattgga    6600
aggggcctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agacccttg ctgatttgtg tcaagctttt    7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata aatcctgtat ttgggatcag    7500 ttacctttttg gggtaagctt ttgtatctgc agagaccctg ggggttctga tgtgcttcag    7560
ctctgctctg ttctgactgc accattttct agatcaccca gttgttcctg tacaacttcc    7620
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca aagaaaaga gattcctttt ttattacttc    8040
tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccacctt gcagtccttg gtttgtaaga taagtcatag gtaacttttc tggtgaattg    8280
cgtggagaat catgatggca gttccttgctg tttactatgg taagatgcta aaataggaga    8340
cagcaaagta acacttgctg ctgtaggtgc tctgctatcc agacagcgat ggcactcgca    8400
```

-continued

```
caccaagatg agggatgctc ccagctgacg gatgctgggg cagtaacagt gggtcccatg    8460
ctgcctgctc attagcatca cctcagccct caccagccca tcagaaggat catcccaagc    8520
tgaggaaagt tgctcatctt cttcacatca tcaaacettt ggcctgactg atgcctcccg    8580
gatgcttaaa tgtggtcact gacatcttta tttttctatg atttcaagtc agaacctccg    8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760
tttttcttcc tgctgtcagg aacattttga ataccagaga aaagaaaag tgctcttctt     8820 ggcatgggag gagttgtcac acttgcaaaa taaaggatgc agtcccaaat gttcataatc    8880
tcagggtctg aaggaggatc agaaactgtg tatacaattt caggcttctc tgaatgcagc    8940
ttttgaaagc tgttcctggc cgaggcagta ctagtcagaa ccctcggaaa caggaacaaa    9000
tgtcttcaag gtgcagcagg aggaaacacc ttgcccatca tgaaagtgaa taaccactgc    9060
cgctgaagga atccagctcc tgtttgagca ggtgctgcac actcccacac tgaaacaaca    9120
gttcattttt ataggacttc caggaaggat cttcttctta agcttcttaa ttatggtaca    9180
tctccagttg gcagatgact atgactactg acaggagaat gaggaactag ctgggaatat    9240
ttctgtttga ccaccatgga gtcacccatt tctttactgg tatttggaaa taataattct    9300
gaattgcaaa gcaggagtta gcgaagatct tcatttcttc catgttggtg acagcacagt    9360
tctggctatg aaagtctgct tacaaggaag aggataaaaa tcatagggat aataaatcta    9420
agtttgaaga caatgaggtt ttagctgcat ttgacatgaa gaaattgaga cctctactgg    9480
atagctatgg tatttacgtg tcttttttgct tagttactta ttgaccccag ctgaggtcaa    9540
gtatgaactc aggtctctcg ggctactggc atggattgat tacatacaac tgtaatttta    9600
gcagtgattt agggtttatg agtacttttg cagtaaatca tagggttagt aatgttaatc    9660
tcagggaaaa aaaaaaaag ccaaccctga cagacatccc agctcaggtg gaaatcaagg     9720
atcacagctc agtgcggtcc cagagaacac agggactctt ctcttaggac ctttatgtac    9780
agggcctcaa gataactgat gttagtcaga agactttcca ttctggccac agttcagctg    9840
aggcaatcct ggaattttct ctccgctgca cagttccagt catcccagtt tgtacagttc    9900
tggcactttt tgggtcaggc cgtgatccaa ggagcagaag ttccagctat ggtcagggag    9960
tgcctgaccg tcccaactca ctgcactcaa acaaaggcga aaccacaaga gtggcttttg   10020
ttgaaattgc agtgtggccc agaggggctg caccagtact ggattgacca cgaggcaaca   10080
ttaatcctca gcaagtgcaa tttgcagcca ttaaattgaa ctaactgata ctacaatgca   10140
atcagtatca acaagtggtt tggcttggaa gatggagtct aggggctcta caggagtagc   10200
tactctctaa tggagttgca ttttgaagca ggacactgtg aaaagctggc ctcctaaaga   10260
ggctgctaaa cattagggtc aattttccag tgcactttct gaagtgtctg cagttcccca   10320
tgcaaagctg cccaaacata gcacttccaa ttgaatacaa ttatatgcag gcgtactgct   10380
tcttgccagc actgtccttc tcaaatgaac tcaacaaaca atttcaaagt ctagtagaaa   10440
gtaacaagct ttgaatgtca ttaaaaagta tatctgcttt cagtagttca gcttatttat   10500
gcccactaga aacatcttgt acaagctgaa cactggggct ccagattagt ggtaaaacct   10560
actttataca atcatagaat catagaatgg cctgggttgg aagggacccc aaggatcatg   10620
aagatccaac accccgcca caggcagggc caccaacctc cagatctggt actagaccag    10680
gcagcccagg gctccatcca acctggccat gaacacctcc agggatggag catccacaac   10740
ctctctgggc agcctgtgcc agcacctcac caccctctct gtgaagaact tttccctgac   10800
```

```
atccaatcta agccttccct ccttgaggtt agatccactc ccccttgtgc tatcactgtc   10860
tactcttgta aaaagttgat tctcctcctt tttggaaggt tgcaatgagg tctccttgca   10920
gccttcttct cttctgcagg atgaacaagc ccagctccct cagcctgtct ttataggaga   10980
ggtgctccag ccctctgatc atctttgtgg ccctcctctg acccgctcc aagagctcca    11040
catctttcct gtactggggg ccccaggcct gaatgcagta ctccagatgg ggcctcaaaa   11100
gagcagagta aagagggaca atcaccttcc tcaccctgct ggccagccct cttctgatgg   11160
agccctggat acaactggct ttctgagctg caacttctcc ttatcagttc cactattaaa   11220
acaggaacaa tacaacaggt gctgatggcc agtgcagagt ttttcacact tcttcatttc   11280
ggtagatctt agatgaggaa cgttgaagtt gtgcttctgc gtgtgcttct tcctcctcaa   11340
atactcctgc ctgatacctc accccacctg ccactgaatg gctccatggc ccctgcagc    11400
cagggccctg atgaacccgg cactgcttca gatgctgttt aatagcacag tatgaccaag   11460
ttgcacctat gaatacacaa acaatgtgtt gcatccttca gcacttgaga agaagagcca   11520
aatttgcatt gtcaggaaat ggtttagtaa ttctgccaat taaaacttgt ttatctacca   11580
tggctgtttt tatggctgtt agtagtggta cactgatgat gaacaatggc tatgcagtaa   11640
aatcaagact gtagatattg caacagacta taaaattcct ctgtggctta gccaatgtgg   11700
tacttcccac attgtataag aaatttggca agtttagagc aatgtttgaa gtgttgggaa   11760
atttctgtat actcaagagg gcgttttga caactgtaga acagaggaat caaaagggg     11820
tgggaggaag ttaaaagaag aggcaggtgc aagagagctt gcagtcccgc tgtgtgtacg   11880
acactggcaa catgaggtct ttgctaatct tggtgctttg cttcctgccc ctggctgcct   11940
tagggtgcga tctgcctcag acccacagcc tgggcagcag gaggaccctg atgctgctgg   12000
ctcagatgag gagaatcagc ctgtttagct gcctgaagga taggcacgat tttggctttc   12060
ctcaagagga gtttggcaac cagtttcaga aggctgagac catccctgtg ctgcacgaga   12120
tgatccagca gatctttaac ctgtttagca ccaaggatag cagcgctgct tgggatgaga   12180
ccctgctgga taagttttac accgagctgt accagcagct gaacgatctg gaggcttgcg   12240
tgatccaggg cgtgggcgtg accgagaccc ctctgatgaa ggaggatagc atcctggctg   12300
tgaggaagta ctttcagagg atcaccctgt acctgaagga gaagaagtac agcccctgcg   12360
cttgggaagt cgtgagggct gagatcatga ggagctttag cctgagcacc aacctgcaag   12420
agagcttgag gtctaaggag taaaaagtct agagtcgggg cggcgcgtgg taggtggcgg   12480
ggggttccca ggagagcccc cagcgcggac ggcagcgccg tcactcaccg ctccgtctcc   12540
ctccgcccag ggtcgcctgg cgcaaccgct gcaagggcac cgacgtccag gcgtggatca   12600
gaggctgccg gctgtgagga gctgccgcgc ccggcccgcc cgctgcacag ccggccgctt   12660
tgcgagcgcg acgctacccg cttggcagtt ttaaacgcat ccctcattaa aacgactata   12720
cgcaaacgcc ttcccgtcgg tccgcgtctc tttccgccgc cagggcgaca ctcgcgggga   12780
gggcgggaag ggggccgggc gggagcccgc ggccaaccgt cgcccgtga cggcaccgcc    12840
ccgcccccgt gacgcggtgc gggcgccggg gccgtggggc tgagcgctgc ggcggggccg   12900
ggccgggccg gggcgggagc tgagcgcggc gggctgcgg gcggcgcccc ctccggtgca    12960
atatgttcaa gagaatggct gagttcgggc ctgactccgg gggcagggtg aaggtgcggc   13020
gcgggcggag ggacggggcg ggcgcggggc gccccggcgg gtgccggggc ctctgccggc   13080
ccgcccggct cgggctgctg cggcgcttac gggcgcgctt ctcgccgctg ccgcttctct   13140
```

```
tctctcccgc gcaagggcgt caccatcgtg aagccggtag tgtacgggaa cgtggcgcgg    13200
tacttcggga agaagaggga ggaggacggg cacacgcatc agtggacggt ttacgtgaag    13260
ccctacagga acgaggtagg gcccgagcgc gtcggccgcc gttctcggag cgccggagcc    13320
gtcagcgccg cgcctgggtg cgctgtggga cacagcgagc ttctctcgta ggacatgtcc    13380
gcctacgtga aaaaaatcca gttcaagctg cacgagagct acgggaatcc tctccgaggt    13440
gggtgttgcg tcgggggggtt tgctccgctc ggtcccgctg aggctcgtcg ccctcatctt    13500
tctttcgtgc cgcagtcgtt accaaaccgc cgtacgagat caccgaaacg ggctggggcg    13560
aatttgaaat catcatcaag atattttttca ttgatccaaa cgagcgaccc gtaagtacgc    13620
tcagcttctc gtagtgcttc ccccgtcctg gcggcccggg gctgggctgc tcgctgctgc    13680
cggtcacagt cccgccagcc gcggagctga ctgagctccc tttcccggga cgtgtgctct    13740
gtgttcggtc agcgaggcta tcgggagggc tttggctgca tttggcttct ctggcgctta    13800
gcgcaggagc acgttgtgct acgcctgaac tacagctgtg agaaggccgt ggaaaccgct    13860
ctcaaactga tttattggcg aaatggctct aaactaaatc gtctcctctc tttggaaatg    13920
ctttagagaa ggtctctgtg gtagttctta tgcatctatc ctaaagcact ggccagaca    13980 atttaaagac atcaagcagc atttatagca ggcacgttta ataacgaata ctgaatttaa    14040
gtaactctgc tcacgttgta tgacgtttat tttcgtattc ctgaaagcca ttaaaatcct    14100
gtgcagttgt ttagtaagaa cagctgccac tgttttgtat ctaggagata actggtgttt    14160
ccctacagtt ctcaagctga taaaactctg tctttgtatc taggtaaccc tgtatcactt    14220
gctgaagctt tttcagtctg acaccaatgc aatcctggga agaaaactg tagtttctga    14280 attctatgat gaaatggtat gaaaatttta atgtcaaccg agcctgactt tatttaaaaa    14340
aaattattga tggtgctgtg tattttggtc cttccttaga tatttcaaga tcctactgcc    14400
atgatgcagc aactgctaac gacgtcccgt cagctgacac ttggtgctta caagcatgaa    14460
acagagtgta agtgcaaaat gaggatacct tcgccgaccg tcattcacta ctaatgtttt    14520
ctgtgggatg tgatcgtaca gtgagtttgg ctgtgtgaaa tttgaatagc ttggtattgg    14580
cagtgatgac gtgatcgatg ccttgcttat catgtttgaa atgaagtaga ataaatgcag    14640
cctgctttat ttgagatagt ttggttcatt ttatggaatg caagcaaaga ttatacttcc    14700
tcactgaatt gcactgtcca aggtgtgaa atgtgtgggg atctggagga ccgtgaccga    14760
gggacattgg atcgctatct cccatttctt ttgctgttac cagttcagat tttcttttca    14820
cctagtcttt aattcccagg gttttgtttt ttccttggtc atagtttttg tttttcactc    14880
tggcaaatga tgttgtgaat tacactgctt cagccacaaa actgatggac tgaatgaggt    14940
catcaaacaa acttttcttc ttccgtattt ccttttttt cccccactta tcatttttac    15000
tgctgttgtt gagtctgtaa ggctaaaagt aactgttttg tgcttttttca ggacgtgtgc    15060 tttccaaatt actgccacat atataaagaa aggttggaat tttaaagata attcatgttt    15120
cttcttcttt tttgccacca cagttgcaga tcttgaagta aaaccaggg aaaagctgga    15180 agctgccaaa aagaaaacca gttttgaaat tgctgagctt aaagaaaggt taaaagcaag    15240
tcgtgaaacc atcaactgct taaagagtga atcagaaaaa ctcgaagagg atgatcagtc    15300
taaagatatg tgatgagtgt tgacttggca gggagcctat aatgagaatg aaaggacttc    15360
agtcgtggag ttgtatgcgt tctctccaat tctgtaacgg agactgtatg aatttcattt    15420
gcaaatcact gcagtgtgtg acaactgact ttttataaat ggcagaaaac aagaatgaat    15480
gtatcctcat tttatagtta aaatctatgg gtatgtactg gtttatttca aggagaatgg    15540
```

```
atcgtagaga cttggaggcc agattgctgc ttgtattgac tgcatttgag tggtgtagga    15600
acattttgtc tatggtcccg tgttagttta cagaatgcca ctgttcactg ttttgttttg    15660
tattttactt tttctactgc aacgtcaagg ttttaaaagt tgaaataaaa acatgcaggt    15720 ttttttaaa tattttttg tctctatcca gtttgggctt caagtattat tgttaacagc    15780
aagtcctgat ttaagtcaga ggctgaagtg taatggtatt caagatgctt aagtctgttg    15840
tcagcaaaac aaaagagaaa acttcataaa atcaggaagt tggcatttct ataacttct    15900 ttatcaacag ataagagttt ctagccctgc atctactttc acttatgtag ttgatgcctt    15960
tatattttgt gtgtttggat gcaggaagtg attcctactc tgttatgtag atattctatt    16020
taacacttgt actctgctgt gcttagcctt tccccatgaa aattcagcgg ctgtaaatcc    16080
ccctcttctt ttgtagcctc atacagatgg cagaccctca ggcttataaa ggcttgggca    16140
tcttctttac tgctttgaga ttctgtgttg cagtaacctc tgccagagag gagaaaagcc    16200
ccacaaacct catccccttc ttctatagca atcagtatta ctaatgcttt gagaacagag    16260
cactggtttg aaacgtttga taattagcat ttaacatggc ttggtaaaga tgcagaactg    16320
aaacagctgt gacagtatga actcagtatg gagacttcat taagacaaac agctgttaaa    16380
atcaggcatg tttcattgag gaggacgggg caacttgcac cagtggtgcc cacacaaatc    16440
cttcctggcg ctgcagacca attttttctgg cattctgact gccgttgctg ctggtcacag    16500
agagcaacta tttttatcag ccacaggcaa tttgcttgta gtattttcca agtgttgtag    16560
gtaagtataa atgcatcggc tccagagcac tttgagtata cttattaaaa acataaatga    16620
aagacaaatt agctttgctt gggtgcacag aacattttta gttccagcct gcttttggt    16680 agaagccctc ttctgaggct agaactgact ttgacaagta gagaaactgg caacggagct    16740
attgctatcg aaggatcctt gttaacaaag ttaatcgtct tttaaggttt ggtttattca    16800
ttaaatttgc ttttaagctg tagctgaaaa agaacgtgct gtcttccatg caccaggtgg    16860
cagctctgtg caaagtgctc tctggtctca ccagcctttt aattgccggg attctggcac    16920
gtctgagagg gctcagactg gcttcgtttg tttgaacagc gtgtactgct ttctgtagac    16980
atggccggtt tctctcctgc agcttatgaa actgttcaca ctgaacacac tggaacaggt    17040
tgcccaagga ggccgtggat gccccatccc tggaggcatt caaggccagg ctggatgtgg    17100
ctctgggcag cctggtctgg tggttggcga tcctgcacat agcagcgggg ttgaaactcg    17160
atgatcactg tggtccttt caacccaggc tattctatga ttctatgatt caacagcaaa    17220
tcatatgtac tgagagagga aacaaacaca agtgctactg tttgcaagtt ttgttcattt    17280
ggtaaaagag tcaggtttta aaattcaaaa tctgtctggt tttggtgttt ttttttttt    17340 atttattatt tctttggggt tcttttgat gctttatctt tctctgccag gactgtgtga    17400
caatgggaac gaaaagaac atgccaggca ctgtcctgga ttgcacacgc tggttgcact    17460
cagtagcagg ctcagaactg ccagtctttc cacagtatta ctttctaaac ctaattttaa    17520
tagcgttagt agacttccat cactgggcag tgcttagtga atgctctgtg tgaacgtttt    17580
acttataagc atgttggaag ttttgatgtt cctggatgca gtagggaagg acagattagc    17640
tatgtgaaaa gtagattctg agtatcgggg ttacaaaaag tatagaaacg atgagaaatt    17700
cttgttgtaa ctaattggaa tttctttaag cgttcactta tgctacattc atagtatttc    17760
catttaaaag taggaaaagg taaaacgtga aatcgtgtga ttttcggatg gaacaccgcc    17820
ttcctatgca cctgaccaac ttccagagga aaagcctatt gaaagccgag attaagccac    17880
```

```
caaaagaact catttgcatt ggaatatgta gtatttgccc tcttcctccc gggtaattac    17940
tatactttat agggtgctta tatgttaaat gagtggctgg cactttttat tctcacagct    18000
gtggggaatt ctgtcctcta ggacagaaac aattttaatc tgttccactg gtgactgctt    18060
tgtcagcact tccacctgaa gagatcaata cactcttcaa tgtctagttc tgcaacactt    18120
ggcaaacctc acatcttatt tcatactctc ttcatgccta tgcttattaa agcaataatc    18180
tgggtaattt ttgttttaat cactgtcctg accccagtga tgaccgtgtc ccacctaaag    18240
ctcaattcag gtcctgaatc tcttcaactc tctatagcta acatgaagaa tcttcaaaag    18300
ttaggtctga gggacttaag gctaactgta gatgttgttg cctggtttct gtgctgaagg    18360
ccgtgtagta gttagagcat tcaacctcta g                                  18391

<210> SEQ ID NO 71
<211> LENGTH: 11
<212> TYPE: PRT
<213> ORGANISM: SV40
<220> FEATURE:
<223> OTHER INFORMATION: nuclear localization signal peptide

<400> SEQUENCE: 71

Cys Gly Gly Pro Lys Lys Lys Arg Lys Val Gly
1               5                   10

<210> SEQ ID NO 72
<211> LENGTH: 20
<212> TYPE: DNA
<213> ORGANISM: Artificial Sequence
<220> FEATURE:
<223> OTHER INFORMATION: Primer lys051

<400> SEQUENCE: 72
tgcatccttc agcacttgag                                                   20

<210> SEQ ID NO 73
<211> LENGTH: 20
<212> TYPE: DNA
<213> ORGANISM: Artificial Sequence
<220> FEATURE:
<223> OTHER INFORMATION: Primer ifn3

<400> SEQUENCE: 73
aactcctctt gaggaaagcc                                                   20

<210> SEQ ID NO 74
<211> LENGTH: 21329
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
```

(MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription enhancer
<220> FEATURE:
<221> NAME/KEY: misc_feature
<222> LOCATION: (9160)..(9325)
<223> OTHER INFORMATION: Transcription enhancer
<220> FEATURE:
<221> NAME/KEY: misc_feature
<222> LOCATION: (9326)..(9626)
<223> OTHER INFORMATION: Negative regulatory element
<220> FEATURE:
<221> NAME/KEY: misc_feature
<222> LOCATION: (9621)..(9660)
<223> OTHER INFORMATION: Hormone response element
<220> FEATURE:
<221> NAME/KEY: misc_feature
<222> LOCATION: (9680)..(10060)
<223> OTHER INFORMATION: Hormone response element
<220> FEATURE:
<221> NAME/KEY: misc_feature
<222> LOCATION: (10576)..(10821)
<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
       Peptide
<220> FEATURE:
<221> NAME/KEY: misc_feature
<222> LOCATION: (11846)..(12443)
<223> OTHER INFORMATION: Human Interferon alpha 2b encoding region
       codon optimized for exp ression in chicken cells (IFNMAGMAX)
<220> FEATURE:
<221> NAME/KEY: misc_feature
<222> LOCATION: (12464)..(18391)
<223> OTHER INFORMATION: Chicken Lysozyme 3prime domain
<220> FEATURE:
<221> NAME/KEY: misc_feature
<222> LOCATION: (18392)..(21329)
<223> OTHER INFORMATION: pPolyIII-I and pBluescript cloning vector
       sequence

<400> SEQUENCE: 74

```
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttctttttc ttagtaaatt ttctactgga     300
ctgtatgttt tgacaggtca gaaacatttc ttcaaaagaa gaaccttttg gaaactgtac     360 agccctttc tttcattccc tttttgcttt ctgtgccaat gccttggtt ctgattgcat     420 tatggaaaac gttgatcgga acttgaggtt tttatttata gtgtggcttg aaagcttgga     480
tagctgttgt tacacgagat accttattaa gttaggcca gcttgatgct ttattttttc     540
cctttgaagt agtgagcgtt ctctggtttt tttcctttga aactggtgag cttagatttt     600
ttctaatggg atttttttacc tgatgatcta gttgcatacc caaatgcttg taaatgtttt     660
cctagttaac atgttgataa cttcggattt acatgttgta tatacttgtc atctgtgttt     720
```

```
ctagtaaaaa tatatggcat ttatagaaat acgtaattcc tgatttcctt ttttttttatc      780
tctatgctct gtgtgtacag gtcaaacaga cttcactcct atttttattt atagaatttt      840
atatgcagtc tgtcgttggt tcttgtgttg taaggataca gccttaaatt tcctagagcg      900
atgctcagta aggcgggttg tcacatgggt tcaaatgtaa aacgggcacg tttggctgct      960
gccttcccga gatccaggac actaaactgc ttctgcactg aggtataaat cgcttcagat     1020
cccagggaag tgcagatcca cgtgcatatt cttaaagaag aatgaatact ttctaaaata     1080
ttttggcata ggaagcaagc tgcatggatt tgtttgggac ttaaattatt ttggtaacgg     1140
agtgcatagg ttttaaacac agttgcagca tgctaacgag tcacagcgtt tatgcagaag     1200
tgatgcctgg atgcctgttg cagctgttta cggcactgcc ttgcagtgag cattgcagat     1260
aggggtgggg tgctttgtgt cgtgttccca cacgctgcca cacagccacc tcccggaaca     1320
catctcacct gctgggtact tttcaaacca tcttagcagt agtagatgag ttactatgaa     1380
acagagaagt tcctcagttg gatattctca tgggatgtct ttttttcccat gttgggcaaa     1440
gtatgataaa gcatctctat ttgtaaatta tgcacttgtt agttcctgaa tcctttctat     1500
agcaccactt attgcagcag gtgtaggctc tggtgtggcc tgtgtctgtg cttcaatctt     1560
ttaaagcttc tttggaaata cactgacttg attgaagtct cttgaagata gtaaacagta     1620
cttacctttg atcccaatga aatcgagcat ttcagttgta aaagaattcc gcctattcat     1680
accatgtaat gtaattttac accccagtg ctgacacttt ggaatatatt caagtaatag     1740
actttggcct caccctcttg tgtactgtat tttgtaatag aaaatatttt aaactgtgca     1800
tatgattatt acattatgaa agagacattc tgctgatctt caaatgtaag aaaatgagga     1860
gtgcgtgtgc ttttataaat acaagtgatt gcaaattagt gcaggtgtcc ttaaaaaaaa     1920
aaaaaaaaag taatataaaa aggaccaggt gttttacaag tgaaatacat tcctatttgg     1980
taaacagtta cattttatg aagattacca gcgctgctga ctttctaaac ataaggctgt     2040
attgtcttcc tgtaccattg catttcctca ttcccaattt gcacaaggat gtctgggtaa     2100
actattcaag aaatggcttt gaaatacagc atgggagctt gtctgagttg gaatgcagag     2160
ttgcactgca aaatgtcagg aaatggatgt ctctcagaat gcccaactcc aaaggatttt     2220
atatgtgtat atagtaagca gtttcctgat tccagcaggc caaagagtct gctgaatgtt     2280
gtgttgccgg agacctgtat ttctcaacaa ggtaagatgg tatcctagca actgcggatt     2340
ttaatacatt ttcagcagaa gtacttagtt aatctctacc tttagggatc gtttcatcat     2400
ttttagatgt tatacttgaa atactgcata acttttagct ttcatgggtt cctttttttc     2460
agcctttagg agactgttaa gcaatttgct gtccaacttt tgtgttggtc ttaaactgca     2520
atagtagttt accttgtatt gaagaaataa agaccatttt tatattaaaa aatacttttg     2580
tctgtcttca ttttgacttg tctgatatcc ttgcagtgcc cattatgtca gttctgtcag     2640
atattcagac atcaaaactt aacgtgagct cagtggagtt acagctgcgg ttttgatgct     2700
gttattattt ctgaaactag aaatgatgtt gtcttcatct gctcatcaaa cacttcatgc     2760
agagtgtaag gctagtgaga aatgcataca tttattgata cttttttaaa gtcaactttt     2820
tatcagattt ttttttcatt tggaaatata ttgttttcta gactgcatag cttctgaatc     2880
tgaaatgcag tctgattggc atgaagaagc acagcactct tcatcttact taaacttcat     2940
tttggaatga aggaagttaa gcaagggcac aggtccatga aatagagaca gtgcgctcag     3000
gagaaagtga acctggattt cttttggctag tgttctaaat ctgtagtgag gaaagtaaca     3060
cccgattcct tgaaagggct ccagctttaa tgcttccaaa ttgaaggtgg caggcaactt     3120
```

```
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tattttaag tactgtgttg caaacgtctc atctgcaaat     3360 acgtaggtg tgtactctcg aagattaaca gtgtgggttc agtaatatat ggatgaattc      3420
acagtggaag cattcaaggg tagatcatct aacgacacca gatcatcaag ctatgattgg    3480
aagcggtatc agaagagcga ggaaggtaag cagtcttcat atgttttccc tccacgtaaa    3540
gcagtctggg aaagtagcac cccttgagca gagacaagga ataattcag gagcatgtgc     3600 taggagaact tcttgctga attctacttg caagagcttt gatgcctggc ttctggtgcc     3660
ttctgcagca cctgcaaggc ccagagcctg tggtgagctg gagggaaaga ttctgctcaa    3720
gtccaagctt cagcaggtca ttgtctttgc ttcttccccc agcactgtgc agcagagtgg    3780
aactgatgtc gaagcctcct gtccactacc tgttgctgca ggcagactgc tctcagaaaa    3840
agagagctaa ctctatgcca tagtctgaag gtaaaatggg tttaaaaaa gaaaacacaa     3900 aggcaaaacc ggctgcccca tgagaagaaa gcagtggtaa acatggtaga aaaggtgcag    3960
aagcccccag gcagtgtgac aggccccctcc tgccacctag aggcgggaac aagcttccct   4020
gcctagggct ctgcccgcga agtgcgtgtt tctttggtgg gttttgtttg gcgtttggtt    4080
ttgagattta gacacaaggg aagcctgaaa ggaggtgttg ggcactattt tggtttgtaa    4140
agcctgtact tcaaatatat attttgtgag ggagtgtagc gaattggcca attttaaaata   4200 aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt ttgagaagat ggcagttgct    4500
tctttccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg gccaaaggtg ggtgggtttc    4740
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccacccccac tgcaggctta    4920
gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac atttttttta aatacataaa    5280
ctacttcaaa tgaggtcgga gaaggtcagt gtttattag cagccataaa accaggtgag     5340
cgagtaccat ttttctctac aagaaaaacg attctgagct ctgcgtaagt ataagttctc    5400
catagcggct gaagctcccc cctggctgcc tgccatctca gctggagtgc agtgccattt    5460
```

```
ccttggggtt tctctcacag cagtaatggg acaatacttc acaaaaattc tttcttttcc    5520
tgtcatgtgg gatccctact gtgccctcct ggttttacgt taccccctga ctgttccatt    5580
cagcggtttg gaaagagaaa aagaatttgg aaataaaaca tgtctacgtt atcacctcct    5640
ccagcatttt ggtttttaat tatgtcaata actggcttag atttggaaat gagaggggt    5700
tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttatttt cgttcttcca tatcagtctt ctctatgaca attcacatcc    6180
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa ccccttctga gactcatctt    6360
aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa ccccttaagg cattcagaac aactagaatc atagaatggt ttggattgga    6600
aggggcctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agacccctcg ctgatttgtg tcaagctttt    7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata aatcctgtat tgggatcag    7500
ttacctttg gggtaagctt ttgtatctgc agagaccctg ggggtctga tgtgcttcag    7560
ctctgctctg ttctgactgc accatttct agatcaccca gttgttcctg tacaacttcc    7620
ttgtcctcca tccttttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
```

```
gcatttattt  acttctatta  tgtacttact  ttgacataac  acagacacgc  acatattttg   7920
ctgggatttc  cacagtgtct  ctgtgtcctt  cacatggttt  tactgtcata  cttccgttat   7980
aaccttggca  atctgcccag  ctgcccatca  aagaaaaga   gattccttt   ttattacttc   8040
tcttcagcca  ataaacaaaa  tgtgagaagc  ccaaacaaga  acttgtgggg  caggctgcca   8100
tcaagggaga  gacagctgaa  gggttgtgta  gctcaataga  attaagaaat  aataaagctg   8160
tgtcagacag  ttttgcctga  tttatacagg  cacgccccaa  gccagagagg  ctgtctgcca   8220
aggccacctt  gcagtccttg  gtttgtaaga  taagtcatag  gtaacttttc  tggtgaattg   8280
cgtggagaat  catgatggca  gttcttgctg  tttactatgg  taagatgcta  aaataggaga   8340
cagcaaagta  acacttgctg  ctgtaggtgc  tctgctatcc  agacagcgat  ggcactcgca   8400
caccaagatg  agggatgctc  ccagctgacg  gatgctgggg  cagtaacagt  gggtcccatg   8460
ctgcctgctc  attagcatca  cctcagccct  caccagccca  tcagaaggat  catcccaagc   8520
tgaggaaagt  tgctcatctt  cttcacatca  tcaaaccttt  ggcctgactg  atgcctcccg   8580
gatgcttaaa  tgtggtcact  gacatcttta  ttttctatg   atttcaagtc  agaacctccg   8640
gatcaggagg  gaacacatag  tgggaatgta  ccctcagctc  caaggccaga  tcttccttca   8700
atgatcatgc  atgctactta  ggaaggtgtg  tgtgtgtgaa  tgtagaattg  cctttgttat   8760
ttttcttcc   tgctgtcagg  aacattttga  ataccagaga  aaaagaaaag  tgctcttctt   8820
ggcatgggag  gagttgtcac  acttgcaaaa  taaaggatgc  agtcccaaat  gttcataatc   8880
tcagggtctg  aaggaggatc  agaaactgtg  tatacaattt  caggcttctc  tgaatgcagc   8940
ttttgaaagc  tgttcctggc  cgaggcagta  ctagtcagaa  ccctcggaaa  caggaacaaa   9000
tgtcttcaag  gtgcagcagg  aggaaacacc  ttgcccatca  tgaaagtgaa  taaccactgc   9060
cgctgaagga  atccagctcc  tgtttgagca  ggtgctgcac  actcccacac  tgaaacaaca   9120
gttcatttt   ataggacttc  caggaaggat  cttcttctta  agcttcttaa  ttatggtaca   9180
tctccagttg  gcagatgact  atgactactg  acaggagaat  gaggaactag  ctgggaatat   9240
ttctgtttga  ccaccatgga  gtcacccatt  tctttactgg  tatttggaaa  taataattct   9300
gaattgcaaa  gcaggagtta  gcgaagatct  tcatttcttc  catgttggtg  acagcacagt   9360
tctggctatg  aaagtctgct  tacaaggaag  aggataaaaa  tcatagggat  aataaatcta   9420
agtttgaaga  caatgaggtt  ttagctgcat  ttgacatgaa  gaaattgaga  cctctactgg   9480
atagctatgg  tatttacgtg  tcttttttgct tagttactta  ttgaccccag  ctgaggtcaa   9540
gtatgaactc  aggtctctcg  ggctactggc  atggattgat  tacatacaac  tgtaattta   9600
gcagtgattt  agggtttatg  agtactttg   cagtaaatca  tagggttagt  aatgttaatc   9660
tcagggaaaa  aaaaaaaaag  ccaaccctga  cagacatccc  agctcaggtg  gaaatcaagg   9720
atcacagctc  agtgcggtcc  cagagaacac  agggactctt  ctcttaggac  ctttatgtac   9780
agggcctcaa  gataactgat  gttagtcaga  agactttcca  ttctggccac  agttcagctg   9840
aggcaatcct  ggaattttct  ctccgctgca  cagttccagt  catcccagtt  tgtacagttc   9900
tggcactttt  tgggtcaggc  cgtgatccaa  ggagcagaag  ttccagctat  ggtcagggag   9960
tgcctgaccg  tcccaactca  ctgcactcaa  acaaaggcga  aaccacaaga  gtggcttttg  10020
ttgaaattgc  agtgtggccc  agaggggctg  caccagtact  ggattgacca  cgaggcaaca  10080
ttaatcctca  gcaagtgcaa  tttgcagcca  ttaaattgaa  ctaactgata  ctacaatgca  10140
atcagtatca  acaagtggtt  tggcttggaa  gatggagtct  aggggctcta  caggagtagc  10200
```

```
tactctctaa tggagttgca ttttgaagca ggacactgtg aaaagctggc ctcctaaaga   10260
ggctgctaaa cattagggtc aattttccag tgcactttct gaagtgtctg cagttcccca   10320
tgcaaagctg cccaaacata gcacttccaa ttgaatacaa ttatatgcag gcgtactgct   10380
tcttgccagc actgtccttc tcaaatgaac tcaacaaaca atttcaaagt ctagtagaaa   10440
gtaacaagct ttgaatgtca ttaaaaagta tatctgcttt cagtagttca gcttatttat   10500
gcccactaga aacatcttgt acaagctgaa cactggggct ccagattagt ggtaaaacct   10560
actttataca atcatagaat catagaatgg cctgggttgg aagggacccc aaggatcatg   10620
aagatccaac accccgcca caggcagggc caccaacctc cagatctggt actagaccag   10680
gcagcccagg gctccatcca acctggccat gaacacctcc agggatggag catccacaac   10740
ctctctgggc agcctgtgcc agcacctcac cacccctctct gtgaagaact tttccctgac   10800
atccaatcta agccttccct ccttgaggtt agatccactc cccccttgtgc tatcactgtc   10860
tactcttgta aaaagttgat tctcctcctt tttggaaggt tgcaatgagg tctccttgca   10920
gccttcttct cttctgcagg atgaacaagc ccagctccct cagcctgtct ttataggaga   10980
ggtgctccag ccctctgatc atctttgtgg ccctcctctg gacccgctcc aagagctcca   11040
catctttcct gtactggggg ccccaggcct gaatgcagta ctccagatgg ggcctcaaaa   11100
gagcagagta aagagggaca atccaccttcc tcaccctgct ggccagccct cttctgatgg   11160
agccctggat acaactggct ttctgagctg caacttctcc ttatcagttc cactattaaa   11220
acaggaacaa tacaacaggt gctgatggcc agtgcagagt ttttcacact tcttcatttc   11280
ggtagatctt agatgaggaa cgttgaagtt gtgcttctgc gtgtgcttct tcctcctcaa   11340
atactcctgc ctgatacctc accccacctg ccactgaatg gctccatggc ccctgcagc   11400
cagggccctg atgaacccgg cactgcttca gatgctgttt aatagcacag tatgaccaag   11460
ttgcacctat gaatacacaa acaatgtgtt gcatccttca gcacttgaga agaagagcca   11520
aatttgcatt gtcaggaaat ggtttagtaa ttctgccaat taaaacttgt ttatctacca   11580
tggctgtttt tatggctgtt agtagtggta cactgatgat gaacaatggc tatgcagtaa   11640
aatcaagact gtagatattg caacagacta taaaattcct ctgtggctta gccaatgtgg   11700
tacttcccac attgtataag aaatttggca agtttagagc aatgtttgaa gtgttgggaa   11760
atttctgtat actcaagagg gcgttttga caactgtaga acagaggaat caaaaggggg   11820
tgggaggaag ttaaaagaag aggcaggtgc aagagagctt gcagtcccgc tgtgtgtacg   11880
acactggcaa catgaggtct ttgctaatct tggtgctttg cttcctgccc ctggctgcct   11940
tagggtgcga tctgcctcag acccacagcc tgggcagcag gaggacccctg atgctgctgg   12000
ctcagatgag gagaatcagc ctgttagct gcctgaagga taggcacgat tttggctttc   12060
ctcaagagga gtttggcaac cagtttcaga aggctgagac catccctgtg ctgcacgaga   12120
tgatccagca gatctttaac ctgttagca ccaaggatag cagcgctgct gggatgaga   12180
ccctgctgga taagttttac accgagctgt accagcagct gaacgatctg gaggcttgcg   12240
tgatccaggg cgtgggcgtg accgagaccc ctctgatgaa ggaggatagc atcctggctg   12300
tgaggaagta ctttcagagg atcaccctgt acctgaagga agaagtac agcccctgcg   12360
cttgggaagt cgtgagggct gagatcatga ggagctttag cctgagcacc aacctgcaag   12420
agagcttgag gtctaaggag taaaaagtct agagtcgggg cggcgcgtgg taggtggcgg   12480
ggggttccca ggagagcccc cagcgcggac ggcagcgccg tcactcaccg ctccgtctcc   12540
ctccgcccag ggtcgcctgg cgcaaccgct gcaagggcac cgacgtccag gcgtggatca   12600
```

-continued

```
gaggctgccg gctgtgagga gctgccgcgc ccggcccgcc cgctgcacag ccggccgctt    12660
tgcgagcgcg acgctacccg cttggcagtt ttaaacgcat ccctcattaa aacgactata    12720
cgcaaacgcc ttcccgtcgg tccgcgtctc tttccgccgc cagggcgaca ctcgcgggga    12780
gggcgggaag ggggccgggc gggagcccgc ggccaaccgt cgccccgtga cggcaccgcc    12840
ccgcccccgt gacgcggtgc gggcgccggg gccgtgggc tgagcgctgc ggcggggccg     12900
ggccgggccg gggcgggagc tgagcgcggc gcggctgcgg gcggcgcccc ctccggtgca    12960
atatgttcaa gagaatggct gagttcgggc ctgactccgg gggcagggtg aaggtgcggc    13020
gcgggcggag ggacggggcg ggcgcggggc cgcccggcgg gtgccggggc ctctgccggc    13080
ccgcccggct cgggctgctg cggcgcttac gggcgcgctt ctcgccgctg ccgcttctct    13140
tctctcccgc gcaagggcgt caccatcgtg aagccggtag tgtacgggaa cgtggcgcgg    13200
tacttcggga agaagaggga ggaggacggg cacacgcatc agtggacggt ttacgtgaag    13260
ccctacagga acgaggtagg gcccgagcgc gtcggccgcc gttctcggag cgccggagcc    13320
gtcagcgccg cgcctgggtg cgctgtggga cacagcgagc ttctctcgta ggacatgtcc    13380
gcctacgtga aaaaaatcca gttcaagctg cacgagagct acgggaatcc tctccgaggt    13440
gggtgttgcg tcggggggtt tgctccgctc ggtcccgctg aggctcgtcg ccctcatctt    13500
tctttcgtgc cgcagtcgtt accaaaccgc cgtacgagat caccgaaacg ggctggggcg    13560
aatttgaaat catcatcaag atattttca ttgatccaaa cgagcgaccc gtaagtacgc      13620
tcagcttctc gtagtgcttc ccccgtcctg gcggcccggg gctgggctgc tcgctgctgc    13680
cggtcacagt cccgccagcc gcggagctga ctgagctccc tttccgggga cgtgtgctct    13740
gtgttcggtc agcgaggcta tcgggagggc tttggctgca tttggcttct ctggcgctta    13800
gcgcaggagc acgttgtgct acgcctgaac tacagctgtg agaaggccgt ggaaaccgct    13860
ctcaaactga tttattggcg aaatggctct aaactaaatc gtctcctctc tttgaaaatg    13920
ctttagagaa ggtctctgtg gtagttctta tgcatctatc ctaaagcact tggccagaca    13980
atttaaagac atcaagcagc atttatagca ggcacgttta ataacgaata ctgaatttaa    14040
gtaactctgc tcacgttgta tgacgtttat tttcgtattc ctgaaagcca ttaaaatcct    14100
gtgcagttgt ttagtaagaa cagctgccac tgttttgtat ctaggagata actggtgttt    14160
ccctacagtt ctcaagctga taaaactctg tctttgtatc taggtaaccc tgtatcactt    14220
gctgaagctt tttcagtctg acaccaatgc aatcctggga agaaaactg tagtttctga     14280
attctatgat gaaatggtat gaaaattta atgtcaaccg agcctgactt tatttaaaaa     14340
aaattattga tggtgctgtg tatttggtc cttccttaga tatttcaaga tcctactgcc     14400
atgatgcagc aactgctaac gacgtcccgt cagctgacac ttggtgctta caagcatgaa    14460
acagagtgta agtgcaaaat gaggatacct tcgccgaccg tcattcacta ctaatgtttt    14520
ctgtgggatg tgatcgtaca gtgagtttgg ctgtgtgaaa tttgaatagc ttggtattgg    14580
cagtgatgac gtgatcgatg ccttgcttat catgtttgaa atgaagtaga ataaatgcag    14640
cctgctttat ttgagatagt ttggttcatt ttatggaatg caagcaaaga ttatacttcc    14700
tcactgaatt gcactgtcca aaggtgtgaa atgtgtgggg atctggagga ccgtgaccga    14760
gggacattgg atcgctatct cccatttctt ttgctgttac cagttcagat tttctttca     14820
cctagtcttt aattcccagg gttttgtttt ttccttggtc atagtttttg ttttcactc     14880
tggcaaatga tgttgtgaat tacactgctt cagccacaaa actgatggac tgaatgaggt    14940
```

```
catcaaacaa acttttcttc ttccgtattt ccttttttt cccccactta tcattttac      15000
tgctgttgtt gagtctgtaa ggctaaaagt aactgttttg tgcttttca ggacgtgtgc     15060
tttccaaatt actgccacat atataaagaa aggttggaat tttaaagata attcatgttt    15120
cttcttcttt tttgccacca cagttgcaga tcttgaagta aaaccaggg aaaagctgga     15180
agctgccaaa aagaaaacca gttttgaaat tgctgagctt aaagaaaggt taaaagcaag    15240
tcgtgaaacc atcaactgct taaagagtga atcagaaaa ctcgaagagg atgatcagtc     15300
taaagatatg tgatgagtgt tgacttggca gggagcctat aatgagaatg aaaggacttc    15360
agtcgtggag ttgtatgcgt tctctccaat tctgtaacgg agactgtatg aatttcattt    15420
gcaaatcact gcagtgtgtg acaactgact ttttataaat ggcagaaaac aagaatgaat    15480
gtatcctcat tttatagtta aaatctatgg gtatgtactg gtttatttca aggagaatgg    15540
atcgtagaga cttggaggcc agattgctgc ttgtattgac tgcatttgag tggtgtagga    15600
acattttgtc tatggtcccg tgttagttta cagaatgcca ctgttcactg ttttgttttg    15660
tattttactt tttctactgc aacgtcaagg ttttaaaagt tgaaaataaa acatgcaggt    15720
ttttttaaa tattttttg tctctatcca gtttgggctt caagtattat tgttaacagc      15780
aagtcctgat ttaagtcaga ggctgaagtg taatggtatt caagatgctt aagtctgttg    15840
tcagcaaaac aaaagagaaa acttcataaa atcaggaagt tggcatttct aataacttct    15900
ttatcaacag ataagagttt ctagccctgc atctactttc acttatgtag ttgatgcctt    15960
tatattttgt gtgtttggat gcaggaagtg attcctactc tgttatgtag atattctatt    16020
taacacttgt actctgctgt gcttagcctt tccccatgaa aattcagcgg ctgtaaatcc    16080
ccctcttctt ttgtagcctc atacagatgg cagaccctca ggcttataaa ggcttgggca    16140
tcttctttac tgctttgaga ttctgtgttg cagtaacctc tgccagagag gagaaaagcc    16200
ccacaaacct catccccttc ttctatagca atcagtatta ctaatgcttt gagaacagag    16260
cactggtttg aaacgtttga taattagcat ttaacatggc ttggtaaaga tgcagaactg    16320
aaacagctgt gacagtatga actcagtatg gagacttcat taagacaaac agctgttaaa    16380
atcaggcatg tttcattgag gaggacgggg caacttgcac cagtggtgcc cacacaaatc    16440
cttcctggcg ctgcagacca attttctgg cattctgact gccgttgctg ctggtcacag     16500
agagcaacta tttttatcag ccacaggcaa tttgcttgta gtattttcca agtgttgtag    16560
gtaagtataa atgcatcggc tccagagcac tttgagtata cttattaaaa acataaatga    16620
aagacaaatt agctttgctt gggtgcacag aacatttta gttccagcct gcttttggt      16680
agaagccctc ttctgaggct agaactgact ttgacaagta gagaaactgg caacggagct    16740
attgctatcg aaggatcctt gttaacaaag ttaatcgtct tttaaggttt ggtttattca    16800
ttaaatttgc ttttaagctg tagctgaaaa agaacgtgct gtcttccatg caccaggtgg    16860
cagctctgtg caaagtgctc tctggtctca ccagcctttt aattgccggg attctggcac    16920
gtctgagagg gctcagactg gcttcgtttg tttgaacagc gtgtactgct ttctgtagac    16980
atggccggtt tctctcctgc agcttatgaa actgttcaca ctgaacacac tggaacaggt    17040
tgcccaagga ggccgtggat gccccatccc tggaggcatt caaggccagg ctggatgtgg    17100
ctctgggcag cctggtctgg tggttggcga tcctgcacat agcagcgggg ttgaaactcg    17160
atgatcactg tggtcctttt caacccaggc tattctatga ttctatgatt caacagcaaa    17220
tcatatgtac tgagagagga aacaaacaca agtgctactg tttgcaagtt ttgttcattt    17280
ggtaaaagag tcaggtttta aaattcaaaa tctgtctggt tttggtgttt ttttttttt    17340
```

```
atttattatt tctttgggggt tcttttttgat gctttatctt tctctgccag gactgtgtga    17400
caatgggaac gaaaaagaac atgccaggca ctgtcctgga ttgcacacgc tggttgcact    17460
cagtagcagg ctcagaactg ccagtctttc cacagtatta ctttctaaac ctaattttaa    17520
tagcgttagt agacttccat cactgggcag tgcttagtga atgctctgtg tgaacgtttt    17580
acttataagc atgttggaag ttttgatgtt cctggatgca gtagggaagg acagattagc    17640
tatgtgaaaa gtagattctg agtatcgggg ttacaaaaag tatagaaacg atgagaaatt    17700
cttgttgtaa ctaattggaa tttctttaag cgttcactta tgctacattc atagtatttc    17760
catttaaaag taggaaaagg taaaacgtga aatcgtgtga ttttcggatg gaacaccgcc    17820
ttcctatgca cctgaccaac ttccagagga aaagcctatt gaaagccgag attaagccac    17880
caaaagaact catttgcatt ggaatatgta gtatttgccc tcttcctccc gggtaattac    17940
tatactttat agggtgctta tatgttaaat gagtggctgg cacttttat tctcacagct    18000 gtggggaatt ctgtcctcta ggacagaaac aatttttaatc tgttccactg gtgactgctt    18060
tgtcagcact tccacctgaa gagatcaata cactcttcaa tgtctagttc tgcaacactt    18120
ggcaaacctc acatcttatt tcatactctc ttcatgccta tgcttattaa agcaataatc    18180 tgggtaatttt ttgtttttaat cactgtcctg accccagtga tgaccgtgtc ccacctaaag    18240
ctcaattcag gtcctgaatc tcttcaactc tctatagcta acatgaagaa tcttcaaaag    18300
ttaggtctga gggacttaag gctaactgta gatgttgttg cctggtttct gtgctgaagg    18360
ccgtgtagta gttagagcat tcaacctcta gaagaagctt ggccagctgg tcgacctgca    18420
gatccggccc tcgaggggggg gcccggtacc cagcttttgt tccctttagt gagggttaat    18480
ttcgagcttg gcgtaatcat ggtcatagct gtttcctgtg tgaaattgtt atccgctcac    18540
aattccacac aacatacgag ccggaagcat aaagtgtaaa gcctggggtg cctaatgagt    18600
gagctaactc acattaattg cgttgcgctc actgcccgct ttccagtcgg gaaacctgtc    18660
gtgccagctg cattaatgaa tcggccaacg cgcggggaga ggcggtttgc gtattgggcg    18720
ctcttccgct tcctcgctca ctgactcgct gcgctcggtc gttcggctgc ggcgagcggt    18780
atcagctcac tcaaaggcgg taatacggtt atccacagaa tcagggggata acgcaggaaa    18840 gaacatgtga gcaaaaggcc agcaaaaggc caggaaccgt aaaaaggccg cgttgctggc    18900 gttttttccat aggctccgcc cccctgacga gcatcacaaa aatcgacgct caagtcagag    18960
gtggcgaaac ccgacaggac tataaagata ccaggcgttt ccccctggaa gctccctcgt    19020
gcgctctcct gttccgaccc tgccgcttac cggatacctg tccgcctttc tcccttcggg    19080
aagcgtggcg ctttctcata gctcacgctg taggtatctc agttcggtgt aggtcgttcg    19140
ctccaagctg ggctgtgtgc acgaaccccc cgttcagccc gaccgctgcg ccttatccgg    19200
taactatcgt cttgagtcca acccggtaag acacgactta tcgccactgg cagcagccac    19260
tggtaacagg attagcagag cgaggtatgt aggcggtgct acagagttct tgaagtggtg    19320
gcctaactac ggctacacta aaggacagt atttggtatc tgcgctctgc tgaagccagt    19380
taccttcgga aaaagagttg gtagctcttg atccggcaaa caaccaccg ctggtagcgg    19440 tggttttttt gtttgcaagc agcagattac gcgcagaaaa aaaggatctc aagaagatcc    19500
tttgatcttt tctacggggt ctgacgctca gtggaacgaa aactcacgtt aagggatttt    19560
ggtcatgaga ttatcaaaaa ggatcttcac ctagatcctt ttaaattaaa aatgaagttt    19620
taaatcaatc taaagtatat atgagtaaac ttggtctgac agttaccaat gcttaatcag    19680
```

-continued

```
tgaggcacct atctcagcga tctgtctatt tcgttcatcc atagttgcct gactcccgt    19740 cgtgtagata actacgatac gggagggctt accatctggc cccagtgctg caatgatacc   19800
gcgagaccca cgctcaccgg ctccagattt atcagcaata aaccagccag ccggaagggc   19860
cgagcgcaga agtggtcctg caactttatc cgcctccatc cagtctatta attgttgccg   19920
ggaagctaga gtaagtagtt cgccagttaa tagtttgcgc aacgttgttg ccattgctac   19980
aggcatcgtg gtgtcacgct cgtcgtttgg tatggcttca ttcagctccg gttcccaacg   20040
atcaaggcga gttacatgat cccccatgtt gtgcaaaaaa gcggttagct ccttcggtcc   20100
tccgatcgtt gtcagaagta agttggccgc agtgttatca ctcatggtta tggcagcact   20160
gcataattct cttactgtca tgccatccgt aagatgcttt tctgtgactg gtgagtactc   20220
aaccaagtca ttctgagaat agtgtatgcg gcgaccgagt tgctcttgcc cggcgtcaat   20280
acgggataat accgcgccac atagcagaac tttaaaagtg ctcatcattg gaaaacgttc   20340
ttcggggcga aaactctcaa ggatcttacc gctgttgaga tccagttcga tgtaacccac   20400
tcgtgcaccc aactgatctt cagcatcttt tactttcacc agcgtttctg ggtgagcaaa   20460
aacaggaagg caaaatgccg caaaaaaggg aataagggcg acacggaaat gttgaatact   20520
catactcttc cttttcaat attattgaag catttatcag ggttattgtc tcatgagcgg    20580
atacatattt gaatgtattt agaaaaataa acaaataggg gttccgcgca catttccccg   20640
aaaagtgcca cctaaattgt aagcgttaat attttgttaa aattcgcgtt aaattttgt    20700 taaatcagct cattttttaa ccaataggcc gaaatcggca aaatccctta taatcaaaa    20760 gaatagaccg agatagggtt gagtgttgtt ccagtttgga acaagagtcc actattaaag   20820
aacgtggact ccaacgtcaa agggcgaaaa accgtctatc agggcgatgg cccactacgt   20880
gaaccatcac cctaatcaag ttttttgggg tcgaggtgcc gtaaagcact aaatcggaac   20940
cctaaaggga gcccccgatt tagagcttga cggggaaagc cggcgaacgt ggcgagaaag   21000
gaagggaaga agcgaaagg agcgggcgct agggcgctgg caagtgtagc ggtcacgctg     21060
cgcgtaacca ccacacccgc cgcgcttaat gcgccgctac agggcgcgtc ccattcgcca   21120
ttcaggctgc gcaactgttg ggaagggcga tcggtgcggg cctcttcgct attacgccag   21180
ctggcgaaag ggggatgtgc tgcaaggcga ttaagttggg taacgccagg gttttcccag   21240
tcacgacgtt gtaaaacgac ggccagtgaa ttgtaatacg actcactata gggcgaattg   21300
gagctccacc gcggtggcgg ccgctctag                                     21329
```

<210> SEQ ID NO 75
<211> LENGTH: 9597
<212> TYPE: DNA
<213> ORGANISM: Artificial Sequence
<220> FEATURE:
<223> OTHER INFORMATION: pALV-SIN-4.0-Lys-IFNa-2B

<400> SEQUENCE: 75

```
gatccccgt gctgcagaac cgagcggcta ttgacttctt gctcctagct cacggccatg      60
gctgtgagga cattgcggga atgtgttgtt tcaatctgag tgatcacagt gagtctatac    120
agaagaagtt ccagctaatg aaggaacatg tcaataagat cggcgtgaac aacgacccaa    180
tcggaagttg gctgcgagga ttattcggag gaataggaga tgggccgta cacttgctga    240 aaggactgct tttggggctt gtagttatct tgttgctagt agtatgcttg ccttgccttt    300
tgcaatgtgt atctagtagt attcgaaaga tgattgataa ttcactcggc tatcgcgagg    360
aatataaaaa aattacagga ggcttataag cagcccgaaa gaagagcgta ggcgagttct    420
```

```
tgtattccgt gtgatagctg gttggattgg taattgatcg gctggcacgc ggaatatagg      480
aggtcgctga atagtaaact tgtagacttg gctacagcat agagtatctt ctgtagctct      540
gatgactgct aggaaataat gctacggata atgtggggag ggcaaggctt gcgaatcggg      600
ttgtaacggg caaggcttga ctgagtggac aatagcatgt ttaggcgaaa agcggggctt      660
cggttgtacg cggttaggag tccctcagg atatagtagt ttcgcttttg catagggagg       720
gggacggatt ggacgaacca ctgaattccg cattgcagag atattgtatt taagtgccta      780
gctcgataca ataaacgcca tttgaccatt caccacattg gtgtgcacct gggttgatgg      840
ccggaccgtt gattccctgr cgactacgag cacatgcatg aagcagaagg cttcatttgg      900
tgaccccgac gtgatcgtta gggaatacgc gctcactggc cgtcgtttta caacgtcgtg      960
actgggaaaa ccctggcgtt acccaactta atcgccttgc agcacatccc cctttcgcca     1020
gctggcgtaa tagcgaagag gcccgcaccg atcgcccttc ccaacagttg cgcagcctga     1080
atggcgaatg gaaattgtaa gcgttaatat tttgttaaaa ttcgcgttaa attttttgtta    1140
aatcagctca ttttttaacc aataggccga atcggcaaa atcccttata atcaaaaga       1200
atagaccgag atagggttga gtgttgttcc agtttggaac aagagtccac tattaaaga      1260
cgtggactcc aacgtcaaag ggcgaaaaac cgtctatcag ggcgatggcc cactacgta     1320
accatcaccc taatcaagtt ttttgggggtc gaggtgccgt aaagcactaa atcggaacc    1380
taaagggagc ccccgattta gagcttgacg gggaaagccg gcgaacgtgg cgagaagga    1440
agggaagaaa gcgaaaggag cgggcgctag ggcgctggca agtgtagcgg tcacgtgcg    1500
cgtaaccacc acacccgccg cgcttaatgc gccgctacag ggcgcgtcag gtggacttt    1560
tcggggaaat gtgcgcggaa cccctatttg tttatttttc taaatacatt caatatgta     1620
tccgctcatg agacaataac cctgataaat gcttcaataa tattgaaaaa ggagagtat     1680
gagtattcaa catttccgtg tcgcccttat tcccttttt gcggcatttt gcttcctgt      1740
ttttgctcac ccagaaacgc tggtgaaagt aaaagatgct gaagatcagt gggtgcacg     1800
agtgggttac atcgaactgg atctcaacag cggtaagatc cttgagagtttttcgcccga    1860
agaacgtttt ccaatgatga gcactttttaa agttctgcta tgtggcgcg tattatcccg    1920
tattgacgcc gggcaagagc aactcggtcg ccgcatacac tattctcaa atgacttggt    1980
tgagtactca ccagtcacag aaaagcatct tacggatggc atgacagaa gagaattatg    2040
cagtgctgcc ataaccatga gtgataacac tgcggccaac ttactttga caacgatcgg    2100
aggaccgaag gagctaaccg ctttttttgca caacatgggg gatcagtaa ctcgccttga    2160
tcgttgggaa ccggagctga atgaagccat accaaacgac gagctgaca ccacgatgcc    2220
tgtagcaatg gcaacaacgt tgcgcaaact attaactggc gaatactta ctctagcttc    2280
ccggcaacaa ttaatagact ggatggaggc ggataaagtt gcggaccac ttctgcgctc    2340
ggcccttccg gctggctggt ttattgctga taaatctgga gcggtgagc gtgggtctcg    2400
cggtatcatt gcagcactgg ggccagatgg taagccctcc gtatcgtag ttatctacac    2460
gacggggagt caggcaacta tggatgaacg aaatagacagatcgctgaga taggtgcctc    2520
actgattaag cattggtaac tgtcagacca agtttactc tatatacttt agattgattt    2580
aaaacttcat ttttaattta aaaggatcta ggtgaagac cttttttgata atctcatgac    2640
caaaatccct taacgtgagt tttcgttcca ctgagcgca gaccccgtag aaaagatcaa    2700
aggatcttct tgagatcctt ttttttctgcg cgtaattgc tgcttgcaaa caaaaaaacc    2760
```

```
accgctacca gcggtggttt gtttgccgga tcaaggcta ccaactcttt ttccgaaggt    2820
aactggcttc agcagagcgc agataccaaa tacttcctt ctagtgtagc cgtagttagg    2880
ccaccacttc aagaactctg tagcaccgcc tactacctc gctctgctaa tcctgttacc    2940
agtggctgct gccagtggcg ataagtcgtg tctaccggg ttggactcaa gacgatagtt    3000
accggataag cgcagcggt cgggctgaac gggggttcg tgcacacagc ccagcttgga    3060
gcgaacgacc tacaccgaac tgagatacct cagcgtgag ctatgagaaa gcgccacgct    3120
tcccgaaggg agaaaggcgg acaggtatccggtaagcggc agggtcggaa caggagagcg    3180
cacgagggag cttccagggg gaaacgcct gtatctttat agtcctgtcg ggtttcgcca    3240
cctctgactt gagcgtcgat ttttgtgag ctcgtcaggg gggcggagcc tatggaaaaa    3300
cgccagcaac gcggcctttt tacgttct ggccttttgc tggccttttg ctcacatgtt    3360
ctttcctgcg ttatccctg attctggga taccgtatt accgcctttg agtgagctga    3420
taccgctcgc cgcagccgaa cgaccagcg cagcgagtca gtgagcgagg aagcggaaga    3480
gcgcccaata cgcaaaccgc ctctcccgc gcgttggccg attcattaat gcagctggca    3540
cgacaggttt cccgactgga aaggggcag tgagcgcaac gcaattaatg tgagttagct    3600
cactcattag gcaccccagg cttacactt tatgcttccg gctcgtatgt tgtgtggaat    3660
tgtgagcgga taacaatttc aacaggaaa cagctatgac catgattacg ccaagcgcgc    3720
attggtaatt gatcggctgg acgcggaat ataggaggtc gctgaatagt aaacttgtag    3780
acttggctac agcatagagtatcttctgta gctctgatga ctgctaggaa ataatgctac    3840
ggataatgtg gggagggca ggcttgcgaa tcggttgta acgggcaagg cttgactgag    3900
gggacaatag catgtttag cgaaaagcgg ggcttcggtt gtacgcggtt aggagtcccc    3960
tcaggatata gtagtttgc ttttgcatag ggagggggaa atgtagtctt atgcaatact    4020
cttgtagtct tgcaactgc ttatgtaacg atgagttagc aacatgcctt ataaggagag    4080
aaaaagcacc gtgcagccg attggtggga gtaaggtggt atgatcgtgg tatgatcgtg    4140
ccttgttagg aaggaacag acgggtctaa cacggattgg acgaaccact gaattccgca    4200
ttgcagagat atttattta agtgcctagc tcgatacaat aaacgccatt tgaccattca    4260
ccacattggt gtcacctgg gttgatggcc ggaccgttga ttccctgrcg actacgagca    4320
catgcatgaa gagaaggct tcatttggtg accccgacgt gatcgttagg gaatagtggt    4380
cggccacagg ggcgtggcg atcctgtcct catccgtctc gcttattcgg ggagcggacg    4440 atgaccctagtagaggggc tgcggcttag gagggcagaa gctgagtggc gtcggaggga    4500 gccctactg aggggggccaa catacccta cgagaactca gagagtcgtt ggaagacggg    4560 aaggaagcc gacgactgag cggtccaccc caggcgtgat tccggttgct ctgcgtgatt    4620 ccggtcgcc ggtggatcaa gcatggaagc cgtcataaag gtgatttcgt ccgcgtgtaa    4680 gacctatgc gggaaaacct ctccttctaa gaaggaaata ggggctatgt tgtccctgtt    4740 acaaaggaa gggttgctta cgtcccccctc agacttatat tccccggggt cctgggatcc    4800 gatacgtcc ctatttttgt gtttgcttca gcagccattt aattcttcag tgtcatcttg    4860 ttcgttgat gccactggaa caggatttt cagcagtcttg caaagaacat ctagctgaaa    4920 acttctgcc attcaatatt cttaccagtt cttcttgttt gaggtgagcc ataaattact    4980 aaacttcgt cactgacaag tttatgcatt ttattacttc tattatgtac ttactttgac    5040 taacacaga cacgcacata ttttgctggg atttccacag tgtctctgtg tccttcacat    5100 gttttactg tcatacttcc gttataacct tggcaatctg cccagctgcc catcacaaga    5160
```

```
aagagattc ctttttattt acttctcttc agccaataaa caaaatgtga gaagcccaaa   5220
aagaacttg tggggcaggc tgccatcaag ggagagacag ctgaagggtt gtgtagctca   5280
tagaattaa gaaataataa agctgtgtca gacagttttg cctgatttat acaggcacgc   5340
ccaagccag agaggctgtc tgccaaggcc accttgcagt ccttggtttg taagataagt   5400
ataggtaac ttttctggtg aattgcgtgg agaatcatga tggcagttct tgctgtttac   5460
atggtaaga tgctaaaata ggagacagca agtaacact tgctgctgta ggtgctctgc    5520
atccagaca gcgatggcac tcgcacacca agatgaggga tgctcccagc tgacggatgc   5580
ggggcagta acagtgggtc ccatgctgcc tgctcattag catcacctca gccctcacca   5640
cccatcaga aggatcatcc caagctgagg aaagttgctc atcttcttca catcatcaaa   5700
cttggcct gactgatgcc tcccggatgc ttaaatgtgg tcactgacat ctttattttt    5760
tatgatttc aagtcagaac ctccggatca ggagggaaca catagtggga atgtaccctc   5820
gctccaagg ccagatcttc cttcaatgat catgcatgct acttaggaag gtgtgtgtgt   5880
tgaatgtag aattgccttt gttattttt cttcctgctg tcaggaacat tttgaatacc    5940
gagaaaaag aaaagtgctc ttcttggcat gggaggagtt gtcacacttg caaaataaag   6000
atgcagtcc caaatgttca taatctcagg gtctgaagga ggatcagaaa ctgtgtatac   6060
atttcaggc ttctctgaat gcagcttttg aaagctgttc ctggccgagg cagtactagt   6120
agaaccctc ggaaacagga acaaatgtct tcaaggtgca gcaggaggaa acaccttgcc   6180
atcatgaaa gtgaataacc actgccgctg aaggaatcca gctcctgttt gagcaggtgc   6240
gcacactcc cacactgaaa caacagttca tttttatagg acttccagga aggatcttct   6300
cttaagctt cttaattatg gtacatctcc agttggcaga tgactatgac tactgacagg   6360
gaatgagga actagctggg aatatttctg tttgaccacc atggagtcac ccatttcttt   6420
ctggtattt ggaaataata attctgaatt gcaaagcagg agttagcgaa gatcttcatt   6480
cttccatgt tggtgacagc acagttctgg ctatgaaagt ctgcttacaa ggaagaggat   6540
aaaatcata gggataataa atctaagttt gaagacatg aggttttagc tgcatttgac    6600
tgaagaaat tgagacctct actggatagc tatggtattt acgtgtcttt ttgcttagtt   6660
cttattgac cccagctgag gtcaagtatg aactcaggtc tctcgggcta ctggcatgga   6720
tgattacat acaactgtaa ttttagcagt gatttagggt ttatgagtac ttttgcagta   6780
atcataggg ttagtaatgt taatctcagg gaaaaaaaaa aaaagccaac cctgacagac   6840
tcccagctc aggtggaaat caaggatcac agctcagtgc ggtcccagag aacacaggga   6900
tcttctctt aggaccttta tgtacagggc tcaagataa ctgatgttag tcagaagact    6960
tccattctg gccacagttc agctgaggca atcctggaat tttctctccg ctgcacagtt   7020
cagtcatcc cagtttgtac agttctggca cttttgggt caggccgtga tccaaggagc    7080
gaagttcca gctatggtca gggagtgcct gaccgtccca actcactgca ctcaaacaaa   7140
gcgaaacca caagagtggc ttttgttgaa attgcagtgt ggcccagagg ggctgcacca   7200
tactggatt gaccacgagg caacattaat cctcagcaag tgcaatttgc agccattaaa   7260
tgaactaac tgatactaca atgcaatcag tatcaacaag tggtttggct tggaagatgg   7320
gtctagggg ctctacagga gtagctactc tctaatggag ttgcattttg aagcaggaca   7380
tgtgaaaag ctggcctcct aaagaggctg ctaaacatta gggtcaattt tccagtgcac   7440
ttctgaagt gtctgcagtt ccccatgcaa agctgcccaa acatagcact tccaattgaa   7500
```

-continued

```
acaattata tgcaggcgta ctgcttcttg ccagcactgt ccttctcaaa tgaactcaac    7560 aacaatttc aaagtctagt agaaagtaac aagctttgaa tgtcattaaa aagtatatct    7620 ctttcagta gttcagctta tttatgccca ctagaaacat cttgtacaag ctgaacactg    7680 ggctccaga ttagtggtaa aacctacttt atacaatcat agaatcatag aatggcctgg    7740 ttggaaggg accccaagga tcatgaagat ccaacacccc cgccacaggc agggccacca    7800 cctccagat ctggtactag accaggcagc ccagggctcc atccaacctg gccatgaaca    7860 ctccaggga tggagcatcc acaacctctc tgggcagcct gtgccagcac ctcacccc    7920 ctctgtgaa gaacttttcc ctgacatcca atctaagcct tccctccttg aggttagatc    7980 actccccct tgtgctatca ctgtctactc ttgtaaaaag ttgattctcc tccttttgg    8040 aggttgcaa tgaggtctcc ttgcagcctt cttctcttct gcaggatgaa caagcccagc    8100 ccctcagcc tgtctttata ggagaggtgc tccagccctc tgatcatctt tgtggccctc    8160 tctggaccc gctccaagag ctccacatct ttcctgtact gggggcccca ggcctgaatg    8220 agtactcca gatggggcct caaaagagca gagtaaagag ggacaatcac cttcctcacc    8280 tgctggcca gccctcttct gatggagccc tggatacaac tggctttctg agctgcaact    8340 ctccttatc agttccacta ttaaaacagg aacaatacaa caggtgctga tggccagtgc    8400 gagttttc acacttcttc atttcggtag atcttagatg aggaacgttg aagttgtgct    8460 ctgcgtgtg cttcttcctc ctcaaatact cctgcctgat acctcacccc acctgccact    8520 aatggctcc atggccccct gcagccaggg ccctgatgaa cccggcactg cttcagatgc    8580 gtttaatag cacagtatga ccaagttgca cctatgaata cacaaacaat gtgttgcatc    8640 ttcagcact tgagaagaag agccaaattt gcattgtcag gaaatggttt agtaattctg    8700 caattaaaa cttgtttatc taccatggct gttttatgg ctgttagtag tggtacactg    8760 tgatgaaca atggctatgc agtaaaatca agactgtaga tattgcaaca gactataaaa    8820 tcctctgtg gcttagccaa tgtggtactt cccacattgt ataagaaatt tggcaagttt    8880 gagcaatgt ttgaagtgtt gggaaatttc tgtatactca agagggcgtt tttgacaact    8940 tagaacaga ggaatcaaaa gggggtggga ggaagttaaa agaagaggca ggtgcaagag    9000
agcttgcagt cccgctgtgt gtacgacact ggcaacatga ggtctttgct aatcttggtg    9060
ctttgcttcc tgccctggc tgccttaggg tgcgatctgc ctcagaccca cagcctgggc    9120
agcaggagga ccctgatgct gctggctcag atgaggagaa tcagcctgtt tagctgcctg    9180
aaggataggc acgattttgg ctttcctcaa gaggagtttg gcaaccagtt tcagaaggct    9240
gagaccatcc ctgtgctgca cgagatgatc cagcagatct ttaacctgtt tagcaccaag    9300
gatagcagcg ctgcttggga tgagaccctg ctggataagt tttacaccga gctgtaccag    9360
cagctgaacg atctggaggc ttgcgtgatc cagggcgtgg gcgtgaccga gacccctctg    9420
atgaaggagg atagcatcct ggctgtgagg aagtactttc agaggatcac cctgtacctg    9480
aaggagaaga gtacagcccc ctgcgcttgg gaagtcgtga gggctgagat catgaggagc    9540
tttagcctga gcaccaacct gcaagagagc ttgaggtcta aggagtaaaa agtctag     9597
```

<210> SEQ ID NO 76
<211> LENGTH: 28
<212> TYPE: DNA
<213> ORGANISM: Artificial Sequence
<220> FEATURE:
<223> OTHER INFORMATION: Primer ALV-SIN-1

<400> SEQUENCE: 76

```
atgcgcgcat tggtaattga tcggctgg                                            28

<210> SEQ ID NO 77
<211> LENGTH: 80
<212> TYPE: DNA
<213> ORGANISM: Artificial Sequence
<220> FEATURE:
<223> OTHER INFORMATION: Primer ALV-SIN-2

<400> SEQUENCE: 77
atatgcggcc gcggtaccgc ccgggcatcg atatcaagct tacggttcac taaacgagct         60
ctgcttatat agacctccca                                                     80

<210> SEQ ID NO 78
<211> LENGTH: 59
<212> TYPE: DNA
<213> ORGANISM: Artificial Sequence
<220> FEATURE:
<223> OTHER INFORMATION: Primer ALV-SIN-3

<400> SEQUENCE: 78
atatgcggcc gcgtcgacgg ccggccagat ctgctgagcc ggtcgctacc attaccagt          59

<210> SEQ ID NO 79
<211> LENGTH: 28
<212> TYPE: DNA
<213> ORGANISM: Artificial Sequence
<220> FEATURE:
<223> OTHER INFORMATION: Primer ALV-SIN-4

<400> SEQUENCE: 79
atacgcgtat tccctaacga tcacgtcg                                            28

<210> SEQ ID NO 80
<211> LENGTH: 21
<212> TYPE: DNA
<213> ORGANISM: Artificial Sequence
<220> FEATURE:
<223> OTHER INFORMATION: Primer ALV-SIN-5

<400> SEQUENCE: 80
ctgaagtgta aggaatgtaa g                                                   21

<210> SEQ ID NO 81
<211> LENGTH: 30
<212> TYPE: DNA
<213> ORGANISM: Artificial Sequence
<220> FEATURE:
<223> OTHER INFORMATION: Primer ALV-SIN-6

<400> SEQUENCE: 81
gcgcgtctca tcccctccc tatgcaaaag                                           30

<210> SEQ ID NO 82
<211> LENGTH: 37
<212> TYPE: DNA
<213> ORGANISM: Artificial Sequence
<220> FEATURE:
<223> OTHER INFORMATION: Primer ALV-SIN-7

<400> SEQUENCE: 82
gggcgtctca gggacggatt ggacgaacca ctgaatt                                  37

<210> SEQ ID NO 83
```

```
<211> LENGTH: 20
<212> TYPE: DNA
<213> ORGANISM: Artificial Sequence
<220> FEATURE:
<223> OTHER INFORMATION: Primer ALV-SIN-8

<400> SEQUENCE: 83
ttagtgcttt acggcacctc                                              20

<210> SEQ ID NO 84
<211> LENGTH: 38
<212> TYPE: DNA
<213> ORGANISM: Artificial Sequence
<220> FEATURE:
<223> OTHER INFORMATION: Primer ALV-SIN-9

<400> SEQUENCE: 84
gacggatccg ataccgtccc tatttttgtg tttgcttc                           38

<210> SEQ ID NO 85
<211> LENGTH: 30
<212> TYPE: DNA
<213> ORGANISM: Artificial Sequence
<220> FEATURE:
<223> OTHER INFORMATION: Primer ALV-SIN-10

<400> SEQUENCE: 85
taacggatcc tagactttt actccttaga                                    30
```

AVIANS CONTAINING A LYSOZYME PROMOTER TRANSGENE

This application is a continuation-in-part of U.S. patent application Ser. No. 10/114,739, filed Apr. 1, 2002, now issued U.S. Pat. No. 7,199,729, issued Apr. 3, 2007, which claims the benefit from provisional application Ser. No. 60/351,550 filed Jan. 25, 2002 and is a continuation-in-part of U.S. patent application Ser. No. 09/922,549, filed Aug. 3, 2001, now issued U.S. Pat. No. 7,176,300, issued Feb. 13, 2007, which claims the benefit of provisional application Ser. No. 60/280,004, filed Mar. 30, 2001. The disclosure of U.S. patent application Ser. No. 10/114,739 (U.S. Pat. No. 7,199,729) and Ser. No. 09/922,549 (U.S. Pat. No. 7,176,300) are incorporated herein in their entirety by reference.

FIELD OF THE INVENTION

The present invention relates generally to the use of avian lysozyme gene expression control or controlling regions, for example, from the chicken. More specifically, the invention relates to recombinant nucleic acids and expression vectors, transfected cells and transgenic animals, in particular transgenic avians such as transgenic chickens, that contain an avian lysozyme gene expression controlling regions operably linked to a polypeptide-encoding nucleic acid and, optionally, a chicken lysozyme 3' domain. The present invention also relates to the expression of a polypeptide-encoding nucleic acid under the control of an exogenous avian lysozyme gene expression controlling region.

BACKGROUND

The field of transgenics was initially developed to understand the action of a single gene in the context of the whole animal and the phenomena of gene activation, expression and interaction. Transgenics technology has also been used to produce models for various diseases in humans and other animals and is among the most powerful tools available for the study of genetics, and the understanding of genetic mechanisms and function. From an economic perspective, the use of transgenic technology to convert animals into "protein factories" for the production of specific proteins or other substances of pharmaceutical interest (Gordon et al., 1987, Biotechnology 5: 1183-1187; Wilmut et al., 1990, Theriogenology 33: 113-123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require lactating animals, with the attendant costs of maintaining individual animals or herds of large species, including cows, sheep, or goats.

Historically, transgenic animals have been produced almost exclusively by microinjection of the fertilized egg. The pronuclei of fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (e.g., Krimpenfort et al., in U.S. Pat. No. 5,175,384).

One system that holds potential for expressing foreign proteins is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct, which is lined with tubular gland cells. These cells secrete the egg-white proteins, including ovalbumin, lysozyme, ovomucoid, conalbumin and ovomucin, into the lumen of the magnum where they are deposited onto the avian embryo and yolk.

Advantages of using the hen oviduct as a protein bioreactor include the high levels of protein production, the promise of proper folding and post-translation modification of the target protein, the ease of product recovery, and the shorter developmental period of birds such as chickens compared to other animal species. As a result, efforts have been made to create transgenic chickens, for example, by expressing heterologous proteins in the oviduct by means of microinjection of DNA. See, for example, PCT Publication WO 97/47739, the disclosure of which is incorporated in its entirety herein by reference.

The chicken lysozyme gene is highly expressed in the myeloid lineage of hematopoietic cells, and in the tubular glands of the mature hen oviduct. See, for example, Hauser et al., 1981, Hematol. and Blood Transfusion 26: 175-178; Schutz et al., 1978, Cold Spring Harbor Symp. Quart. Biol. 42: 617-624 (the disclosures of which are incorporated in their entirety herein by reference). In one embodiment, elements of the regulatory region of the lysozyme locus can extend over at least 12 kb of DNA 5' upstream of the transcription start site and can comprise a number of elements that have been individually isolated and characterized. Known elements include three enhancer sequences at about −6.1 kb, −3.9 kb, and −2.7 kb (Grewal et al., 1992, Mol. Cell. Biol. 12: 2339-2350; Banifer et al., 1996, J. Mol. Med. 74: 663-671), a hormone responsive element (Hecht et al., 1988, E.M.B.O. J. 7: 2063-2073), a silencer element and a complex proximal promoter. The constituent elements of the lysozyme gene expression control region are identifiable as DNAase 1 hypersensitive chromatin sites (DHS). They may be differentially exposed to nuclease digestion depending upon the differentiation stage of the cell. For example, in the multipotent progenitor stage of myelomonocytic cell development, or in erythroblasts, the silencer element is a DHS. At the myeloblast stage, a transcription enchancer located −6.1 kb upstream from the gene transcription start site is a DHS, while at the later monocytic stage another enhancer, at −2.7 kb becomes DNAase sensitive (Huber et al., 1995, DNA and Cell Biol. 14: 397-402).

Scattered throughout the chicken genome, including the chicken lysozyme locus, are short stretches of nucleic acid that resemble features of Long Terminal Repeats (LTRs) of retrovirus. The function of these elements is unclear but most likely help define the DHS regions of a gene locus (Stein et al., 1983, Proc. Natl. Acad. Sci. U.S.A. 80: 6485-6489).

Flanking the lysozyme gene, including the regulatory region, are matrix attachment regions (5' MAR and 3' MAR), alternatively referred to as "scaffold attachment regions" or SARs. The outer boundaries of the chicken lysozyme locus have been defined by the MARs (Phi-Van et al., 1988, E.M.B.O. J. 7: 655-664; Phi-Van, L. and Stratling, W. H., 1996, Biochem. 35: 10735-10742). Deletion of a 1.32 kb or a 1.45 kb halves region, each comprising half of a 5' MAR, reduces positional variation in the level of transgene expression (Phi-Van and Stratling, supra).

The 5' matrix-associated region (5' MAR), located about −11.7 kb upstream of the chicken lysozyme transcription start site, can increase the level of gene expression by limiting the positional effects exerted against a transgene (Phi-Van et al., 1988, supra). At least one other MAR is located 3' downstream of the protein encoding region. Although MAR nucleic acid sequences are conserved, little cross-hybridization is seen, indicating significant overall sequence variation. However, MARs of different species can interact with the nucleomatrices of heterologous species, to the extent that the chicken lysozyme MAR can associate with the plant tobacco nucleomatrix as well as that of the chicken oviduct cells (Miynarona et al., 1994, Cell 6: 417-426; von Kries et al., 1990, Nucleic Acids Res. 18: 3881-3885).

Gene expression must be considered not only from the perspective of cis-regulatory elements associated with a gene, and their interactions with trans-acting elements, but also with regard to the genetic environment in which they are located. Chromosomal positioning effects (CPEs), therefore, are the variations in levels of transgene expression associated with different locations of the transgene within the recipient genome. An important factor governing CPE upon the level of transgene expression is the chromatin structure around a transgene, and how it cooperates with the cis-regulatory elements. The cis-elements of the lysozyme locus are confined within a single chromatin domain (Bonifer et al., 1996, supra; Sippel et al., pgs. 133-147 in Eckstein F. & Lilley D. M. J. (eds), "Nucleic Acids and Molecular Biology", Vol. 3, 1989, Springer.

Deletion of a cis-regulatory element from a transgenic lysozyme locus is sufficient to reduce or eliminate positional independence of the level of gene expression (Banifer et al., 1996, supra). There is also evidence indicating that positional independence conferred on a transgene requires the cotransfer of many kilobases of DNA other than just the protein encoding region and the immediate cis-regulatory elements.

The lysozyme promoter region of chicken is active when transfected into mouse fibroblast cells and linked to a reporter gene such as the bacterial chloramphenicol acetyltransferase (CAT) gene. The promoter element is also effective when transiently transfected into chicken promacrophage cells. In each case, however, the presence of a 5' MAR element increased positional independency of the level of transcription (Stief et al., 1989, Nature 341: 343-345; Sippel et al., pgs. 257-265 in Houdeline L. M. (ed), "Transgenic Animals: Generation and Use").

The ability to direct the insertion of a transgene into a site in the genome of an animal where the positional effect is limited offers predictability of results during the development of a desired transgenic animal, and increased yields of the expressed product. Sippel and Steif disclose, in U.S. Pat. No. 5,731,178, methods to increase the expression of genes introduced into eukaryotic cells by flanking a transcription unit with scaffold attachment elements, in particular the 5' MAR isolated from the chicken lysozyme gene. The transcription unit disclosed by Sippel and Steif was an artificial construct that combined only the −6.1 kb enhancer element and the proximal promoter element (base position −579 to +15) from the lysozyme gene. Other promoter associated elements were not included. However, although individual cis-regulatory elements have been isolated and sequenced, together with short regions flanking DNA, the entire nucleic acid sequence comprising the functional 5' upstream region of the lysozyme gene has not been determined in its entirety and therefore not employed as a functional promoter to allow expression of a heterologous transgene.

What is needed are efficient transcription promoters that will allow expression of a transgene in avian cells, in particular, in the oviduct cells (e.g., tubular gland cells) of a transgenic avian.

SUMMARY OF THE INVENTION

Briefly described, the present invention relates to nucleic acids comprising avian lysozyme gene expression controlling regions which may be isolated. In one particularly useful aspect, the invention provides for transgenic avians, and methods of there production, wherein the transgenic avians contain in their genome an exogenous nucleotide sequence comprising an avian lysozyme gene expression controlling region. Typically, the exogenous avian lysozyme gene expression controlling region is operably linked to an exogenous or heterologous coding sequence (e.g., a coding sequence which encodes an exogenous or heterologous peptide or protein). In one useful embodiment, the exogenous coding sequence is expressed in an oviduct cell of the transgenic avian, for example, in a tubular gland cell of the transgenic avian. Typically, in accordance with the invention, the expressed product is secreted from the oviduct cell, for example, secreted from the oviduct cell (e.g., tubular gland cell) into the oviduct.

Examples of transgenic avians that can be produced in accordance with the present invention include, without limitation, transgenic chickens, transgenic turkeys, transgenic ducks and transgenic quail. The transgenic avian may be a chimeric transgenic avian. That is, some but not all, of the cells of the transgenic avian may contain an exogenous nucleotide sequence which includes a recombinant lysozyme gene expression controlling region. Such chimeric avians can be germ-line chimerics in which some of the avian's germ cells contain the exogenous nucleotide sequence. Such germ-line chimeric avians can give rise to transgenic avians in which essentially all the cells of the avians contain the exogenous nucleotide sequence containing a recombinant lysozyme gene expression controlling region, as is understood in the art of animal breeding and avian transgenesis. See, for example, US patent publication No. 2006/0015960, filed Jun. 24, 2005, the disclosure of which is incorporated in its entirety herein by reference.

In one particularly useful embodiment, the lysozyme gene expression controlling region is linked to an exogenous nucleotide sequence such as a nucleotide sequence encoding a therapeutic protein, e.g., a human protein (i.e., a protein normally produced in a human). In accordance with the invention, the transgenic avian can produce the exogenous protein, for example, in the oviduct cells of the transgenic avian. In such instance the exogenous protein is typically deposited in egg white produced by the transgenic avian. In one particularly useful aspect, the transgenic avian can produce an egg such as a hard shelled egg containing the exogenous protein.

The invention specifically contemplates the application of any useful avian lysozyme gene expression controlling region encompassed in SEQ ID NO: 67 for producing transgenic avians of the invention. For example, the invention contemplates the use of nucleotide sequence corresponding to any fragment or portion of SEQ ID NO: 67 having gene expression controlling activity (e.g., promoter activity), for the production of transgenic avians as disclosed herein. Also contemplated is the use of nucleotide sequences that can function as a gene expression controlling region (e.g., function as a promoter) in which the nucleotide sequences are at least about 75% identical to the nucleotide sequence depicted in SEQ ID NO: 67. In addition, it is contemplated that such nucleotide sequences can be at least about 80%, and at least about 85%, and at least about 90%, and at least about 91%, and at least about 92%, and at least about 93%, and at least about 94%, and at least about 95%, and at least about 96%, and at least about 97%, and at least about 98%, and at least about 99% identical to the nucleotide sequence depicted in SEQ ID NO: 67. Also contemplated is the use of nucleotide sequences that can function as a gene expression controlling region (e.g., function as a promoter) in which the nucleotide sequences are at least about 75% identical to a fragment of the nucleotide sequence depicted in SEQ ID NO: 67. In addition, it is contemplated that nucleotide sequences that can function as a gene expression controlling region can be at least about 80%, and at least about 85%, and at least about 90%, and at least about 91%, and at least about 92%, and at least about 93%, and at least about 94%, and at least about 95%, and at least about 96%, and at least about 97%, and at least about 98%, and at least about 99% identical to a fragment of the nucleotide sequence depicted in SEQ ID NO: 67.

Examples of specifically contemplated sequences for the production of transgenic avians (including chimeras, e.g., germ-line chimeras and their progeny birds) such as transgenic chickens, transgenic quail and transgenic turkeys include, a nucleotide sequence at least 80% identical to nucleotides 7665 to 11863 of SEQ ID NO: 67 and a nucleotide sequence at least 90% identical to nucleotides 7665 to 11863 of SEQ ID NO: 67 and a nucleotide sequence at least 95% identical to nucleotides 7665 to 11863 of SEQ ID NO: 67 and a nucleotide sequence at least 96% identical to nucleotides 7665 to 11863 of SEQ ID NO: 67 and a nucleotide sequence at least 97% identical to nucleotides 7665 to 11863 of SEQ ID NO: 67 and a nucleotide sequence at least 98% identical to nucleotides 7665 to 11863 of SEQ ID NO: 67 and a nucleotide sequence at least 99% identical to nucleotides 7665 to 11863 of SEQ ID NO: 67 and a nucleotide sequence identical to nucleotides 7665 to 11863 of SEQ ID NO: 67; a nucleotide sequence at least 80% identical to nucleotides 5381 to 11863 of SEQ ID NO: 67 and a nucleotide sequence at least 90% identical to nucleotides 5381 to 11863 of SEQ ID NO: 67 and a nucleotide sequence at least 95% identical to nucleotides 5381 to 11863 of SEQ ID NO: 67 and a nucleotide sequence at least 96% identical to nucleotides 5381 to 11863 of SEQ ID NO: 67 and a nucleotide sequence at least 97% identical to nucleotides 5381 to 11863 of SEQ ID NO: 67 and a nucleotide sequence at least 98% identical to nucleotides 5381 to 11863 of SEQ ID NO: 67 and a nucleotide sequence at least 99% identical to nucleotides 5381 to 11863 of SEQ ID NO: 67 and a nucleotide sequence identical to nucleotides 5381 to 11863 of SEQ ID NO: 67; a nucleotide sequence at least 80% identical to nucleotides 9159 to 11863 of SEQ ID NO: 67 and a nucleotide sequence at least 90% identical to nucleotides 9159 to 11863 of SEQ ID NO: 67 and a nucleotide sequence at least 95% identical to nucleotides 9159 to 11863 of SEQ ID NO: 67 and a nucleotide sequence at least 96% identical to nucleotides 9159 to 11863 of SEQ ID NO: 67 and a nucleotide sequence at least 97% identical to nucleotides 9159 to 11863 of SEQ ID NO: 67 and a nucleotide sequence at least 98% identical to nucleotides 9159 to 11863 of SEQ ID NO: 67 and a nucleotide sequence at least 99% identical to nucleotides 9159 to 11863 of SEQ ID NO: 67 and a nucleotide sequence identical to nucleotides 9159 to 11863 of SEQ ID NO: 67.

Often, the exogenous nucleotide sequence which contains the recombinant lysozyme gene expression controlling region also includes a vector. That is, the nucleotide sequence which is incorporated into the genome of the transgenic avian (i.e., the transgene) can include a vector. The invention contemplates any useful vector being part of the transgene including, without limitation, a plasmid vector, a viral vector and an artificial chromosome.

In one embodiment, an avian lysozyme gene expression controlling region of the invention, such as one which is encompassed in SEQ ID NO: 67 as described herein, is employed in a SIN vector to produce a transgenic avian (e.g., transgenic chicken) in accordance with the invention. In another embodiment, an avian lysozyme gene expression controlling region of the invention such as one encompassed in SEQ ID NO: 67 as describe above is employed in a retroviral vector which does not contain an antibiotic resistance marker gene to produce a transgenic avian (e.g., transgenic chicken) in accordance with the invention. In another embodiment, an avian lysozyme gene expression controlling region of the invention such as one encompassed in SEQ ID NO: 67 as describe above is employed in a SIN vector which does not contain an antibiotic resistance marker gene (i.e., does not contain a promoter for an antibiotic resistance marker) to produce a transgenic avian (e.g., transgenic chicken) in accordance with the invention.

In one embodiment, an isolated nucleic acid of the present invention is useful for reducing the chromosomal positional effect of a transgene operably linked to the lysozyme gene expression control region and transfected into a recipient cell. By isolating a region of the avian genome extending from 5' upstream of a 5' MAR of the lysozyme locus to the junction between the signal peptide sequence and a polypeptide-encoding region, cis-elements are also included to allow gene expression in a tissue-specific manner. The lysozyme promoter region of the present invention, therefore, will allow expression of an operably linked heterologous nucleic acid insert in a transfected avian cell such as, for example, an oviduct cell.

One aspect of the present invention provides a novel isolated nucleic acid that is located immediately 5' upstream of the native lysozyme-encoding region of the chicken lysozyme gene locus. The novel isolated avian nucleic acid sequence encoding a lysozyme gene expression control region comprises at least one 5' matrix attachment region, an intrinsically curved DNA region, at least one transcription enhancer element, a negative regulatory element, at least one hormone responsive element, at least one avian CR1 repeat element, and a proximal lysozyme promoter and signal peptide-encoding region. Interspersed between these constituent elements are stretches of nucleic acid that serve at least to organize the above elements in an ordered or functional array relative to a polypeptide-encoding region.

In one embodiment of the present invention the gene expression controlling region, e.g., promoter of the invention is isolated from a chicken.

The promoter of the present invention may be operably linked with a selected nucleic acid insert, wherein the nucleic acid insert encodes a polypeptide desired to be expressed in a transfected cell. The nucleic acid insert may be placed in frame with a signal peptide sequence. Translation initiation may start with the signal peptide and continue through the nucleic acid insert, thereby producing an expressed polypeptide having the desired amino acid sequence.

The sequence of the expressed nucleic acid insert may be optimized for codon usage by a host cell. This may be determined from the codon usage of at least one, and preferably more than one, proteins expressed in a chicken cell. For example, the codon usage may be determined from the nucleic acid sequences encoding the proteins ovalbumin, lysozyme, ovomucin and ovotransferrin of chicken.

The recombinant DNA of the present invention may further comprise a polyadenylation signal sequence that will allow the transcript directed by the novel lysozyme gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like.

The recombinant DNA of the invention may comprise the chicken lysozyme 3' domain operably linked to the nucleic acid insert encoding a polypeptide. The 3' domain may include a 3' untranslated region, a polyadenylation signal and a 3' MAR that may reduce positional variation in transgenic avians.

Yet another aspect of the present invention is expression vectors suitable for delivery to a recipient cell or animal for expression of the therein. The expression vector of the present invention may comprise an isolated avian lysozyme gene expression control region operably linked to a nucleic acid insert encoding a polypeptide, and optionally a polyadenylation signal sequence. The expression vector may further comprise a bacterial plasmid sequence, a viral nucleic acid sequence, or fragments or variants thereof that may allow for replication of the vector in a suitable host.

Another aspect of the present invention is a method of expressing a heterologous polypeptide in a eukaryotic cell by transfecting the cell with a recombinant DNA comprising an avian lysozyme gene expression controlling region operably linked to a nucleic acid insert encoding a polypeptide and, optionally, a polyadenylation signal sequence, and culturing the transfected cell in a medium suitable for expression of the heterologous polypeptide under the control of the avian lysozyme gene expression control region.

Also within the scope of the present invention are recombinant cells, tissues and animals containing non-naturally occurring recombinant nucleic acid molecules according to the present invention and described above. In one embodiment of the present invention, the transformed cell is a chicken oviduct cell and the nucleic acid insert comprises the chicken lysozyme gene expression control region, a nucleic acid insert encoding a human interferon α2 and codon optimized for expression in an avian cell, and an SV40 polyadenylation sequence.

Another aspect of the invention provides for a vector comprising a first and second coding sequence and a promoter in operational and positional relationship to the first and second coding sequence to express the first and second coding sequence in an avian oviduct. In this aspect, the vector may include an internal ribosome entry site (IRES) element positioned between the first and second coding sequence, wherein the first coding sequence codes for protein X and the second coding sequence codes for protein Y, and wherein one or both of protein X and protein Y are deposited into the egg (e.g., egg white) of a hard shell egg.

For example, protein X maybe a light chain (LC) of a monoclonal antibody and protein Y may be a heavy chain (HC) of a monoclonal antibody. Alternatively, the protein encoded by the second coding sequence (e.g., enzyme) may be capable of providing post-translational modification of the protein encoded by the first coding sequence. The vector optionally includes additional coding sequences and additional IRES elements, such that each coding sequence in the vector is separated from another coding sequence by an IRES element. Other examples of employing an IRES which are contemplated for use in the present invention are disclosed in, for example, U.S. patent application Ser. No. 11/047,184, filed Jan. 31, 2005, now issued U.S. Pat. No. 7,335,761, issued Feb. 26, 2008, the disclosure of which is incorporated in its entirety herein by reference.

The invention also contemplates methods of producing an avian egg which contains proteins such as therapeutic or pharmaceutical proteins including monoclonal antibodies, enzymes and other proteins. Such methods may include providing a vector with a promoter, coding sequences, and at least one IRES element; creating transgenic cells or tissue by introducing the vector into avian embryonic blastodermal cells, wherein the vector sequence is randomly inserted into the avian genome; and deriving a mature transgenic avian from the transgenic cells or tissue. The transgenic avian so derived may express the coding sequences in its oviduct, and the resulting protein secreted into the oviduct lumen, so that the protein is deposited into the egg white of a hard shell egg. In addition, the invention includes progeny of the transgenic avians which produce eggs containing the recombinant protein. Typically, the progeny will either contain the transgene in essentially all the cells of the bird or none of the cells of the progeny bird will contain the transgene.

One important aspect of the present invention relates to avian hard shell eggs (e.g., chicken hard shell eggs) which contain an exogenous peptide or protein including, but not limited to, a pharmaceutical protein. The exogenous peptide or protein may be encoded by a transgene of a transgenic avian. In one embodiment, the exogenous peptide or protein (e.g., pharmaceutical protein) is glycosylated. The protein may be present in any useful amount. In one embodiment, the protein is present in an amount in a range of between about 0.1 µg per hard-shell egg and about 1 gram per hard-shell egg. In another embodiment, the protein is present in an amount in a range of between about 1 µg per hard-shell egg and about 1 gram per hard-shell egg. For example, the protein may be present in an amount in a range of between about 10 µg per hard-shell egg and about 1 gram per hard-shell egg (e.g., a range of between about 10 µg per hard-shell egg and about 400 milligrams per hard-shell egg). In one embodiment, the protein is present in an amount in a range of between about 500 µg per hard-shell egg and about 50 milligrams per hard-shell egg.

In one embodiment, the exogenous protein, for example, the exogenous pharmaceutical protein, is present in the egg white of the egg. In one embodiment, the protein is present in an amount in a range of between about 1 ng per milliliter of egg white and about 0.2 gram per milliliter of egg white. For example, the protein may be present in an amount in a range of between about 0.1 µg per milliliter of egg white and about 0.2 gram per milliliter of egg white (e.g., the protein may be present in an amount in a range of between about 1 µg per milliliter of egg white and about 100 milligrams per milliliter of egg white. In one embodiment, the protein is present in an amount in a range of between about 1 µg per milliliter of egg white and about 50 milligrams per milliliter of egg white. For example, the protein may be present in an amount in a range of about 1 µg per milliliter of egg white and about 10 milligrams per milliliter of egg white (e.g., the protein may be present in an amount in a range of between about 1 µg per milliliter of egg white and about 5 milligrams per milliliter of egg white). In one embodiment, the protein is present in an amount in a range of about 50 µg per milliliter of egg white and about 5 milligrams per milliliter of egg white.

The invention contemplates the production of hard shell eggs containing any useful protein including one or more pharmaceutical proteins. Such proteins include, but are not limited to, hormones, immunoglobulins or portions of immunoglobulins, cytokines (e.g., GM-CSF, G-CSF, erythropoietin and interferon) and CTLA4. The invention also includes the production of hard shell eggs containing fusion proteins including, but not limited to, immunoglobulins or portions of immunoglobulins fused to certain useful peptide sequences. In one embodiment, the invention provides for the production of hard shell eggs containing an antibody Fc fragment. For example, the eggs may contain an Fc-CTLA4 fusion protein.

The avians developed from the blastodermal cells into which the vector has been introduced are the G0 generation and are referred to as "founders". Founder birds are typically chimeric for each inserted transgene. That is, only some of the cells of the G0 transgenic bird contain the transgene(s). The G0 generation typically is also hemizygous for the transgene(s). The G0 generation may be bred to non-transgenic animals to give rise to G1 transgenic offspring which are also hemizygous for the transgene and contain the transgene(s) in essentially all of the bird's cells. The G1 hemizygous offspring may be bred to non-transgenic animals giving rise to G2 hemizygous offspring or may be bred together to give rise to G2 offspring homozygous for the transgene. Substantially all of the cells of birds which are positive for the transgene that are derived from G1 offspring will contain the transgene(s). In one embodiment, hemizygotic G2 offspring from the same line can be bred to produce G3 offspring homozygous for the transgene. In one embodiment, hemizygous G0 animals are bred together to give rise to homozygous G1 offspring containing two copies of the transgene(s) in each cell of the animal. These are merely examples of certain useful breeding schemes and the present invention contemplates the employment of any useful breeding scheme such as those known to individuals of ordinary skill in the art.

Any useful combination of features described herein is included within the scope of the present invention provided that the features included in any such combination are not mutually inconsistent as will be apparent from the context, this specification, and the knowledge of one of ordinary skill in the art Additional objects and aspects of the present invention will become more apparent upon review of the detailed description set forth below when taken in conjunction with the accompanying figures, which are briefly described as follows.

BRIEF DESCRIPTION OF THE FIGURES

FIG. 1a, FIG. 1b, FIG. 1c and FIG. 1d illustrate the primers (SEQ ID NOS: 1-64) used in the sequencing of the lysozyme gene expression controlling region of SEQ ID NO: 67.

FIG. 3a, FIG. 3b, FIG. 3c and FIG. 3d illustrate the nucleic acid sequence (SEQ ID NO: 65) comprising the chicken lysozyme gene expression controlling region shown in SEQ ID NO: 67, the nucleic acid sequence of SEQ ID NO: 66 encoding the chicken expression optimized human interferon α2b (IFNMAGMAX) which is underlined in the figures and the SV40 polyadenylation signal sequence shown in SEQ ID NO: 68, which is in bold print in the figures.

FIG. 4 illustrates the nucleic acid sequence of SEQ ID NO: 66 encoding the chicken expression optimized human interferon α2b (IFNMAGMAX).

FIG. 5a, FIG. 5b, FIG. 5c and FIG. 5d illustrate the nucleic acid sequence of SEQ ID NO: 67 encoding the chicken lysozyme gene expression controlling region.

FIG. 6 illustrates the nucleic acid sequence of SEQ ID NO: 68 encoding the SV40 polyadenylation signal sequence.

FIG. 7a, FIG. 7b and FIG. 7c illustrate a portion of the nucleic acid sequence of SEQ ID NO: 69 encoding the chicken lysozyme 3' domain.

FIG. 8a, FIG. 8b, FIG. 8c, FIG. 8d, FIG. 8e, FIG. 8f, FIG. 8g, FIG. 8h, FIG. 8i and FIG. 8j illustrate the nucleic acid sequence of SEQ ID NO: 74 encoding the lysozyme gene expression controlling region shown in SEQ ID NO: 67 linked to the nucleic acid insert encoding the chicken expression-optimized human interferon α2b (IFNMAGMAX) (SEQ ID NO: 66) which is underlined in the figure and is in turn linked to the chicken lysozyme 3' domain (SEQ ID NO: 69) which is shown in bold print. A fragment of a pBluescript cloning vector approximately 44 nucleotides in length is present between the IFNMAGMAX and the lysozyme 3' domain and is shown in lower case (FIG. 8f). The nucleotide sequence shown in lower case 3' of the chicken lysozyme 3' domain is nucleotide sequence from the cloning vectors pPolyIII and pBluescript (See, FIG. 8i to 8j).

DETAILED DESCRIPTION

Figure 2:
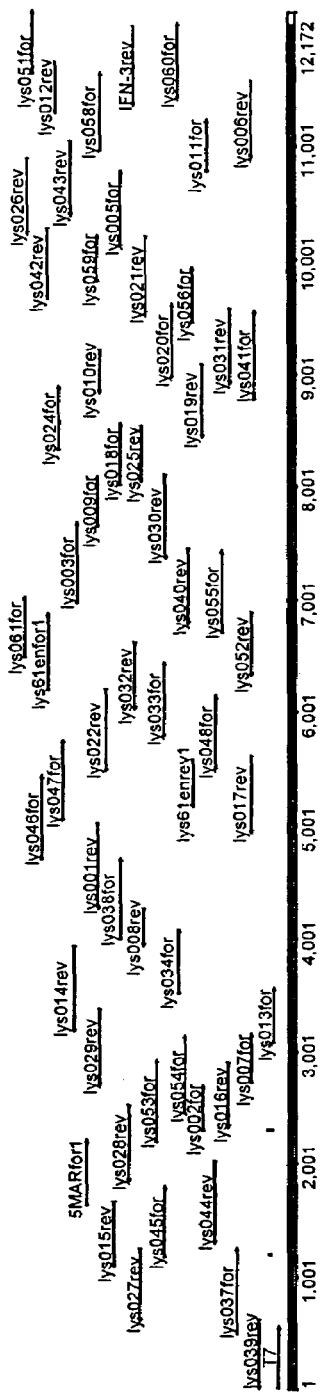
FIG. 2 schematically illustrates the approximately 12 kb lysozyme gene expression controlling region shown in SEQ ID NO: 67) indicating the relative positions and orientations of the primers (SEQ ID NOS: 1-64) used in the sequencing thereof.
Figure 9:
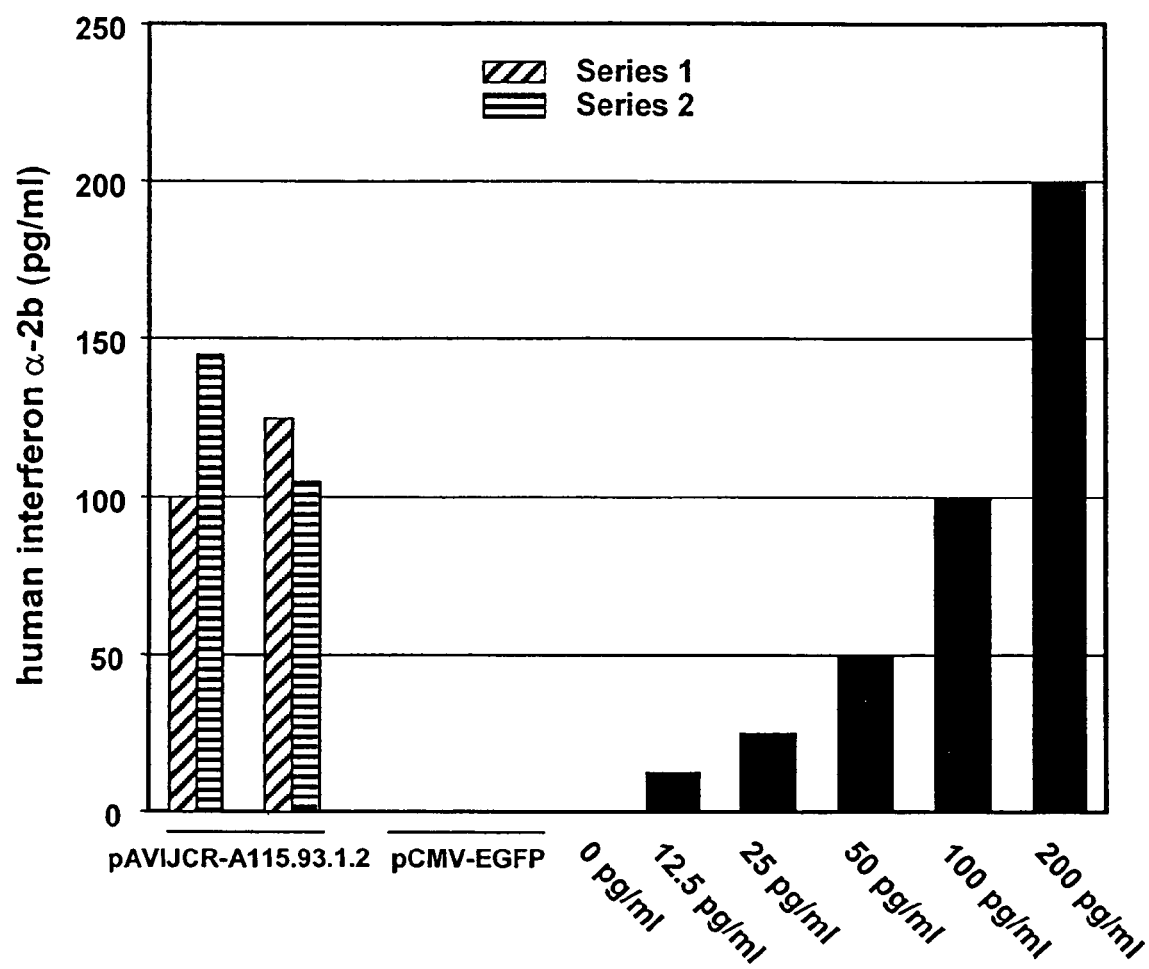
FIG. 9 illustrates the yield of the human interferon α2b, optimized for chicken expression (IFNMAGMAX), in transfected quail oviduct cultured cells.

Reference now will be made in detail to certain embodiments of the invention, one or more examples of which are illustrated in the accompanying drawings. Each example is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

This description uses gene nomenclature accepted by the Cucurbit Genetics Cooperative as it appears in the Cucurbit Genetics Cooperative Report 18:85 (1995), herein incorporated by reference in its entirety. Using this gene nomenclature, genes are symbolized by italicized Roman letters. If a mutant gene is recessive to the normal type, then the symbol and name of the mutant gene appear in italicized lower case letters.

For convenience, certain terms employed in the specification, examples, and appended claims are collected here.

Definitions

The term "animal" is used herein to include all vertebrate animals, including avians and may include humans. It also includes an individual animal in all stages of development, including embryonic and fetal stages.

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of Gallus gallus, or chickens, (for example, White Leghorn, Brown Leghorn, Barred-Rock, Sussex, New Hampshire, Rhode Island, Ausstralorp, Minorca, Amrox, California Gray, Italian Partridge-colored), as well as strains of turkeys, pheasants, quails, duck, ostriches and other poultry commonly bred in commercial quantities.

The phrase "based on" or "derived from" as in a retroviral vector being based on or derived from a particular retrovirus or based on a nucleotide sequence of a particular retrovirus mean that the genome of the retroviral vector contains a substantial portion of the nucleotide sequence of the genome of the particular retrovirus. The substantial portion may be a particular gene or nucleotide sequence such as the nucleotide sequence encoding the gag, pol and/or env proteins or other structural or functional nucleotide sequence of the virus genome such as sequences encoding the LTRs or may be substantially the complete retrovirus genome, for example, most (e.g., more than 60% or more than 70% or more than 80% or more than 90%) or all of the retrovirus genome, as will be apparent from the context in the specification as the knowledge of one skilled in the art. Examples of retroviral vectors that are based on or derived from a retrovirus are the NL retroviral vectors (e.g., NLB) which are based on the ALV retrovirus as disclosed in Cosset et al, Journal of Virology (1991) vol 65, p 3388-3394.

The terms "heterologous", "exogenous" and "foreign" are used interchangeably herein and in general refer to a biomolecule such as a nucleic acid or a protein that is not normally found in a certain cell, tissue or other component contained in or produced by an organism. For example, a protein that is heterologous or exogenous to an egg is a protein that is not normally found in the egg.

As used herein, the terms "heterologous", "exogenous" and "foreign" with reference to nucleic acids, such as DNA and RNA, are used interchangeably and refer to nucleic acid that does not occur naturally as part of a chromosome, a genome or cell in which it is present or which is found in a location(s) and/or in amounts that differ from the location(s) and/or amounts in which it occurs in nature. It can be nucleic acid that is not endogenous to the genome, chromosome or cell and has been exogenously introduced into the genome, chromosome or cell. Examples of heterologous DNA include, but are not limited to, a DNA comprising a gene expression control region and DNA that encodes a product or products, for example, RNA or protein product. Examples of heterologous DNA include, but are not limited to, lysozyme gene expression control regions of the invention once isolated from the avian and as used thereafter, e.g., after introduction into an avian genome.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retroviruses such as avian leukosis virus (ALV) retroviral vector, a murine leukemia virus (MLV) retroviral vector, and a lentivirus vector, and the like. In addition, the vector may be a nucleic acid sequence which includes an LTR of an avian leukosis virus (ALV) retroviral vector, a murine leukemia virus (MLV) retroviral vector, or a lentivirus vector. NL vectors such as NLB, NLD and NLA are also contemplated for use in methods of the present invention. Vectors may be derived from bacteriophage nucleic acid, and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes a lysozyme gene expression control region or a variant thereof of the present invention.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term "significant" as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin are suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term coding sequence as used herein refers to nucleotide sequences or nucleic acid sequences (including both RNA or DNA) that encode genetic information for the synthesis of a whole RNA, a whole protein, or any portion of such whole RNA or whole protein. Nucleotide sequences that are not naturally part of a particular organism's genome are referred to as "foreign nucleotide sequences," "heterologous nucleotide sequences" or "exogenous nucleotide sequences". "Heterologous products" are RNAs or proteins encoded by "foreign, heterologous or exogenous nucleotide sequences" and are, therefore, not naturally expressed in the cell. A nucleotide sequence that has been isolated and then reintroduced into the same type (e.g., same species) of organism is not considered to be a naturally occurring part of a particular organism's genome and is therefore considered exogenous or heterologous.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "transcription regulatory sequences" and "gene expression control regions" and "gene expression controlling regions" as used herein refer to nucleotide sequences that are associated with a nucleic acid sequence and which regulate the transcriptional expression of a coding sequence. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter" as used herein refers to the DNA sequence that determines the site of transcription initiation from an RNA polymerase. A "promoter-proximal element" may be a regulatory sequence within about 200 base pairs of the transcription start site.

The terms "matrix attachment regions" or "SAR elements" as used herein refer to DNA sequences having an affinity or intrinsic binding ability for the nuclear scaffold or matrix. The MAR elements of the chicken lysozyme locus were described by Phi-Van et al., 1988, E.M.B.O. J. 76: 665-664 and Phi-Van L. and Stratling, W. H., 1996, Biochem. 35: 10735-10742, the contents of which are incorporated herein by reference in their entireties.

The term "coding region" as used herein refers to a continuous linear arrangement of nucleotides which may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like that are well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a lysozyme gene expression control region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g., low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° C. in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al., 1984, Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. 1989, "Molecular Cloning: A Laboratory Manual", 2nd ed., Cold Spring Harbor Press, the contents of which are herein incorporated by reference in its entirety.

Typically, stringent conditions will be those in which the salt concentration is less than about 1.5 M Na ion, typically about 0.01 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino acid sequences as determined using the algorithm of Karlin and Attschul, 1990, Proc. Natl. Acad. Sci. 87: 2264-2268, modified as in Karlin and Attschul, 1993, Proc. Natl. Acad. Sci. 90: 5873-5877. Such an algorithm is incorporated into the NBLAST and XBLAST programs of Attschul et al., 1990, T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al., 1997, Nucl. Acids Res. 25: 3389-3402. When utilizing BLAST and Gapped BLAST programs, the default parameters of the respective programs (e.g. XBLAST and NBLAST) are used. See ncbi.nlm.nih.gov. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; the antisense transcripts may inhibit transport of the "target RNA", or, the antisense transcripts may inhibit translation of "target RNA".

The term "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises the lysozyme gene expression control region operably linked to a nucleotide sequence coding at least one polypeptide. As used herein, the term "regulatory sequences" includes promoters, enhancers, and other elements that may control gene expression. Standard molecular biology textbooks such as Sambrook et al. eds., 1989, "Molecular Cloning: A Laboratory Manual", 2nd ed., Cold Spring Harbor Press may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell, preferably an avian cell, and more preferably a chicken male germ cell. The enhancement is measured relative to the uptake in the absence of the transfecting agent. Examples of transfecting agents include adenovirus-transferring-polylysine-DNA complexes. These complexes generally augment the uptake of DNA into the cell and reduce its breakdown during its passage through the cytoplasm to the nucleus of the cell. These complexes can be targeted to the male germ cells using specific ligands that are recognized by receptors on the cell surface of the germ cell, such as the c-kit ligand or modifications thereof.

Other preferred transfecting agents include but are not limited to lipofectin, lipfectamine, DIMRIE C, Supeffect, and Effectin (Qiagen), unifectin, maxifectin, DOTMA, DOGS (Transfectam; dioctadecylamidoglycylsp-ermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyeth-yl ammonium bromide), HDEAB (N-n-hexadecylN,N-dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term intragenomic defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, a "transgenic animal" is any animal, such as an avian species, including the chicken, in which one or more of the cells of the avian may contain heterologous nucleic acid introduced by way of human intervention, such as by transgenic techniques well known in the art. The nucleic acid is introduced into an animal, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject polypeptide, e.g., either agonistic or antagonistic forms, or in which the gene has been disrupted. The terms "chimeric animal" or "mosaic animal" are used herein to refer to animals in which a recombinant nucleotide sequence is found, or in which the recombinant nucleotide sequence is expressed in some but not all cells of the animal. The term "tissue-specific chimeric animal" indicates that the recombinant gene is present and/or expressed in some tissues but not others.

As used herein, the term "transgene" means a nucleic acid sequence (encoding, for example, a human protein) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene according to the present invention will include one or more transcriptional regulatory sequences, polyadenylation signal sequences and any other nucleic acid, such as introns, that may be necessary for optimal expression of a selected nucleic acid.

The term "chromosomal positional effect (CPE)" as used herein refers to the variation in the degree of gene transcription as a function of the location of the transcribed locus within the cell genome. Random transgenesis may result in a transgene being inserted at different locations in the genome so that individual cells of a population of transgenic cells may each have at least one transgene, each at a different location and therefore each in a different genetic environment. Each cell, therefore, may express the transgene at a level specific for that particular cell and dependent upon the immediate genetic environment of the transgene. In a transgenic animal, as a consequence, different tissues may exhibit different levels of transgene expression.

Techniques useful for isolating and characterizing the nucleic acids and proteins of the present invention are well known to those of skill in the art and standard molecular biology and biochemical manuals may be consulted to select suitable protocols without undue experimentation. See, for example, Sambrook et al, 1989, "Molecular Cloning: A Laboratory Manual", 2nd ed., Cold Spring Harbor, the content of which is herein incorporated by reference in its entirety.

Abbreviations:

Abbreviations used in the present specification include the following: aa, amino acid(s); bp, base pair(s); cDNA, DNA complementary to RNA; nt, nucleotide(s); SSC, sodium chloride-sodium citrate; DMSO, dimethyl sulfoxide; MAR; matrix attachment region.

Chicken lysozyme gene expression controlling region nucleic acid sequences: A series of PCR amplifications of template chicken genomic DNA were used to isolate the gene expression control region of the chicken lysozyme locus. Two amplification reactions used the PCR primer sets SEQ ID NOS: 1 and 2 and SEQ ID NOS: 3 and 4. The amplified PCR products were united as a contiguous isolated nucleic acid by a third PCR amplification step with the primers SEQ ID NOS: 1 and 4, as described in Example 1 below.

One isolated PCR-amplified product of the invention, comprising about 12 kb of the nucleic acid region 5' upstream of the native chicken lysozyme gene locus, was cloned into the plasmid pCMV-LysSPIFNMM. pCMV-LysSPIFNMM comprises a modified nucleic acid insert encoding a human interferon α2 sequence and an SV40 polyadenylation signal sequence 3' downstream of the interferon encoding nucleic acid. The sequence of SEQ ID NO: 66 of the nucleic acid insert encoding human interferon α2 was in accordance with avian cell codon usage, as determined from the nucleotide sequences encoding chicken ovomucin, ovalbumin, ovotransferrin and lysozyme. The novel chicken lysozyme gene expression control region, interferon-encoding insert and the SV40 polyadenylation signal sequence of the resulting plasmid construct pAVIJCR-A115.93.1.2, constructed as described in Example 1 below, was sequenced using the artificial oligonucleotide primers SEQ ID NOS: 1-64, as illustrated in FIGS. 1 and 2.

The nucleic acid sequence (SEQ ID NO: 65) (GenBank Accession No. AF405538) of the insert in pAVIJCR-A115.93.1.2 is shown in FIG. 3, with the modified human interferon α2 encoding nucleotide sequence of SEQ ID NO: 66 (GenBank Accession No. AF405539) and the novel chicken lysozyme gene expression control region SEQ ID NO: 67 (GenBank Accession No. AF405540) shown in FIGS. 4 and 5 respectively. A polyadenylation signal sequence that is suitable for operably linking to the polypeptide-encoding nucleic acid insert is the SV40 signal sequence of SEQ ID NO: 68, as shown in FIG. 6.

The plasmid pAVIJCR-A115.93.1.2 was restriction digested with enzyme FseI to isolate a 15.4 kb DNA containing the lysozyme 5' matrix attachment region (MAR) and the −12.0 kb lysozyme promoter during the expression of the interferon-encoding insert, as described in Example 2, below. Plasmid pIIIilys was restriction digested with MluI and XhoI to isolate an approximately 6 kb nucleic acids, comprising the 3' lysozyme domain, the sequence of which (SEQ ID NO: 70) is shown in FIG. 7. The 15.4 kb and 6 kb nucleic acids were ligated and the 21.4 kb nucleic acid comprising the nucleic acid sequence of SEQ ID NO: 70 (GenBank Assession No. AF 497473) as shown in FIG. 8 was transformed into recipient STBL4 cells as described in Example 2, below.

The inclusion of the novel isolated avian lysozyme gene expression control region of the present invention upstream of a codon-optimized interferon-encoding sequence in pAVIJCR-A115.93.1.2 allowed expression of the interferon polypeptide in transfected avian cells, as described in Example 5, below. The 3' lysozyme domain shown in SEQ ID NO: 69, when operably linked downstream of the heterologous nucleic acid insert, also assists in providing for expression of the nucleic acid insert as described in Example 7, below. For example, the nucleic acid insert may encode a heterologous polypeptide such as the α2 interferon having sequence of SEQ ID NO: 66 (α2b). The invention also contemplates the use of nucleotide sequences which are at least about 75%, and at least about 80%, and at least about 85%, and at least about 90%, and at least about 91%, and at least about 92%, and at least about 93%, and at least about 94%, and at least about 95%, and at least about 96%, and at least about 97%, and at least about 98%, and at least about 99%, identical to the 3' lysozyme domain such as the 3' lysozyme domain shown in SEQ ID NO: 69. Functional fragments of SEQ ID NO: 66 are also encompassed by the invention.

It is further contemplated that any nucleic acid sequence encoding a polypeptide may be operably linked to the novel isolated avian lysozyme gene expression control region and optionally operably linked to the 3' lysozyme domain SEQ ID NO: 69 so as to be expressed in a transfected avian cell. The plasmid construct pAVIJCR-A115.93.1.2 was transfected into cultured quail oviduct cells, which were then incubated for about 72 hours. ELISA assays of the cultured media showed that the transfected cells synthesized a polypeptide detectable with anti-human interferon α2 antibodies. Plasmid construct pAVIJCR-A212.89.2.1 and pAVIJCR-A212.89.2.3 transfected into chicken myelomonocytic HD11 cells yield detectable human α2b interferon, as described in Example 9 and shown in FIG. 10, below.

One isolated chicken lysozyme gene expression control region of the present invention comprises the nucleotide elements that are positioned 5' upstream of the lysozyme-encoding region of the native chicken lysozyme locus and which are necessary for the regulated expression of a downstream polypeptide-encoding nucleic acid. While not wishing to be bound by any one theory, the inclusion of at least one 5' MAR element in the isolated control region may confer positional independence to a transfected gene operably linked to the novel lysozyme gene expression control region.

Isolated lysozyme gene expression control regions of the present invention can be useful for reducing the chromosomal positional effect of a transgene operably linked to the lysozyme gene expression control region and transfected into a recipient avian cell. By isolating a region of the avian genome extending from a point 5' upstream of a 5' MAR of the lysozyme locus to the junction between the signal peptide sequence and a polypeptide-encoding region, cis-regulatory elements are also included that may allow gene expression in a tissue-specific manner. The lysozyme promoter region of the present invention, therefore, will allow expression of an operably linked heterologous nucleic acid insert in a transfected avian cell such as, for example, an oviduct cell.

It is further contemplated that a recombinant DNA of the present invention may further comprise the chicken lysozyme 3' domain (SEQ. ID NO: 69) linked downstream of the nucleic acid insert encoding a heterologous polypeptide. The lysozyme 3' domain includes a nucleic acid sequence encoding a 3' MAR domain that may cooperate with a 5' MAR to direct the insertion of the construct of the present invention into the chromosome of a transgenic avian, or may act independently of the 5' MAR.

One aspect of the present invention, therefore, provides a novel isolated nucleic acid that comprises the nucleotide sequence of SEQ ID NO: 67, shown in FIG. 5 and derivatives and variants thereof, that is located immediately 5' upstream of the native lysozyme-encoding region of the chicken lysozyme gene locus.

In one embodiment of the novel isolated nucleic acid of the present invention, therefore, the avian nucleic acid sequence encoding a lysozyme gene expression control region comprises at least one 5' matrix attachment region, an intrinsically curved DNA region, at least one transcription enhancer element, a negative regulatory element, at least one hormone responsive element, at least one avian CR1 repeat element, and a proximal lysozyme promoter and signal peptide-encoding region. Interspersed between these constituent elements are stretches of nucleic acid that serve at least to organize the above elements in an ordered array relative to a polypeptide-encoding region, such as that encoding for chicken lysozyme. It is contemplated to be within the scope of the present invention that the cis-elements of the lysozyme gene expression control region may be in any linear arrangement that can allow the formation of a transcript comprising the nucleotide sequence or its complement of a nucleic insert operably linked to the lysozyme gene expression control region.

In one embodiment of the present invention, the isolated nucleic acid may be isolated from an avian selected from the group consisting of a chicken, a turkey, a duck, a goose, a quail, a pheasant, a ratite, an ornamental bird or a feral bird.

In another embodiment of the present invention, the isolated nucleic acid is obtained from a chicken. In this embodiment, the isolated nucleic acid has the sequence of SEQ ID NO: 67, as shown in FIG. 5, or a functional fragment thereof. A functional fragment refers to a portion of SEQ ID NO: 67 which can function as a promoter in vivo.

Another aspect of the present invention provides a novel isolated nucleic acid that comprises the nucleic acid of SEQ ID NO: 69 encoding the chicken 3' lysozyme domain operably liked to the nucleic acid having sequence of SEQ ID NO: 65.

One embodiment of the isolated nucleic acid of the present invention, therefore, is a lysozyme gene expression control region comprising the nucleic acid sequence of SEQ ID NO. 66 operably linked to a nucleic acid for expression in avian cells, and a chicken 3' lysozyme domain having the nucleic acid sequence of SEQ ID NO: 70, as shown in FIG. 8.

In another embodiment of the isolated nucleic acid of the present invention, the nucleic acid for expression in avian cells encodes a therapeutic protein. In one embodiment, the coding sequence for the therapeutic protein is optimized for expression in avian cells.

Another aspect of the invention provides nucleic acids that can hybridize under high, medium or low stringency conditions to an isolated nucleic acid that encodes a chicken lysozyme gene expression control region having all, a derivative of, or a portion of the nucleic acid sequence of SEQ ID NO: 67 shown in FIG. 5. The nucleotide sequence determined from the isolation of the lysozyme gene expression control region from a chicken (SEQ ID NO: 67) will allow for the generation of probes designed for use in identifying homologs of lysozyme gene expression control regions in other avian species.

Fragments of a nucleic acid encoding a portion of the subject lysozyme gene expression control region are also within the scope of the invention. As used herein, a fragment of the nucleic acid encoding an active portion of a lysozyme gene expression control region refers to a nucleotide sequence having fewer nucleotides than the nucleotide sequence encoding the entire nucleic acid sequence of the lysozyme gene expression control region.

In one embodiment of the present invention, the nucleotide sequence of the isolated DNA molecule of the present invention may be used as a probe in nucleic acid hybridization assays for the detection of the lysozyme gene expression control region. The nucleotide sequence of the present invention may be used in any nucleic acid hybridization assay system known in the art, including, but not limited to, Southern blots, Southern, E. M., 1975, J. Mol. Biol. 98: 508, Northern blots, Thomas et al., 1980, Proc. Natl. Acad. Sci. 77: 5201-05, and Colony blots, Grunstein et al., 1975, Proc. Natl. Acad. Sci. 72: 3961-65, the disclosures of which are incorporated herein by reference in their entireties. Alternatively, the isolated DNA molecules of the present invention can be used in a gene amplification detection procedure such as a polymerase chain reaction, Erlich et al., 1991, Science 252: 1643-51, the disclosure of which is incorporated herein by reference in its entirety, or in restriction fragment length polymorphism (RFLP) diagnostic techniques, as described in pgs. 519-522 and 545-547 of Watson et al., 2nd ed., 1992, "Recombinant DNA", Scientific American Books, the disclosure of which is incorporated herein by reference in its entirety.

Nucleotides constructed in accordance with the present invention can be labeled to provide a signal as a means of detection. For example, radioactive elements such as $^{32}P$, $^{3}H$, and $^{35}S$ or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals, such as Promega: Protocol and Applications Guide, 2nd Edition, 1991 Promega Corp., Madison, Wis., the disclosure of which is incorporated herein in its entirety, may be consulted to select an appropriate labeling protocol without undue experimentation.

In another embodiment of the present invention, an isolated nucleic acid molecule of the present invention includes a nucleic acid that is at least about 75%, and at least about 80%, and at least about 85%, and at least about 90%, and at least about 91%, and at least about 92%, and at least about 93%, and at least about 94%, and at least about 95%, and at least about 96%, and at least about 97%, and at least about 98%, and at least about 99%, identical to a chicken-derived lysozyme gene expression controlling region-encoding nucleic acid molecule as included in SEQ ID NO: 67.

In another embodiment of the present invention, an avian lysozyme gene expression control region gene or nucleic acid molecule can be an allelic variant of the gene expression controlling regions shown in SEQ ID NO: 67.

The present invention also contemplates the use of anti-sense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized nucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

The nucleic acid sequence of a chicken lysozyme gene expression control region nucleic acid molecule (e.g., included in SEQ ID NO: 67) of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain lysozyme gene expression control region nucleic acid homologs in other avian species such as, but not limited to, turkey, duck, goose, quail, pheasant, parrot, finch, ratites including ostrich, emu and cassowary and, (d) to obtain isolated nucleic acids capable of hybridizing to an avian lysozyme gene expression control region nucleic acid and be used to detect the presence of nucleic acid-related sequences by complementation between the probe and the target nucleic acid.

Such nucleic acid homologs can be obtained in a variety of ways including by screening appropriate expression libraries with antibodies of the present invention, using traditional cloning techniques to screen appropriate libraries, amplifying appropriate libraries or DNA using oligonucleotide primers of the present invention in a polymerase chain reaction or other amplification method, and screening public and/or private databases containing genetic sequences using nucleic acid molecules of the present invention to identify targets. Examples of preferred libraries to screen, or from which to amplify nucleic acid molecules, include but are not limited to mammalian BAC libraries, genomic DNA libraries, and cDNA libraries. Similarly, preferred sequence databases useful for screening to identify sequences in other species homologous to chicken lysozyme gene expression control region include, but are not limited to, GenBank and the mammalian Gene Index database of The Institute of Genomics Research (TIGR).

Codon-Optimized Proteins

Another aspect of the present invention is a recombinant DNA molecule comprising the novel isolated avian lysozyme gene expression control region of the present invention operably linked to a selected polypeptide-encoding nucleic acid insert, and which may express the nucleic acid insert when transfected to a suitable host cell, preferably an avian cell. The nucleic acid insert may be placed in frame with a signal peptide sequence, whereby translation initiation from the transcript may start with the signal peptide and continue through the nucleic acid insert, thereby producing an expressed polypeptide having the desired amino acid sequence.

It is anticipated that the recombinant DNA, therefore, may further comprise a polyadenylation signal sequence that will allow the transcript directed by the novel lysozyme gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like, or derivatives thereof.

In one embodiment of the recombinant DNA of the present invention, the polyadenylation signal sequence is derived from the SV40 virus.

In another embodiment of the recombinant DNA of the present invention, the polyadenylation signal has the nucleic acid sequence of SEQ ID NO: 68 or a variant thereof, as shown in FIG. 6.

It is further anticipated that the recombinant DNA of the present invention may further comprise the chicken lysozyme 3' domain SEQ ID NO: 69, or a variant thereof. The lysozyme 3' domain comprises a 3' untranslated region, a polyadenylation sequence and at least on 3' MAR.

Another aspect of the present invention is to provide nucleic acid sequences of a human interferon α2b protein optimized for expression in avian cells, and derivatives and fragments thereof.

In derivatives of proteins such as therapeutic proteins of the present invention, for example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, "Biochemistry", 2nd ed, L. Stryer, ed., W H Freeman and Co., 1981). Peptides in which more than one replacement has taken place can readily be tested in the same manner.

One embodiment of the present invention is a recombinant DNA molecule comprising the isolated avian lysozyme gene expression control region of the present invention, operably linked to a nucleic acid insert encoding a polypeptide, and a polyadenylation signal sequence optionally operably linked thereto. It is contemplated that when the recombinant DNA is to be delivered to a recipient cell for expression therein, the sequence of the nucleic acid sequence may be modified so that the codons are optimized for the codon usage of the recipient species. For example, if the recombinant DNA is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken.

In one embodiment of the recombinant DNA of the present invention, the nucleic acid insert encodes a therapeutic protein such as a human protein used as therapeutics wherein the sequence has been modified for codon optimization in an avian oviduct, e.g., a chicken oviduct. Optimization of the sequence for codon usage elevates the level of translation in avian eggs. As an example, the sequence (SEQ ID NO: 66) of the optimized human interferon alpha sequence is shown in FIG. 4.

In yet another embodiment of the present invention, the recombinant DNA comprises the isolated avian lysozyme gene expression control region operably linked to a nucleic acid encoding a therapeutic protein and a polyadenylation sequence, for example, the recombinant DNA having the nucleotide sequence of SEQ ID NO: 65, as shown in FIG. 3, or a variant thereof.

In still another embodiment of the present invention, the recombinant DNA comprises the isolated avian lysozyme gene expression control region operably linked to the nucleic acid encoding a polypeptide, and the chicken lysozyme 3' domain SEQ ID NO: 69. In one embodiment of the present invention, the nucleic acid insert is SEQ ID NO: 66 encoding a human α2b interferon, and the recombinant DNA construct has the nucleic acid sequence of SEQ ID NO: 70.

The protein of the present invention may be produced in purified form by any known conventional techniques. For example, chicken cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

Recombinant Nucleic Acids, and Expression Thereof Under the Control of an Avian Lysozyme Promoter:

Another potentially useful application of the novel isolated lysozyme gene expression control region of the present invention is the possibility of increasing the amount of a heterologous protein present in a bird, (especially the chicken) by gene transfer. In most instances, a heterologous polypeptide-encoding nucleic acid insert transferred into the recipient animal host will be operably linked with the lysozyme gene expression control region, to allow the cell to initiate and continue production of the protein product. A recombinant DNA molecule of the present invention can be transferred into the extra-chromosomal or genomic DNA of the host.

The recombinant DNA nucleic acid molecules of the present invention can be delivered to cells using conventional recombinant DNA technology. The recombinant DNA molecule may be inserted into a cell to which the recombinant DNA molecule is heterologous (i.e. not normally present). Alternatively, as described more fully below, the recombinant DNA molecule may be introduced into cells which normally contain the recombinant DNA molecule, for example, to correct a deficiency in the expression of a polypeptide, or where over-expression of the polypeptide is desired.

For expression in heterologous systems, the heterologous DNA molecule is inserted into the expression system or vector of the present invention in proper sense orientation and correct reading frame. The vector contains the necessary elements for the transcription and translation of the inserted protein-coding sequences, including the novel isolated lysozyme gene expression control region.

U.S. Pat. No. 4,237,224 to Cohen and Boyer, hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an expression vector suitable for delivery to a recipient cell for expression of the vector therein. It is contemplated to be within the scope of the present invention for the expression vector to comprise an isolated avian lysozyme gene expression control region operably linked to a nucleic acid insert encoding a polypeptide, and optionally a polyadenylation signal sequence. The expression vector of the present invention may further comprise a bacterial plasmid sequence, a viral nucleic acid sequence, or fragments or variants thereof that may allow for replication of the vector in a suitable host.

The novel isolated avian lysozyme gene expression control region of the present invention such as that included in SEQ ID NO: 67, and a polypeptide-encoding nucleic acid sequence operably linked thereto, such as, for example, SEQ ID NO: 66 or a derivative or truncated variant thereof, and optionally a polyadenylation signal sequence such as, for example, SEQ ID NO: 68 or the chicken lysozyme 3' domain may be introduced into viruses such as vaccinia virus. Methods for making a viral recombinant vector useful for expressing a protein under the control of the lysozyme promoter are analogous to the methods disclosed in U.S. Pat. Nos. 4,603, 112; 4,769,330; 5,174,993; 5,505,941; 5,338,683; 5,494,807; 4,722,848; Paoletti E., 1996, Proc. Natl. Acad. Sci., 93: 11349-11353; Moss, B., 1996, Proc. Natl. Acad. Sci. 93: 11341-11348; Roizman 1996, Proc. Natl. Acad. Sci. 93: 11307-11302; Frolov et al., 1996, Proc. Natl. Acad. Sci. 93: 11371-11377; Grunhaus et al., 1993, Seminars in Virology 3: 237-252 and U.S. Pat. Nos. 5,591,639; 5,589,466; and 5,580, 859 relating to DNA expression vectors, inter alia; the contents of which are incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference), pQE, pIH821, pGEX, pET series (see Studier, F. W. et. al., 1990, Use of T7 RNA Polymerase to Direct Expression of Cloned Genes in "Gene Expression Technology," vol. 185, which is hereby incorporated by reference in its entirety) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., 1982, Molecular Cloning: A Laboratory Manual, Cold Springs Laboratory, Cold Springs Harbor, N.Y., which is hereby incorporated by reference in its entirety.

A variety of host-vector systems may be utilized to express the protein-encoding sequence(s). Primarily, the vector system must be compatible with the host cell or host animal, such as an avian, that is used.

The use of eukaryotic recipient host cells permits partial or complete post-translational modification such as, but not only, glycosylation and/or the formation of the relevant inter- or intra-chain disulfide bonds. Host-vector systems include but are not limited to the following: bacteria transformed with bacteriophage DNA, plasmid DNA, or cosmid DNA; microorganisms such as yeast containing yeast vectors; vertebrate cell systems infected with virus (e.g., vaccinia virus, adenovirus, etc.); insect cell systems infected with virus (e.g., baculovirus) or avian embryonic cells inoculated with the recombinant nucleic acid. The expression elements of these vectors vary in their strength and specificities. Depending upon the host-vector system utilized, any one of a number of suitable transcription and translation elements can be used.

Once the novel isolated lysozyme gene expression control regions of the present invention have been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, microinjection and the like.

Another aspect of the present invention, therefore, is a method of expressing a heterologous polypeptide in a eukaryotic cell by transfecting the cell with a recombinant DNA comprising an avian lysozyme gene expression control region operably linked to a nucleic acid insert encoding a polypeptide and, optionally, a polyadenylation signal sequence, and culturing the transfected cell in a medium suitable for expression of the heterologous polypeptide under the control of the avian lysozyme gene expression control region.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken oviduct cell and the nucleic acid insert comprises the chicken lysozyme gene expression control region, a nucleic acid insert encoding a human protein and codon optimized for expression in an avian cell, and a polyadenylation sequence.

It is contemplated that transfected cells according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated for the scope of the present invention to include a transgenic animal producing a heterologous protein expressed from a transfected nucleic acid according to the present invention.

In one embodiment of the present invention, the transgenic animal is an avian selected from a turkey, duck, goose, quail, pheasant, ratite, an ornamental bird or a feral bird. In another embodiment, the avian is a chicken and the heterologous protein produced under the transcriptional control of the isolated avian lysozyme gene expression control region according to the present invention is produced in the white of an egg.

One particular aspect of the invention is directed to the use of retroviral constructs engineered to reduce or eliminate promoter interference. Promoter interference can be an undesired result that occurs when the function of a promoter interferes with the function of another promoter. In one embodiment, retroviral vectors designed to reduce or eliminate promoter interference can function by inactivation of the viral (e.g., LTR) promoter of a retroviral vector thereby functioning to reduce or eliminate LTR promoter interference of a promoter present in the vector which is operably linked to a coding sequence of interest. Such vectors are often referred to as self inactivating (i.e., SIN) vectors.

In another aspect, retroviral vectors can be engineered to reduce or eliminate promoter interference by removing from the vector, or not including in the vector in its initial construction, a selectable expression cassette, for example, which could be used for titering of the vector. Such vectors are referred to herein as SC negative vectors. SC negative vectors can still be titered, as is understood by a practitioner of skill in the art. However, such titering processes, which can involve determining relative cellular transfection frequency of the retroviral particles compared to that of standards of a known titer, are somewhat more difficult than titering using a selectable expression cassette. However, in some instances titering is not required for use of the retroviral vector to make a transgenic avian. In any case the lack of promoters of antibiotic resistance genes can eliminate the potential for promoter interference which can result from such promoters.

Self inactivating vectors and SC negative vectors are contemplated for use to reduce or eliminate promoter interference of any useful promoter which can be employed in transgenic avians such as chickens which produce exogenous proteins in the oviduct. For example, promoters which can preferentially express their gene product in oviduct cells or oviduct tissue are contemplated for use with SIN vectors and SC negative vectors. The invention contemplates the use of tissue specific promoters, constitutive promoters and inducible promoter for use with SIN vectors and SC negative vectors as disclosed herein. Examples of promoters which can be used with SIN vectors and SC negative vectors in accordance with the invention include but are not limited to, a cytomegalovirus (CMV) promoter, a rous-sarcoma virus (RSV) promoter, a β-actin promoter (e.g., a chicken β-actin promoter) a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter, and an ovotransferrin promoter. Optionally, the promoter may be a segment of at least one promoter region, such as a segment of the ovalbumin-, lysozyme-, conalbumin-, ovomucoid-, ovomucin-, and/or ovotransferrin promoter region. In one embodiment, the promoter is a combination or a fusion of one or more promoters or a fusion of a portion of one or more promoters such as ovalbumin-, lysozyme-, conalbumin-, ovomucoid-, ovomucin-, and ovotransferrin promoters with another promoter such as a viral promoter (e.g., an LTR promoter).

In one useful embodiment of the invention, a SIN vector is employed in a vector that is also an SC negative vector to produce a SIN/SC negative vector. The combination of SC negative vector and SIN vector can result in a vector with a substantially reduced amount of promoter interference compared to a vector that is only a SIN vector or only a SC negative vector.

Figure 13:
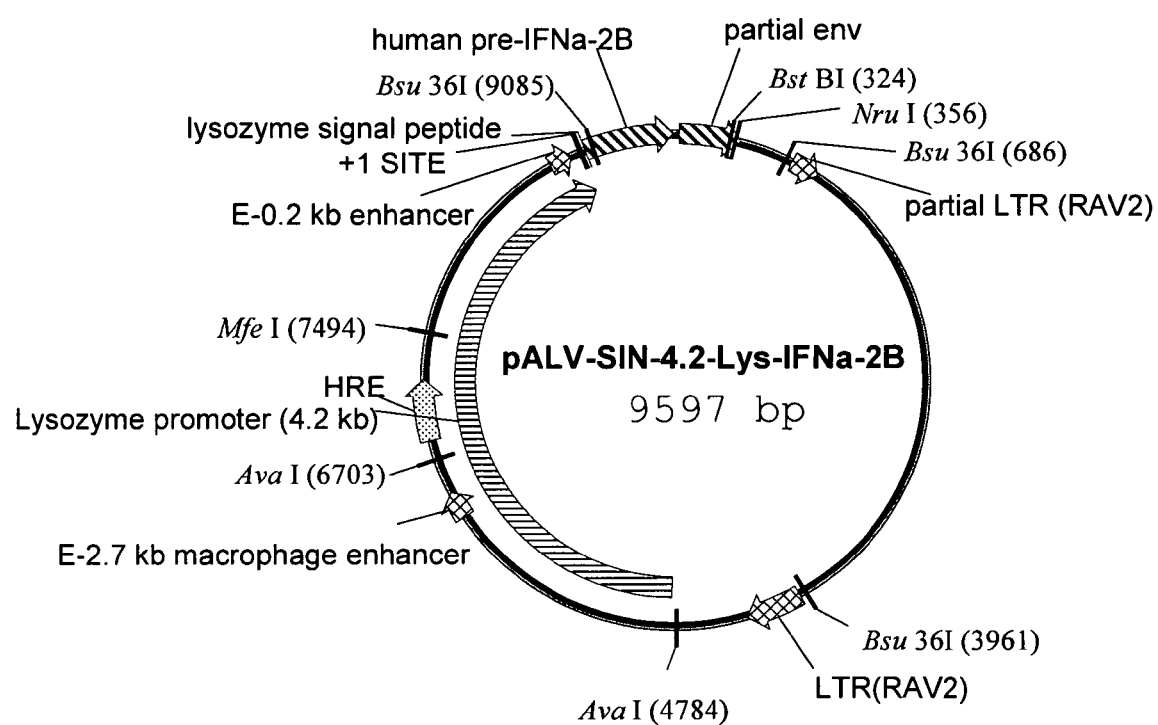
FIG. 13 illustrates a self-inactivating vector of the invention containing a 4.2 kb lysozyme promoter fragment operably linked to an interferon alpha 2 coding sequence and signal peptide coding sequence. The 5' long terminal repeat (LTR) of the vector is the complete LTR of an RSV virus. The 3' LTR has a deletion in the enhancer such that when the retroviral region integrates the 5' LTR is inactivated. The nucleotide sequence of the vector of FIG. 13 is shown in SEQ ID NO: 75.

In one useful embodiment, a SIN vector is produced in which a promoter that can inhibit transcription of a coding sequence operably linked to a lysozyme promoter of the invention (e.g., an LTR promoter) is inactivated, for example, by a deletion, insertion or transposition of all or part of the promoter sequence. In the case of the SIN/SC negative vector pALV-SIN-4.2-Lys-IFNa-2B, shown in FIG. 13, the 3' LTR has a deletion in the enhancer such that when the retroviral region integrates, the 5' LTR is inactivated. In addition, pALV-SIN-4.2-Lys-IFNa-2B also lacks an antibiotic resistance marker making it both a SC negative vector and a SIN vector. SIN vectors, SC vectors and SIN/SC negative vectors such as pALV-SIN-4.2-Lys-IFNa-2B are contemplated for application in any useful avian such as chicken, quail and turkey to produce chimeras including germ-line chimeras and progeny birds.

Viral Vector Cell Transformation:

An exemplary approach for the in vivo introduction of a nucleic acid encoding the subject novel isolated lysozyme gene expression control region into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo. These vectors provide efficient delivery of genes into cells, and the transferred nucleic acids are stably integrated into the chromosomal DNA of the host. In one embodiment, recombinant retrovirus vectors can be constructed in a part of the retroviral coding sequence (gag, pol, env) that has been replaced by nucleic acid encoding a lysozyme gene expression control region, thereby rendering the retrovirus replication defective. Protocols for producing recombinant retroviruses and for infecting cells in vitro or in vivo with such viruses can be found in Ausubel et al, 1989, "Current Protocols in Molecular Biology," Sections 9.10-9.14, Greene Publishing Associates, and other standard laboratory manuals. Examples of suitable retroviruses include, pLJ, pZIP, pWE and pEM, all of which are well known to those skilled in the art. Examples of suitable packaging virus lines for preparing both ecotropic and amphotropic retroviral systems include psiCrip, psiCre, psi2 and psiAm.

Avian retroviruses particularly useful in accordance with the present invention include, without limitation, Avian Leukemia/Leukosis Viruses (ALV), for example, and without limitation, RAV-0, RAV-1, RAV-2; Avian Sarcoma Viruses (ASV); Avian Sarcoma/Acute Leukemia Viruses (ASLV) including, without limitation, Rous Sarcoma Virus (RSV); Fujinami Sarcoma Viruses (FSV); Avian Myeloblastosis Viruses (AMV); Avian Erythroblastosis Viruses (AEV); Avian Myelocytomatosis Viruses (MCV), for example, and without limitation, MC29; Reticuloendotheliosis Viruses (REV), for example, and without limitation, Spleen Necrosis Virus (SNV). The invention also contemplates that the nucleotide sequence encoding a replication deficient retroviral vector can encode any useful retroviral vector, including, without limitation, retroviral vectors based upon Murine Leukemia Viruses (MLV); Molony Murine Sarcoma Viruses (MMSV); Moloney Murine Leukemia Viruses (MMLV); and lentiviruses (e.g., human immunodeficiency virus (HIV), feline immunodeficiency virus (FIV), bovine immunodeficiency virus (BIV) and simian immunodeficiency virus (SIV). In one particularly useful embodiment, the retroviral vector employed herein is vector based on one or more of these or other retroviruses.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include coupling antibodies specific for cell surface antigens to the viral env protein (Roux et al., 1989, Proc. Natl. Acad. Sci. 86: 9079-9083; Julan et al., 1992, J. Gen. Virol. 73: 3251-3255 and Goud et al., 1983, Virology 163: 251-254) or coupling cell surface ligands to the viral env proteins (Neda et al., 1991, J. Biol. Chem. 266: 14143-14146) (all of which are incorporated herein by reference in their entireties). Coupling can be in the form of the chemical cross-linking with a protein or other moiety (e.g., lactose to convert the env protein to an asialoglycoprotein), as well as by generating fusion proteins (e.g., single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., 1988, BioTechniques 6: 616; Rosenfeld et al., 1991, Science 252: 43 1434; and Rosenfeld et al., 1992, Cell 68: 143-155, all of which are incorporated herein by reference in their entireties). Suitable adenoviral vectors derived from the adenovirus strain Ad type 5 d1324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al., 1979, Cell 16:683; Berkner et al., supra; and Graham et al., 1991, pp. 109-127 in "Methods in Molecular Biology," vol. 7, E. J. Murray, ed., Humana, Clifton, N.J., all of which are incorporated herein by reference in their entireties). Expression of an inserted DNA segment such as, DNA encoding a therapeutic protein can be under control of the exogenously added lysozyme gene expression control region sequences.

Yet another viral vector system useful for delivery of, for example, the subject avian lysozyme gene expression control region operably linked to a nucleic acid encoding a polypeptide, is the adeno-associated virus (AAV). Vectors containing as little as 300 base pairs of AAV can be packaged and can integrate. Space for exogenous DNA is limited to about 4.5 kb. An AAV vector, such as that described in Tratschin et al., 1985, Mol. Cell. Biol. 5: 3251-3260, can be used to introduce DNA into cells. A variety of nucleic acids have been introduced into different cell types using AAV vectors (see, for example, Hermonat et al., 1984, Proc. Natl. Acad. Sci. 81: 6466-6470; Tratschin et al., 1985, Mol. Cell. Biol. 4: 2072-2081; Wondisford et al., 1988, Mol. Endocrinol. 2: 32-39; Tratschin et al., 1984, J. Virol. 51: 611-619; and Flotte et al., 1993, J. Biol. Chem. 268: 3781-3790, all of which are incorporated herein by reference in their entireties).

Non-Viral Expression Vectors:

Most non-viral methods of gene transfer can rely on normal mechanisms used by eukaryotic cells for the uptake and intracellular transport of macromolecules. In preferred embodiments, non-viral gene delivery systems of the present invention rely on endocytic pathways for the uptake of the subject lysozyme gene expression control region and operably linked polypeptide-encoding nucleic acid by the targeted cell. Exemplary gene delivery systems of this type include liposomal derived systems, poly-lysine conjugates, and artificial viral envelopes.

The invention provides for the use of non-viral methods of producing transgenic animals, such as transgenic avians, that contain nucleic acids of the invention (e.g., nucleic acids comprising a fragment of the lysozyme promoter operably linked to a nucleotide coding sequence). For example, the invention includes artificial chromosomes and integrase technologies for the production of transgenic avians. See, for example, U.S. patent application Ser. No. 11/362,064, filed Feb. 24, 2006, the disclosure of which is incorporated in its entirety herein by reference, and U.S. patent application Ser. No. 10/940,315, filed Sep. 14, 2004, now abandoned the disclosure of which is incorporated in its entirety herein by reference.

In a representative embodiment, a nucleic acid comprising the novel isolated lysozyme gene expression control region of the present invention can be entrapped in liposomes bearing positive charges on their surface (e.g., lipofectins) and (optionally) which are tagged with antibodies against cell surface antigens of the target tissue for cellular delivery (Mizuno et al., 1992, NO Shinkei Geka 20: 547-551; PCT publication WO91/06309; Japanese patent application 1047381; and European patent publication EP-A-43075, all of which are incorporated herein by reference in their entireties).

In similar fashion, the gene delivery system can comprise an antibody or cell surface ligand that is cross-linked with a gene binding agent such as polylysine (see, for example, PCT publications WO93/04701, WO92/22635, WO92/20316, WO92/19749, and WO92/06180, all of which are incorporated herein by reference in their entireties). It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., 1993, Science 260-926; Wagner et al., 1992, Proc. Natl. Acad. Sci. 89: 7934; and Christiano et al., 1993, Proc. Natl. Acad. Sci. 90: 2122, all of which are incorporated herein by reference in their entireties). It is further contemplated that a recombinant DNA molecule comprising the novel isolated lysozyme gene expression control region of the present invention may be delivered to a recipient host cell by other non-viral methods including by gene gun, microinjection, sperm-mediated transfer, or the like.

Transgenic Animals:

Another aspect of the present invention concerns transgenic animals, in particular avians such as chickens, having a transgene comprising the novel isolated lysozyme gene expression control region of the present invention and which preferably (though optionally) express a heterologous gene in one or more cells in the animal. Suitable methods for the generation of transgenic avians having heterologous DNA incorporated therein are described, for example, in WO 99/19472 to Ivarie et al.; WO 00/11151 to Ivarie et al.; and WO 00/56932 to Harvey et al., all of which are incorporated herein by reference in their entirety. Particularly useful methods of making transgenic avians, such as chickens which employ fragments of the avian lysozyme promoter of the invention are disclosed in U.S. patent application Ser. No. 11/167,052, filed Jun. 24, 2005, the disclosure of which is incorporated in its entirety herein by reference.

In certain embodiments of the present invention, the expression of the transgene may be restricted to specific subsets of cells, tissues or developmental stages utilizing, for example, cis-acting sequences acting on the lysozyme gene expression control region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences. The inclusion of a 5' MAR region in the novel isolated lysozyme gene expression control region of the present invention may allow the heterologous expression unit to escape the chromosomal positional effect (CPE) and therefore be expressed at a more uniform level in transgenic tissues that received the transgene by a route other than through germ line cells.

One embodiment of the present invention, therefore, is a transgenic avian having a heterologous polynucleotide sequence comprising a nucleic acid insert encoding the heterologous polypeptide and operably linked to the novel isolated avian lysozyme gene expression control region, the lysozyme gene expression control region comprising at least one 5' matrix attachment region, an intrinsically curved DNA region, at least one transcription enhancer, a negative regulatory element, at least one hormone responsive element, at least one avian CR1 repeat element, and a proximal lysozyme promoter and signal peptide-encoding region.

In an embodiment of the present invention, the transgenic avian is selected from a chicken, a turkey, a duck, a goose, a quail, a pheasant, a ratite, an ornamental bird or a feral bird.

In another embodiment of the present invention, the transgenic avian is a chicken.

In still another embodiment of the transgenic avian of the present invention, the transgenic avian includes an avian lysozyme gene expression control region comprising the nucleic acid sequence in SEQ ID NO: 67, or a variant thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In an embodiment of the transgenic avian of the present invention, the polyadenylation signal sequence comprises the nucleic acid sequence in SEQ ID NO: 68, or variant thereof.

In still another embodiment of transgenic avian of the present invention, the transgenic avian comprises the chicken lysozyme 3' domain having the nucleic acid sequence of SEQ ID NO: 69.

In another embodiment of the transgenic avian of the present invention, the nucleic acid insert encoding a polypeptide has a codon complement optimized for protein expression in an avian.

In yet another embodiment of the transgenic avian of the present invention, the nucleic acid insert encodes an interferon α.

In still another embodiment of the transgenic avian of the present invention, the nucleic acid insert encoding an interferon α2b polypeptide comprises the sequence in SEQ ID NO: 66, or a variant thereof.

In one embodiment of the transgenic avian of the present invention, the transgenic avian comprises the nucleotide sequence in SEQ ID NO: 65, or a variant thereof.

In yet another embodiment of the transgenic avian of the present invention, the transgenic avian comprises the nucleotide sequence in SEQ ID NO: 70, or a variant thereof. In another embodiment of the transgenic avian of the present invention, the transgenic avian produces the heterologous polypeptide in the serum or an egg white.

In another embodiment of the transgenic avian of the present invention, the transgenic avian produces the heterologous polypeptide in an egg white.

Therapeutic Proteins

The invention can be used to produce a wide range of desired therapeutic proteins such as fusion proteins, growth hormones, cytokines, structural proteins and enzymes including human growth hormone, interferon, lysozyme, and β-casein. Other possible proteins contemplated for production as disclosed herein include, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), somatotropin, and chymotrypsin. Modified immunoglobulins and antibodies, including immunotoxins which bind to surface antigens on human tumor cells and destroy them, can also be produced as disclosed herein.

Other specific examples of therapeutic proteins which may be produced as disclosed herein include, without limitation, factor VIII, b-domain deleted factor VIII, factor VIIa, factor IX, anticoagulants; hirudin, alteplase, tpa, reteplase, tpa, tpa—3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-alpha, inf-beta 1b, ifn-beta 1a, ifn-gamma1b, il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen ca125, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diphtheria toxin fusion protein, tnfr-lgg fragment fusion protein laronidase, dnaases, alefacept, darbepoetin alfa (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalamic releasing factors, antidiuretic hormones, prolactin and thyroid stimulating hormone.

The invention, includes methods for producing multimeric proteins including immunoglobulins, such as antibodies, and antigen binding fragments thereof. Thus, in one embodiment of the present invention, the multimeric protein is an immunoglobulin, wherein the first and second heterologous polypeptides are immunoglobulin heavy and light chains respectively.

In certain embodiments, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by an expression vector may also be an immunoglobulin light chain polypeptide comprising a variable region or a variant thereof, and may further comprise a J region and a C region. The present invention also contemplates multiple immunoglobulin regions that are derived from the same animal species, or a mixture of species including, but not only, human, mouse, rat, rabbit and chicken. In certain embodiments, the antibodies are human or humanized.

In other embodiments, the immunoglobulin polypeptide encoded by at least one expression vector comprises an immunoglobulin heavy chain variable region, an immunoglobulin light chain variable region, and a linker peptide thereby forming a single-chain antibody capable of selectively binding an antigen.

Examples of therapeutic antibodies that may be produced in methods of the invention include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-α antibody (CATI-BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152, a human anti-TGF-β$_2$ antibody (Cambridge Ab Tech).

The present invention is further illustrated by the following examples, which are provided by way of illustration and should not be construed as limiting. The contents of all references, published patents and patents cited throughout the present application are hereby incorporated by reference in their entireties.

EXAMPLE 1

Construction of Lysozyme Promoter Plasmids

The chicken lysozyme gene expression control region was isolated by PCR amplification. Ligation and reamplification of the fragments thereby obtained yielded a contiguous nucleic acid construct comprising the chicken lysozyme gene expression control region operably linked to a nucleic acid sequence optimized for codon usage in the chicken (SEQ ID NO: 66) and encoding a human interferon α2b polypeptide optimized for expression in an avian cell.

White Leghorn Chicken (*Gallus gallus*) genomic DNA was PCR amplified using the primers 5pLMAR2 (SEQ ID NO: 1) (see FIG. 1) and LE-6.1 kbrev1 (SEQ ID NO: 2) in a first reaction, and Lys-6.1 (SEQ ID NO: 3) and LysE1rev (SEQ ID NO: 4) as primers in a second reaction. PCR cycling steps were: denaturation at 94° C. for 1 minute; annealing at 60° C. for 1 minute; extension at 72° C. for 6 minutes, for 30 cycles using TAQ PLUS PRECISION™ DNA polymerase (Stratagene, La Jolla, Calif.). The PCR products from these two reactions were gel purified, and then united in a third PCR reaction using only 5pLMAR2 (SEQ ID NO: 1) and LysE1rev (SEQ ID NO: 4) as primers and a 10-minute extension period. The resulting DNA product was phosphorylated, gel-purified, and cloned into the EcoR V restriction site of the vector pBluescript KS, resulting in the plasmid p12.0-lys.

p12.0-lys was used as a template in a PCR reaction with primers 5pLMAR2 (SEQ ID NO: 1) and LYSBSU (SEQ ID NO: 5) and a 10 minute extension time. The resulting DNA was phosphorylated, gel-purified, and cloned into the EcoR V restriction site of pBluescript KS, forming plasmid p12.0lys-B.

p12.0lys-B was restriction digested with Not I and Bsu36 I, gel-purified, and cloned into Not I and Bsu36 I digested pCMV-LysSPIFNMM, resulting in p12.0-lys-LSPIFNMM. p12.0-lys-LSPIFNMM was digested with Sal I and the SalI to NotI primer (SEQ ID NO: 6) was annealed to the digested plasmid, followed by Not I digestion. The resulting 12.5 kb Not I fragment, comprising the lysozyme promoter region linked to IFNMAGMAX-encoding region and an SV40 polyadenylation signal sequence, was gel-purified and ligated to Not I cleaved and dephosphorylated pBluescript KS, thereby forming the plasmid pAVIJCR-A 115.93.1.2. The lysozyme promoter/IFN construct contained in plasmid pAVIJCR-A115.93.1.2 was sequenced as described in Example 3.

EXAMPLE 2

Construction of Plasmids which Contain the 3' Lysozyme Domain

The plasmid pAVIJCR-A 115.93.1.2 was restriction digested with FseI and blunt-ended with T4 DNA polymerase. The linearized, blunt-ended pAVIJCR-A115.93.1.2 plasmid was then digested with XhoI restriction enzyme, followed by treatment with alkaline phosphatase. The resulting 15.4 kb DNA band containing the lysozyme 5' matrix attachment region (MAR) and –12.0 kb lysozyme promoter driving expression of a human interferon was gel purified by electroelution.

The plasmid pIIIilys was restriction digested with MluI, then blunt-ended with the Klenow fragment of DNA polymerase. The linearized, blunt-ended pIIIilys plasmid was digested with XhoI restriction enzyme and the resulting 6 kb band containing the 3' lysozyme domain from exon 3 to the 3' end of the 3' MAR was gel purified by electroelution. The 15.4 kb band from pAVIJCR-A115.93.1.2 and the 6 kb band from pIIIilys were ligated with T4 DNA ligase and transformed into STBL4 cells (Invitrogen Life Technologies, Carlsbad, Calif.) by electroporation. The resulting 21.3 kb plasmids from two different bacterial colonies were named pAVIJCR-A212.89.2.1 and pAVIJCR-A212.89.2.3 respectively.

EXAMPLE 3

Sequencing Reactions

Plasmid DNA (pAVIJCR-A115.93.1.2) produced as described in Example 1 was purified with QIAGEN™ columns (Qiagen, Valencia, Calif.). Sequencing reactions were performed according to the Applied Biosystems (Foster City, Calif.) protocol for BIGDYE™ Terminators, version 2.0, using an ABI 373 Stretch sequencer. Sequencing primers used are listed in FIG. 1, and a schematic diagram illustrating the sequencing reactions using the different primers is shown in FIG. 2. Sequence data was analyzed with SEQUENCHER™ software, version 4.0 (Gene Codes Corp., Ann Arbor, Mich.).

EXAMPLE 4

Complete Lysozyme Promoter and IFNMAGMAX Sequences

The complete nucleotide sequence (SEQ ID NO: 65), shown in FIG. 3, of the 12.5 kb chicken lysozyme promoter region/IFNMAGMAX construct spans the 5' matrix attachment region (5' MAR), through the lysozyme signal peptide, to the sequence encoding the gene IFNMAGMAX and the subsequent polyadenylation signal sequence. The IFNMAGMAX nucleic acid sequence (SEQ ID NO: 66), shown in FIG. 4, encoded human interferon α2b (IFN) that had been synthesized based on a codon usage table compiled from the four most abundantly expressed hen egg white proteins ovalbumen, ovotransferrin, ovomucoid and lysozyme. The expressed IFN α2b sequence within plasmid pAVIJCR-A1 15.93.1.2 functioned as a reporter gene for lysozyme promoter activity. This plasmid construct may also be used for production of interferon α2b in the egg white of transgenic chickens. The isolated sequence of the 11.94 kb chicken lysozyme promoter region (SEQ ID NO: 67) alone is shown in FIG. 5. The sequence of the SV40 polyadenylation signal sequence (SEQ ID NO: 68) is shown in FIG. 6.

EXAMPLE 5

Basic Local Alignment Search Tool (BLAST) Analysis of the Complete Lysozyme Promoter Sequence (SEQ ID NO: 65)

The complete 12.5 kb lysozyme promoter/IFNMAGMAX sequence (SEQ ID NO: 65) was submitted to the National Center for Biotechnology Information for BLAST alignments with database sequences. Percent identities between the lysozyme promoter sequence (SEQ ID NO: 67, included within SEQ ID NO: 65) and corresponding known lysozyme promoter features are shown in Table II below:

TABLE II

| BLAST Results of the Complete 12.0 kb Lysozyme Promoter Sequence | | | |
|---|---|---|---|
| Description of DNA element | Coordinates in this sequence | GenBank accession number | % identity |
| 5' matrix attachment region | 1-237, 261-1564 | AJ277960 | 96 |
| 5' matrix attachment region | 1-237, 261-1564 | X98408 | 96 |
| 5' matrix attachment region | 1564-1912 1930-2015 | X84223 | 99 |
| Intrinsically curved DNA | 2011-2671 | X52989 | 98 |
| Transcription enhancer (−6.1 kb) | 5848-5934 | Grewal et al., 1992 | 100 |
| Transcription enhancer (E-2.7 kb) | 9160-9329 | X05461 | 98 |
| Negative regulatory element | 9325-9626 | X05463 | 98 |
| Hormone response element | 9621-9666 9680-10060 | X12509 | 99 |

TABLE II-continued

| BLAST Results of the Complete 12.0 kb Lysozyme Promoter Sequence | | | |
|---|---|---|---|
| Description of DNA element | Coordinates in this sequence | GenBank accession number | % identity |
| CR1 chicken repeat element | 10576-10821, 10926-11193 | U88211, K02907 | 87 |
| Transcription enhancer (E-0.2 kb) | 11655-11797 | X05462 | 100 |
| Proximal promoter and lysozyme signal peptide | 11563-11877 | M12532 | 100 |
| Proximal promoter and lysozyme signal peptide | 11424-11938 | J00886 | 99 |

Features that have been previously identified as individual elements isolated from other component elements of the lysozyme promoter region include the 5' MAR, three transcription enhancers, a hormone-responsive element, and a chicken repeat 1 (CR1) element. The IFNMAGMAX sequence (SEQ ID NO: 66) extended from nucleotide positions 11946 to 12443 of SEQ ID NO: 65, shown in FIG. 3.

EXAMPLE 6

Expression in Transfected Cultured Avian Oviduct Cells of Human Interferon α2b Regulated by the 12 kb Lysozyme Promoter The oviduct was removed from a Japanese quail (*Coturnix coturnix japonica*) and the magnum portion minced and enzymatically dissociated with 0.8 mg/ml collagenase (Sigma Chemical Co., St. Louis, Mo.) and 1.0 mg/ml dispase (Roche Molecular Biochemicals, Indianapolis, Ind.) by shaking and titurating for 30 minutes at 37° C. The cell suspension was then filtered through sterile surgical gauze, washed three times with F-12 medium (Life Technologies, Grand Island, N.Y.) by centrifugation at 200×g, and resuspended in OPTI-MEM™ (Life Technologies) such that the $OD_{600}$ was approximately 2. Cell suspension (300 µl) was plated per well of a 24-well dish. For each transfection, 2.5 µl of DMRIE-C liposomes (Life Technologies) and 1 µg of DNA were preincubated for 15 minutes at room temperature in 100 µl of OPTIMEM™, and then added to the oviduct cells. Cells with DNA/liposomes were incubated for 5 hours at 37° C. in 5% $CO_2$. Next, 0.75 ml of DMEM (Life Technologies) supplemented with 15% fetal bovine serum (FBS) (Atlanta Biologicals, Atlanta, Ga.), 2× penicillin/streptomycin (Life Technologies), $10^{-6}$ M insulin (Sigma), $10^{-8}$ M β-estradiol (Sigma), and $10^{-7}$ M corticosterone (Sigma) was added to each well, and incubation was continued for 72 hours. Medium was then harvested and centrifuged at 110×g for 5 minutes. The supernatant was analyzed by ELISA for human interferon α2b content.

The human interferon α2b contents of medium derived from cultured oviduct cells transfected with either the −12.0 kb IFN plasmid (pAVIJCR-A115.93.1.2) or the negative control plasmid pCMV-EGFP as shown in FIG. 7. Bars to the right of the figure represent the standards for the IFN ELISA.

EXAMPLE 7

Transfection of Chicken HD11 Cells with pAVIJCR-A212.89.2.1 and pAVIJCR-A212.89.2.3

Chicken cells transfected with plasmids having the 3' lysozyme domain linked to a nucleic acid expressing human α2b interferon express the heterologous polypeptide. Chicken myelomonocytic HD11 cells were transfected with plasmid pAVIJCR-A212.89.2.1 and pAVIJCR-A212.89.2.3 to test the functionality of the plasmids. One million HD11 cells were plated per each well of a 24-well dish. The next day, HD11 cells were transfected with 1 μg of plasmid DNA per 4 μl of LipofectAMINE 2000 (Invitrogen Life Technologies). For comparison, independent wells were also transfected with the parent vector pAVIJCR-A 115.93.1.2. After 5 hours of transfection, the cell medium was changed with fresh medium. 48 hours later, cell medium was harvested by centrifugation at 110×g for 5 min and assayed for human interferon by ELISA (PBL Biomedicals, Flanders, N.J.).

Figure 10:
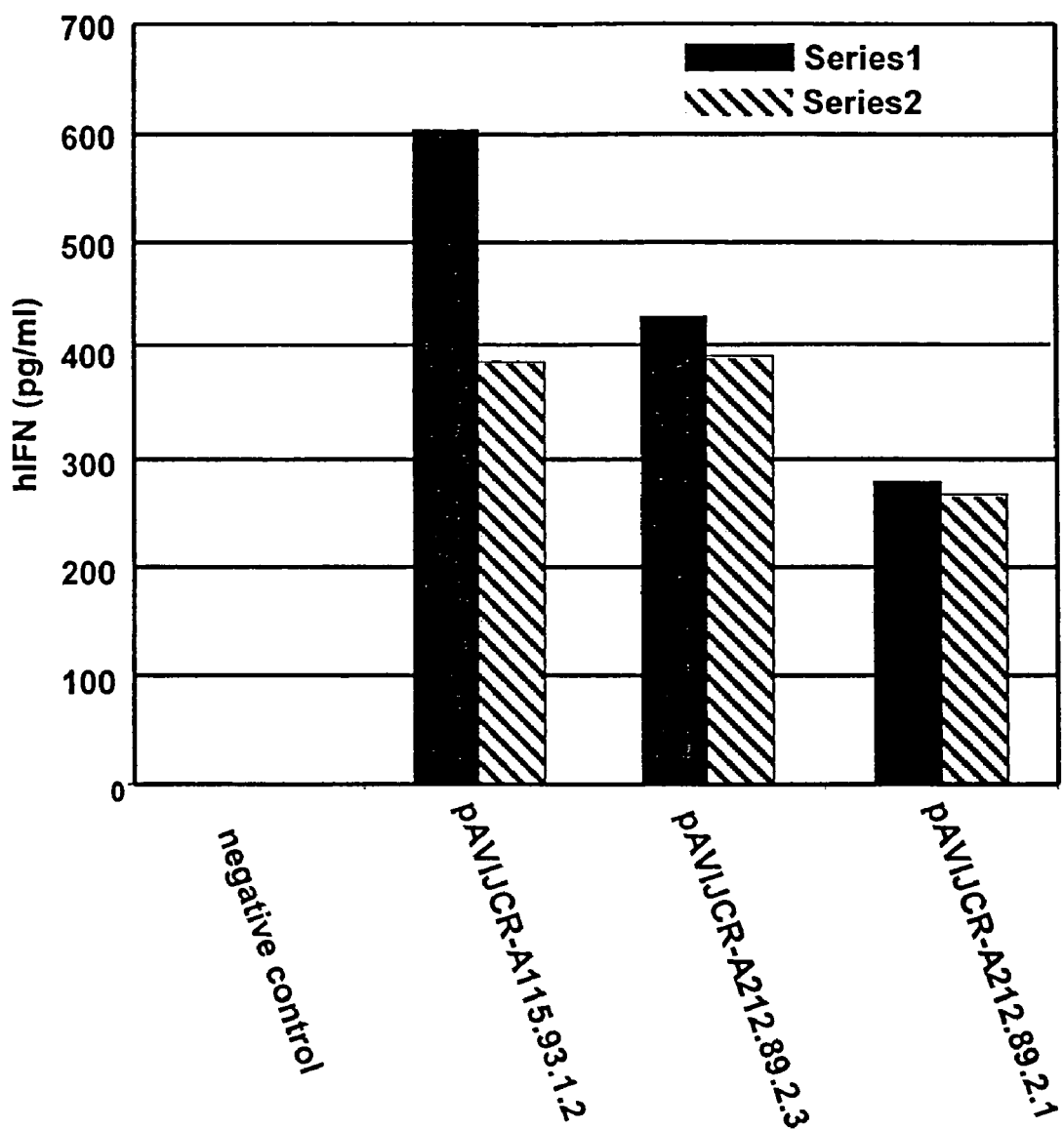
FIG. 10 illustrates the yield of the human interferon α2b, optimized for chicken expression (IFNMAGMAX), in chicken myelomonocytic HD 11 cells transfected with plasmids pAVIJCR-A115.93.1.2, pAVIJC-A212.89.2.3 or pAVIJCR-A212.89.2.1.

The transfected cells expressed the heterologous human α2b interferon at least to the level seen with a plasmid not having the 3' lysozyme domain operably linked to the human α2b interferon encoding nucleic acid, as shown in FIG. 10.

EXAMPLE 8

Expression of Human α2b Interferon in a Transgenic Avian Platform

The plasmid pAVIJCR-A115.93.1.2 (containing the −12.0 kb lysozyme promoter controlling expression of human interferon α-2b) was purified with a Qiagen Plasmid Maxi Kit (Qiagen, Valencia, Calif.), and 100 micrograms of the plasmid were restriction digested with NotI restriction enzyme. The digested DNA was phenol/CHCl$_3$ extracted and ethanol precipitated. Recovered DNA was resuspended in 1 mM Tris-HCl (pH 8.0) and 0.1 mM EDTA, then placed overnight at 4° C. DNA was quantified by spectrophotometry and diluted to the appropriate concentration. DNA samples were resuspended in 0.25 M KCl and bound with a SV40 T antigen nuclear localization signal peptide (NLS peptide, amino acid sequence CGGPKKKRKVG-NH$_2$; SEQ ID NO: 71) by adding the NLS at a peptide:DNA molar ratio of 100:1 (Collas and Alestrom, 1996, Mol. Reprod. Develop. 45: 431-438; the contents of which is incorporated by reference in its entirety).

Cytoplasmic Microinjection of DNA. Approximately two nanoliters of DNA were injected into the germinal disk of stage I White Leghorn embryos obtained two hours after oviposition of the previous egg. DNA amounts per injection ranged from 10 picograms to 400 picograms. Injected embryos were surgically transferred to recipient hens via ovum transfer according to the method of Christmann et al (PCT/US01/26723 to Christmann et al; the contents of which is hereby incorporated by reference in its entirety)

Analysis of chick blood DNA by PCR for IFN transgene: Whole blood from one week old chicks was collected with heparinized capillary tubes. Red blood cell (RBC) nuclei were released and washed with lysis buffer solution. DNA's from RBC nuclei were extracted by digestion with proteinase K (1 mg/ml) and precipitated with ethanol. Purified DNA was resuspended in 1 mM Tris-HCl (pH 8.0) and 0.1 mM EDTA and quantitated. Genomic DNA samples were analyzed by PCR using primers LYS051 (SEQ ID NO.: 72) for 5'-TG-CATCCTTCAGCACTTGAG-3' and IFN-3 (SEQ ID NO: 73) for 5'-AACTCCTCTTGAGGAAAGCC-3'. This primer set amplifies a 584 bp region of the transgene carried by the pAVIJCR-A115.93.1.2 plasmid. Three hundred nanograms of genomic DNA were added to a 50 μl reaction mixture (1× Promega PCR Buffer with 1.5 mM MgCl$_2$, 200 μM of each dNTP, 5 μM primers) and 1.25 units of Taq DNA polymerase (Promega). The reaction mixtures were heated for 4 minutes at 94° C. and then amplified for 34 cycles at 94° C. for 1 min, 60° C. for 1 min and 72° C. for 1 min. The samples were heated in a final cycle for 4 minutes at 72° C. PCR products were detected on a 0.8% agarose gel with ethidium bromide staining.

Human interferon α-2b expression in chick blood by ELISA: One week after hatch, blood was collected from chicks using heparinized capillary tubes; added to an equal volume of phosphate buffered saline and centrifuged at 200×g. 100 microliters of the supernatant were assayed by human IFN ELISA (PBL Biomedical Laboratories, New Brunswick, N.J.).

Human interferon α-2b expression in egg white of transgenic hens: once hens reached sexual maturity and began to lay (approximately 22-24 weeks of age), eggs were collected and egg white assayed by ELISA using human IFN ELISA (PBL Biomedical Laboratories, New Brunswick, N.J.) according to maufacturer's instructions.

Results of PCR and ELISA analysis of blood and egg white: Table III below summarizes results of PCR and ELISA analysis.

TABLE III

Analysis of Transgene presence and Interferon Expression

| Bird # | Method | PCR (Blood) | ELISA (Blood) | ELISA (egg white) | # Birds Tested |
|---|---|---|---|---|---|
| 8305 | −NLS | + | + | NA (male) | |
| 8340 | −NLS | − | − | + | 69 (2.5%) |
| AA123 | +NLS | + | + | NA (immature) | |
| AA61 | +NLS | + | + | NA (immature) | |
| AA105 | +NLS | − | + | NA (immature) | |
| AA115 | +NLS | + | − | NA (immature) | 43 (9%) |

Figure 11:
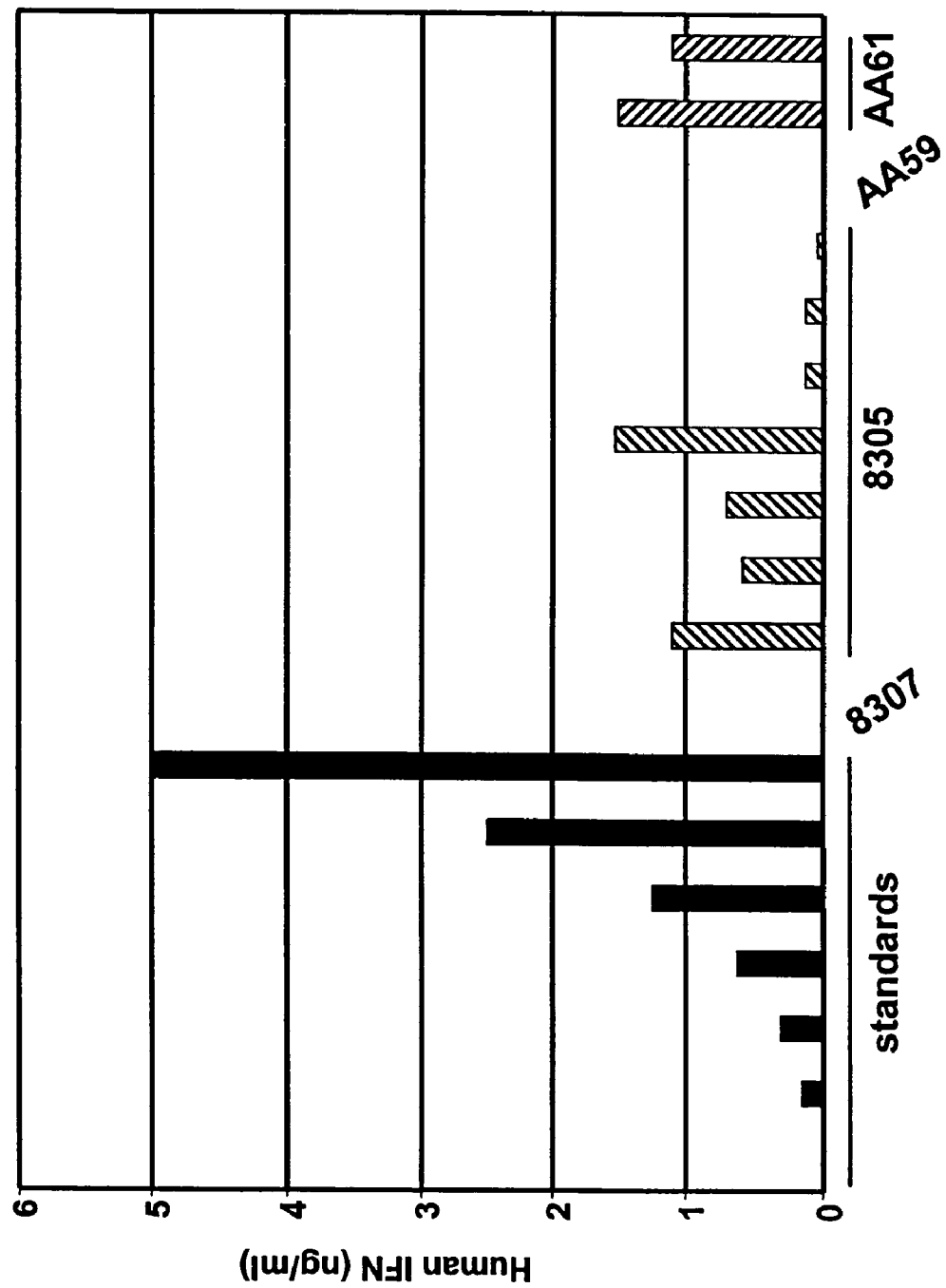
FIG. 11 illustrates the expression of α2b human interferon in the blood of transgenic chickens #8305 and #AA61, as compared to standards.
Figure 12:
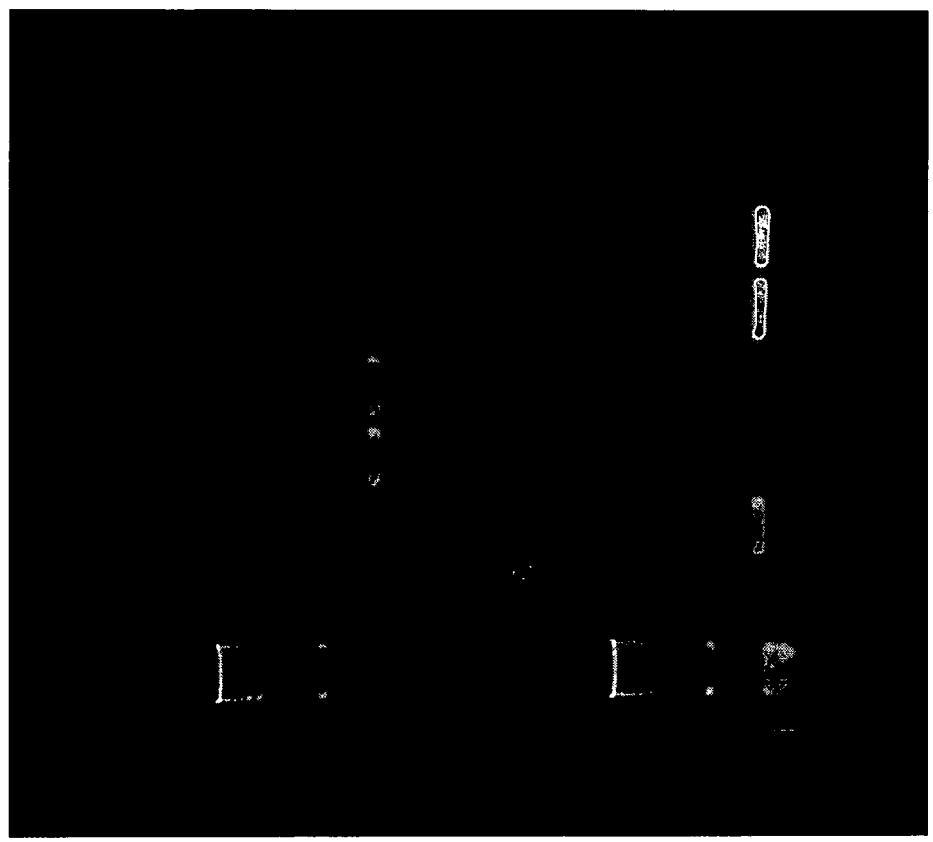
FIG. 12 illustrates the gel analysis of PCR products derived from the serum of transgenic birds. Lane and Samples applied to the gel were: 1, marker; 2, 8301; 3, 8303; 4, 8305 5, 8305; 6, 8307; 7, 8309; 8, 8311; 9, marker; 10, 8313; 11, 8305; 12, 8305; 13, Neg. Ctrl; 14, Pos. Ctrl (500 pg)+Neg. Ctrl; 15, Pos. Ctrl (500 pg).

−NLS: DNA injected without NLS peptide;
+NLS: DNA injected with NLS peptide;
NA: not applicable As shown in Table III, one bird (#8305) of 69 produced using microinjection of DNA without the NLS peptide, was positive for both presence of the transgene and expression of interferon in the blood. Because this bird is a male, he will be bred to a non-transgenic hen to examine germline transmission of the transgene. FIG. 11 demonstrates expression of human interferon in the blood of #8305, as compared to standards. FIG. 12 illustrates PCR results from the serum for several birds, including #8305, obtained at different intervals after hatch. As can be seen in lanes 4, 5, 11, and 12, positive signal was seen indicating the presence of the transgene at two different collection periods.

Other positives were seen in birds produced under microinjection of DNA covalently linked to the NLS peptide as described above. Table III illustrates 4 birds (AA123, AA61, AA105 and AA115) out of 43 tested that were PCR positive, ELISA positive or both. Expression levels of human IFN in AA61, as compared to standards, is also illustrated in FIG. 11. Males will be bred to determine germline transmission, and eggs collected from transgenic females to assay for IFN expression, as described above, as chicks reach sexual maturity.

EXAMPLE 9

Expression of a Human Monoclonal Antibody (Mab) in a Transgenic Avian Platform

Transgenic chickens were produced as described in Example 8 above, except that two distinct constructs were coinjected into Stage 1 embryos. The constructs comprised the 12 kb lysozyme promoter, as described above in Example 4, driving either a heavy chain or light chain of a human monoclonal antibody against CTLA-4 (WO 01/14424 A2 to Korman et al.; the contents of which is incorporated herein in its entirety). ELISA analysis of serum, conducted as described above in Example 8, is summarized below:

TABLE IV

ELISA analysis of Mab expression in hatched birds:

| Bird # | Method | ELISA (serum) | ELISA (egg white) | # Birds Tested |
|---|---|---|---|---|
| 214 | +NLS | + | NA (immature) | |
| 228 | +NLS | + | " | 13 |

+NLS: DNA injected with NLS peptide;
NA: not available

Results indicate that two birds of the thirteen tested to date, #214 and #228, are positive for Mab expression in the serum.

EXAMPLE 10

Production of Transgenic Quail Containing pALV-SIN-4.2-Lys-IFNa-2B in their Genome The vector pALV-SIN-4.2-Lys-IFNa-2B (shown in FIG. 13) was constructed and used to produce transgenic Quail. The sequence of pALV-SIN-4.2-Lys-IFNa-2B is shown in SEQ ID NO: 75. The 4.2 Kb lysozyme promoter spans from nucleotides 4810 to 9008 of SEQ ID NO: 75. The lysozyme signal peptide coding sequence spans from nucleotides 9037 to 9090 of SEQ ID NO: 75. The interferon alpha 2b coding sequence spans from nucleotides 9091 to 9585 of SEQ ID NO: 75. Other components of the sequence include LTRs spanning from nucleotides 4000 to 4345 and from nucleotides 725 to 897.

pALV-SIN-4.2-Lys-IFNa-2B can be constructed by a variety of methods which are apparent to a practitioner of skill in the art. However, the method believed to be the best for making the vector is as follows: A 3427 bp region of pNLB-CMV-IFN-alpha2B (disclosed in U.S. patent application Ser. No. 11/167,052, filed Jun. 24, 2005, the disclosure of which is incorporated in its entirety herein by reference) is PCR amplified using primers ATGCGCGCATTGGTAATTGATCG-GCTGG (Primer ALV-SIN-1, SEQ ID NO: 76) and ATAT-GCGGCCGCGGTACCGCCCGGGCATCGATATCAAGC-TTACGGTTCACTA AACGAGCTCTGCTTATATAGAC-CTCCCA (Primer ALV-SIN-2, SEQ ID NO: 77). The product is digested with BssHII and Not I resulting in a 3428 bp fragment which can be isolated by gel purification. A 1436 bp region of pNLB-CMV-IFN-alpha2B is PCR amplified with primers ATATGCGGCCGCGTCGACGGCCGGCCA-GATCTGCTGAGCCGGTCGCTACCAT TACCAGT (Primer ALV-SIN-3, SEQ ID NO: 78) and ATACGCGTAT-TCCCTAACGATCACGTCG (Primer ALV-SIN-4, SEQ ID NO: 79). The resulting product is digested with Not I and Mlu I yielding a 1438 bp fragment which is isolated by gel purification. A Bluescript II SK vector containing a BssHII stuffer fragment is digested with BssHII resulting in a linearized Bluescript vector of 2788 bp which is gel purified and then ligated to the 3428 bp and 1438 bp PCR products to yield JCR.A108.49.5.24.

JCR.A108.49.5.24 is digested with Hind III and the resulting 6823 bp fragment is circularized by ligation to yield JCR.A108.76.1.1.

A 1175 bp region of JCR.A108.76.1.1 is PCR amplified with primers CTGAAGTGTAAGGAATGTAAG (Primer ALV-SIN-5, SEQ ID NO: 80) and GCGCGTCTCATC-CCCCTCCCTATGCAAAAG (Primer ALV-SIN-6, SEQ ID NO: 81) and the resulting fragment is digested with Blp I and Esp3I producing a 1030 bp fragment which is isolated by gel purification. A 660 bp region of JCR.A108.76.1.1 is PCR amplified with primers GGGCGTCTCAGGGACGGATTG-GACGAACCACTGAATT (Primer ALV-SIN-7, SEQ ID NO: 82) and TTAGTGCTTTACGGCACCTC (Primer ALV-SIN-8, SEQ ID NO: 83) and digested with Esp3I and DraIII resulting in a 596 bp fragment which is isolated by gel purification. JCR.A108.76.1.1 is digested with DraIII and Blp I and the 5024 bp linear vector is ligated to the 1030 and 596 bp PCR fragments to produce pALV-SIN.

pALV-SIN is digested with BamHI and the 4795 bp linear vector is isolated by gel purification. A 4815 bp region of JCR.115.93.1.2 is PCR amplified with primers GACG-GATCCGATACCGTCCCTATTTTTGTGTTTGCTTC (Primer ALV-SIN-9, SEQ ID NO: 84) and TAACGGATC-CTAGACTTTTTACTCCTTAGA (Primer ALV-SIN-10, SEQ ID NO: 85) and is digested with BamHI. The resulting 4802 fragment is ligated to the 4795 bp linear pALV-SIN to create pALV-SIN-4.0-Lys-IFNa-2B.

Transduction particles of the vector pALV-SIN-4.2-Lys-IFNa-2B were produced in fibroblast cells as disclosed in U.S. patent application Ser. No. 11/542,093, filed Oct. 3, 2006 titled: Rapid Production of High Titer Virus, the disclosure of which is incorporated in its entirety herein by reference.

Fertilized Japanese quail eggs were windowed essentially according to the Speksnijder procedure (U.S. Pat. No. 5,897,998, the disclosure of which is incorporated in its entirety herein by reference) 80 eggs were injected in the subgerminal cavity with about $7 \times 10^4$ pALV-SIN-4.2-Lys-IFNa-2B transducing particles per egg of which 16 chicks hatched. Eggs hatched 18 days after injection and human IFN levels were measured by IFN ELISA from serum samples collected from chicks 12 weeks after hatch. None were positive for the IFN protein in the serum.

In order to identify G0 quail which contained the interferon alpha 2 coding sequence containing transgene in their genome, DNA was extracted from blood of the birds and the DNA samples were subjected to Taqman® analysis on a 7700 Sequence Detector (Perkin Elmer). Quail No. 4 was positive for the transgene.

Figure 14:
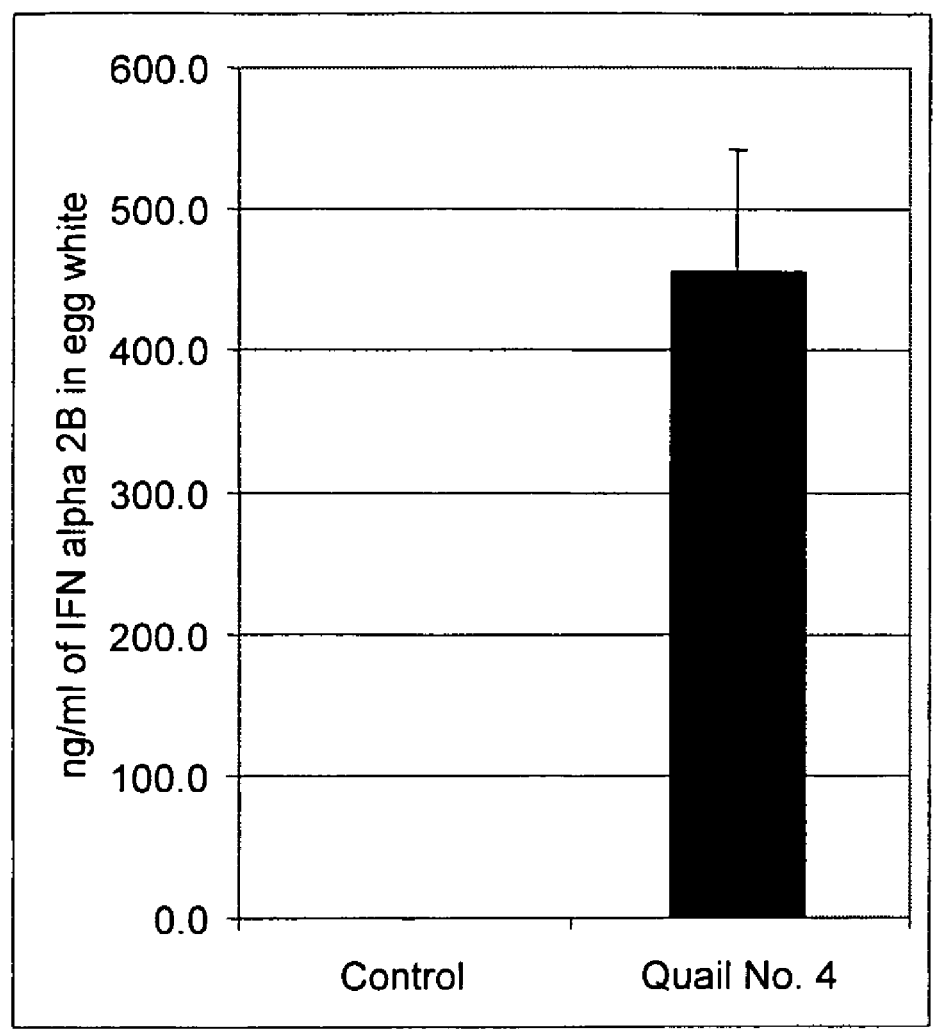
FIG. 14 is a bar graph illustrating expression levels of IFNa in the egg white of a transgenic quail. G0 quail was produced by injection of pALV-SIN-4.0-Lys-IFNa-2B retroviral vector transduction particles into Japanese quail embryos.

Eggs from eight G0 quail were tested for the presence of the IFN protein in the egg white by ELISA. Quail No. 4 was found to have significant levels of IFN in egg white from her eggs. FIG. 14 shows a bar graph illustrating expression levels of IFN in the egg white of Quail No. 4. Quail No. 4 expressed IFN-alpha-2 at 0.45 micrograms per ml of egg white, which is a high level of expression for a G0 avian. There was no interferon alpha 2 detected in the blood of Quail No. 4. This is particularly significant since the lack of circulating recombinant protein can facilitate recombinant protein production.

This is because, for example, in certain instances the recombinant (exogenous) protein may be harmful to the development or health of the avian when present in the blood.

EXAMPLE 11

Production of Transgenic Avians Containing pALV-SIN-6.5-Lys-IFNa-2B

The 4.2 kb lysozyme promoter of vector pALV-SIN-4.2-Lys-IFNa-2B is removed and replaced with a 6.5 kb lysozyme promoter corresponding to nucleotides 7665 to 11863 of SEQ ID NO: 67 using standard methodologies known to practitioners of skill in the art, resulting in pALV-SIN-6.5-Lys-IFNa-2B. Transduction particles of the new vector pALV-SIN-6.5-Lys-IFNa-2B are produced as disclosed in U.S. patent application Ser. No. 11/542,093, filed Oct. 3, 2006.

Fertilized chicken eggs or Japanese quail eggs are windowed and about $7 \times 10^4$ pALV-SIN-6.5-Lys-IFNa-2B transducing particles are injected into the subgerminal cavity of each egg. Eggs hatch 21 or 18 days after injection and birds are identified that contain the active transgene in their genome, as described in Example 10. G1 birds which contain the transgene in their genome are produced from germline chimeras using methods known in the art.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A transgenic chicken whose genome comprises an exogenous nucleic acid sequence encoding a protein operably linked to a functional fragment of the lysozyme promoter of SEQ ID NO: 67, wherein the chicken is capable of depositing the protein in egg white.

2. The transgenic chicken of claim 1, wherein the protein is therapeutic.

3. The transgenic chicken of claim 1, wherein the nucleic acid sequence comprises a vector.

4. The transgenic avian of claim 3 wherein the vector is selected from the group consisting of a plasmid, a viral vector and an artificial chromosome.

5. The transgenic chicken of claim 1, wherein the functional fragment of the lysozyme promoter of SEQ ID NO: 67 is at least 95% identical to nucleotides 7665 to 11863 of SEQ ID NO: 67.

6. The transgenic chicken of claim 1, wherein the functional fragment of the lysozyme promoter of SEQ ID NO: 67 is identical to nucleotides 7665 to 11863 of SEQ ID NO: 67.

7. The transgenic chicken of claim 1, wherein the protein is human.

8. A method of producing protein in egg white of a transgenic chicken comprising obtaining a transgenic chicken whose genome comprises an exogenous nucleic acid sequence encoding a protein operably linked to a functional fragment of the lysozyme promoter of SEQ ID NO: 67, wherein the chicken is capable of depositing the protein in egg white; and producing the protein in egg white of the transgenic chicken.

9. The method of claim 8, wherein the functional fragment of the lysozyme promoter of SEQ ID NO: 67 is at least 95% identical to nucleotides 7665 to 11863 of SEQ ID NO: 67.

10. The method of claim 8, wherein the functional fragment of the lysozyme promoter of SEQ ID NO: 67 is identical to nucleotides 7665 to 11863 of SEQ ID NO: 67.

11. The method of claim 8, wherein the protein is human.

* * * * *